(12) United States Patent
Saito et al.

(10) Patent No.: US 8,796,492 B2
(45) Date of Patent: Aug. 5, 2014

(54) α-(UNSATURATED ALKOXYALKYL) ACRYLATE COMPOSITION AND PROCESS FOR PRODUCTION THEREOF

(75) Inventors: Makoto Saito, Suita (JP); Hiroko Izumi, Tsukuba (JP); Toshimitsu Moriguchi, Suita (JP); Tomomasa Kaneko, Suita (JP); Atsushi Tachibana, Suita (JP); Mitsuaki Makino, Suita (JP); Yasuhiro Mimura, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 51 days.

(21) Appl. No.: 13/260,110

(22) PCT Filed: Mar. 31, 2010

(86) PCT No.: PCT/JP2010/055960
§ 371 (c)(1),
(2), (4) Date: Sep. 23, 2011

(87) PCT Pub. No.: WO2010/114077
PCT Pub. Date: Oct. 7, 2010

(65) Prior Publication Data
US 2012/0016095 A1    Jan. 19, 2012

(30) Foreign Application Priority Data

Mar. 31, 2009  (JP) .................... 2009-087219
Mar. 31, 2009  (JP) .................... 2009-087220
Sep. 4, 2009   (JP) .................... 2009-204597
Sep. 29, 2009  (JP) .................... 2009-225264
Jan. 4, 2010   (JP) .................... 2010-000191

(51) Int. Cl.
*C07C 43/11*  (2006.01)
*C07C 41/06*  (2006.01)
*C07C 41/46*  (2006.01)
*C07C 43/15*  (2006.01)

(52) U.S. Cl.
CPC ............. *C07C 43/15* (2013.01); *C07C 41/06* (2013.01); *C07C 41/46* (2013.01)
USPC ................ 568/689; 568/687; 568/699

(58) Field of Classification Search
CPC .......... C07C 41/06; C07C 41/46; C07C 43/15
USPC ............ 524/556; 568/689, 687, 699; 106/316
See application file for complete search history.

(56) References Cited

U.S. PATENT DOCUMENTS

| | | | |
|---|---|---|---|
| 4,980,275 A * | 12/1990 | Goddard ................. | 430/551 |
| 5,354,895 A | 10/1994 | Besecke et al. | |
| 5,442,109 A | 8/1995 | Besecke et al. | |
| 5,783,678 A | 7/1998 | Yurugi et al. | |
| 5,834,576 A | 11/1998 | Nagano et al. | |
| 2003/0130431 A1 | 7/2003 | Kinoshita et al. | |
| 2004/0077899 A1 | 4/2004 | Kinoshita et al. | |
| 2007/0212641 A1 | 9/2007 | Wakata et al. | |
| 2008/0200581 A1* | 8/2008 | Kunita .................... | 522/104 |
| 2011/0263805 A1 | 10/2011 | Kaneko | |
| 2012/0016095 A1 | 1/2012 | Saito et al. | |

FOREIGN PATENT DOCUMENTS

| | | |
|---|---|---|
| JP | 56-018941 A | 2/1981 |
| JP | 01-143847 A | 6/1989 |
| JP | 04-134047 A | 5/1992 |
| JP | 8-325200 A | 12/1996 |
| JP | 10036309 A * | 2/1998 |
| JP | 10-226669 A | 8/1998 |
| JP | 2002-148795 A | 5/2002 |
| JP | 2002-149043 A | 5/2002 |
| JP | 2002131900 A | 5/2002 |
| JP | 2004123819 A | 4/2004 |
| JP | 3610331 | 10/2004 |
| JP | 2005-239610 A | 9/2005 |
| JP | 2010-235546 A | 10/2010 |
| WO | WO-2010/074289 A1 | 7/2010 |

OTHER PUBLICATIONS

Thompson et al; "Unusually Facile Cyclopolymerization of a New Allyl Ether Substituted Acrylate and Confirmation of Repeat Unit Structure by Inadequate NMR"; Macromolecules, 1992, 25(24), pp. 6455-6459.

Tüzün et al.; "Modeling the Cyclopolymerization of Diallyl Ether and Methyl α-[(allyloxy)Methyl]acrylate"; International Journal of Quantum Chemistry, 2007, vol. 107, p. 894-906.

Thompson et al.; "Cyclopolymerization and Characterization of a New α-Substituted Acrylate"; Polymer preprints, 1992, 33(2), pp. 140-141.

Urushisaki et al.; "Cyclopolymerization. 25. Five-Membered Ring Formation through Head-to-Head and Tail-to-Tail Additions in Radical and Anionic Polymerizations of α-(Allyloxymethyl)acrylates"; Macromolecules, 1999, 32, pp. 322-327.

* cited by examiner

*Primary Examiner* — Kelechi Egwim
(74) *Attorney, Agent, or Firm* — Novak Druce Connolly Bove + Quigg LLP

(57) ABSTRACT

An α-(unsaturated alkoxyalkyl)acrylate composition is provided which enables an α-(unsaturated alkoxyalkyl)acrylate product to be stored at a high purity for an extended period of time and can fully suppress problems such as discoloration and gelation from arising during polymerization, and a method of safely preparing α-(unsaturated alkoxyalkyl)acrylate compositions industrially, with high purity. The composition includes an α-(unsaturated alkoxyalkyl)acrylate of a specific structure and an antioxidant, the content of the antioxidant being from 0.03 to 0.5 wt % per 100 wt % of the α-(unsaturated alkoxyalkyl)acrylate.

20 Claims, 13 Drawing Sheets

FIG.1
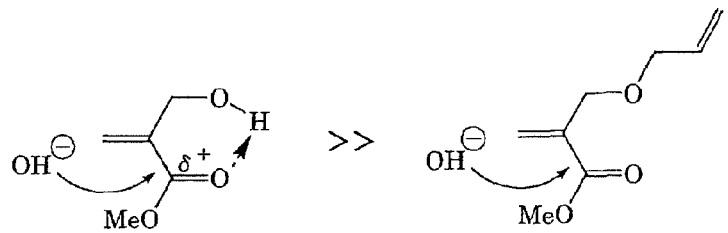
FIG.2
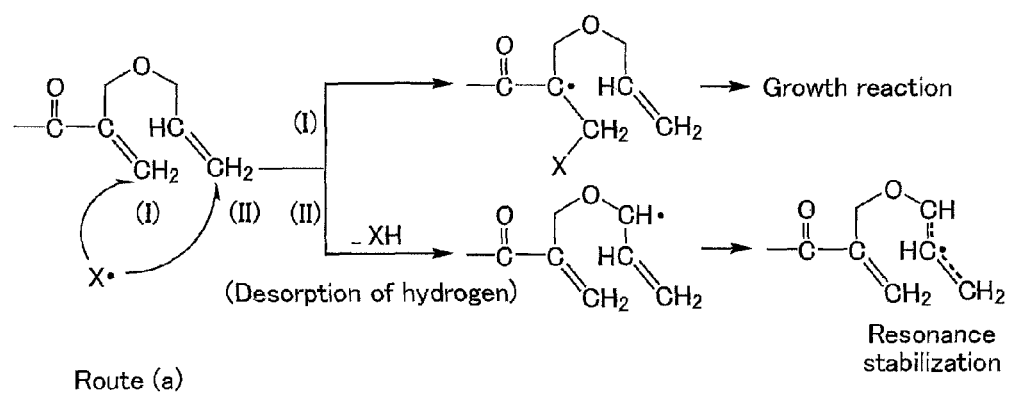
Route (a)
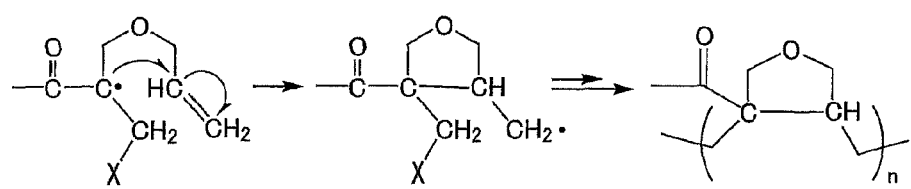
Route (b)
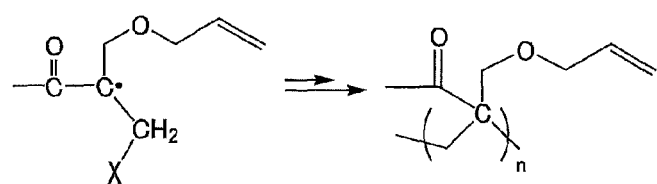

FIG.3
(Meth)Acrylic group
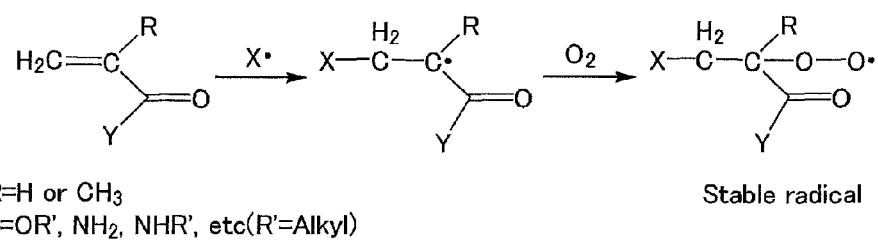
R=H or CH₃
Y=OR', NH₂, NHR', etc(R'=Alkyl)
Stable radical
AMA group
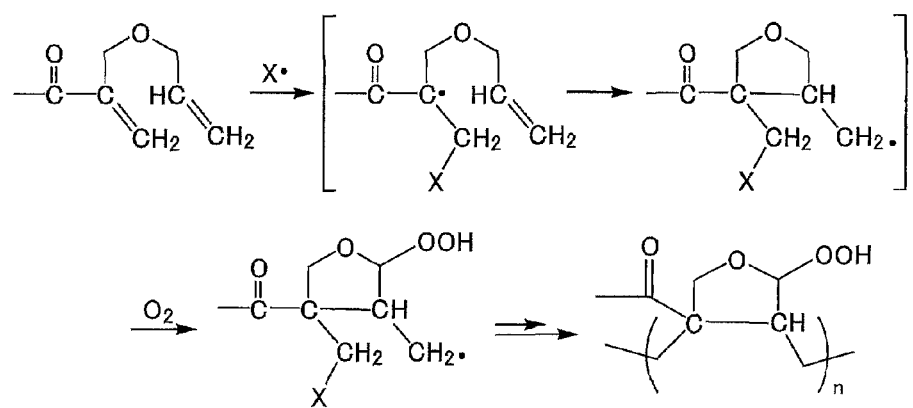

FIG.10
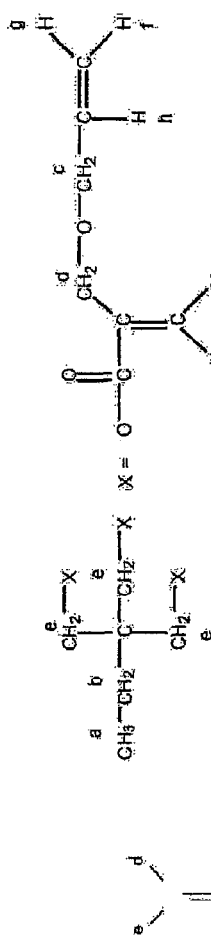
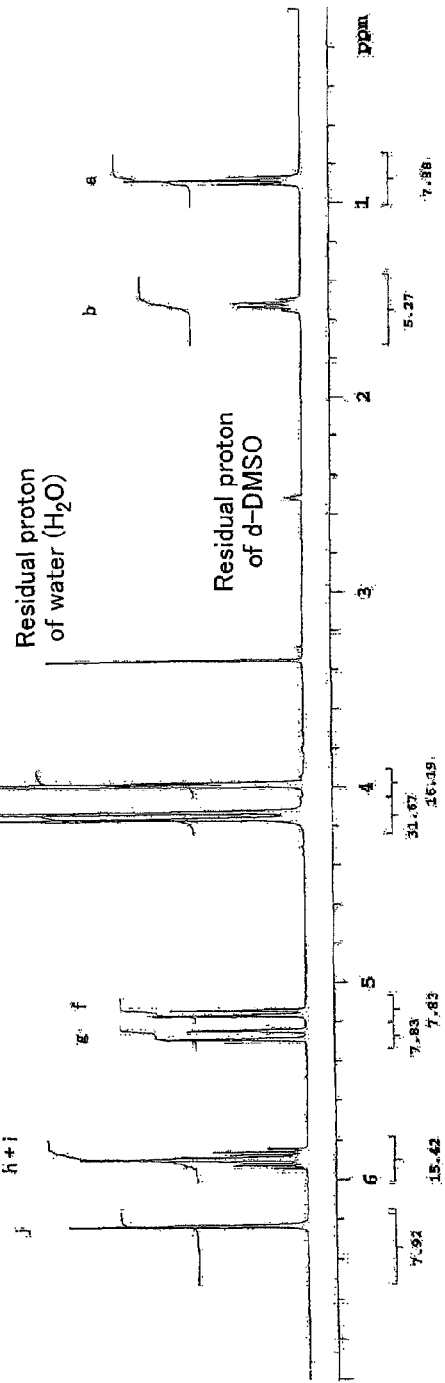

α-(UNSATURATED ALKOXYALKYL) ACRYLATE COMPOSITION AND PROCESS FOR PRODUCTION THEREOF

CROSS-REFERENCE TO RELATED APPLICATIONS

This application is a 35 U.S.C. 371 National Stage Application of International Application No. PCT/JP2010/055960, filed Mar. 31, 2010, claiming priority from Japanese Patent Application No. 2009-087219, filed Mar. 31, 2009, Japanese. Patent Application No. 2009-087220, filed Mar. 31, 2009, Japanese Patent Application No. 2009-204597, filed Sep. 4, 2009, Japanese. Application No. 2009-225264, filed Sep. 29, 2009 and Japanese Patent Application No. 2010-000191, filed Jan. 4, 2010, the entire contents of which are incorporated herein by reference in their entirety.

TECHNICAL FIELD

The present invention relates to α-(unsaturated alkoxyalkyl)acrylate compositions and methods of preparing the same. More specifically, the invention relates to α-(unsaturated alkoxyalkyl)acrylate compositions which can be advantageously used as production feedstocks or diluents for curable resin compositions and the like in a variety of fields, such as engineering plastics, optical materials and resists, and to methods of preparing the same.

BACKGROUND ART

Polymers (resins) having cyclic structures on the main chain and elsewhere, because they exhibit durability, especially outstanding heat resistance, owing to the cyclic structures, have been attracting attention as promising materials in a variety of technical fields where such properties are in demand, including the fields of engineering plastics, optical materials and resists.

Conventional methods for obtaining such resins include processes which couple together monomers having a cyclic structure by polycondensation or addition polymerization, and processes in which monomers without a cyclic structure are cyclized during addition polymerization. Of these, because methods for obtaining polymers having cyclic structures by cyclization during addition polymerization provide novel production methods which differ significantly from techniques in which first monomers having a cyclic structure are prepared, then the monomers are polymerized, the use of such production methods shows promise in a variety of technical fields that employ polymers having cyclic structures. In both approaches, methods involving addition polymerization carry out the polymerization of monomers having unsaturated bonds such as double bonds. Because molecular weight modification is generally easy and various vinyl monomers can be copolymerized under mild conditions, it is easy to adjust the physical properties in accordance with the intended application and to impart various functions. Hence, these processes are being investigated as methods of synthesizing resins for such applications as optical materials and resists which require a high degree and broad range of functionality.

In the meantime, it is recognized that, unlike the monomers commonly used in addition polymerization, monomers which cyclize during polymerization are special monomers. Such monomers are exemplified by α-(unsaturated alkoxyalkyl)acrylates having two unsaturated groups on a single molecule—an acryloyl group and an unsaturated alkoxy group, such as an α-(allyloxymethyl)acrylate, which has an allyl ether group as the unsaturated alkoxy group. This special monomer has a structure in which —$CH_2$—O—$CH_2$—CH=$CH_2$ is bonded to the 2-position carbon atom at the double bond of the acryloyl group. A cyclizing reaction between the acryloyl group and the allyl ether group arises during polymerization, resulting in the formation of a polymer having cyclic structures. Although α-(allyloxymethyl)acrylates and monomers having a similar structure, i.e., α-(unsaturated alkoxyalkyl)acrylates, can thus be regarded as useful monomers which undergo cyclopolymerization and are able to provide polymers having cyclic structures on the main chain and the like, because of their distinctive nature, very little has been published to date on the preparation and properties of such monomers.

In the circumstances, a method has been disclosed for reacting, for example, methyl α-(hydroxymethyl)acrylate with ethyl alcohol to form allyl ether compounds such as the corresponding methyl α-(ethoxymethyl)acrylate (see, for example, Patent Document 1). In this method, an allyl ether compound having a structure in which ethoxymethyl or the like is bonded at the 2-position carbon atom of the double bond on the acryloyl group is prepared. However, nothing is mentioned concerning the formation of α-(unsaturated alkoxyalkyl)acrylates.

With regard to, for example, methods of preparing conventional α-(unsaturated alkoxyalkyl)acrylates such as α-(allyloxymethyl)acrylates, methods of preparing α-position substituted acrylates by reacting a specific dialkyl-2,2'-[oxybis (methylene)]bisacrylate with an active hydrogen group-containing compound have been disclosed (see, for example, Patent Document 2). In this patent document, hydroxyl group-containing compounds are listed as examples of the active hydrogen group-containing compound. One example mentioned is ally alcohol. In addition, methods of preparing allyl ethers by reacting a specific acrylic acid ester with a hydroxyl group-containing compound have been disclosed (see, for example, Patent Document 3).

In addition, although monomers having an allyl ether structure are not themselves distinctive monomers which form polymers having cyclic structures, a method of preparing allyl ether ester monomers by way of an esterification reaction between a specific α-allyl-ω-hydroxy-polyoxyalkylene and a specific aliphatic monocarboxylic acid has been disclosed as a method for preparing monomers having an allyl ether structure (see, for example Patent Document 4). Methods for preparing α-(allyloxymethyl)acrylates by reacting a halomethyl acrylate with an allyl alcohol have also been described (see, for example, Non-Patent Document 1).

In addition, it has been disclosed that compounds obtained by inserting an allyloxymethyl group at the α-position on an acrylic acid ester undergo cyclopolymerization, giving rise to soluble polymers which have tetrahydrofuran rings on the main chain (see, for example, Non-Patent Documents 1 and 2).

Patent Document 1: Japanese Patent No. 3943180 (pages 1 and 3 of the specification)
Patent Document 2: Japanese Patent Application Laid-open No. 2005-239610 (pages 1 and 3)
Patent Document 3: Japanese Patent Application Laid-open No. H8-325200 (pages 2 and 8)
Patent Document 4: Japanese Patent No. 3610331 (pages 1, 2 and 15 of the specification)
Non-Patent Document 1: Robert D. Thompson, et al.: *Macromolecules*, vol. 25, p. 6455-6459 (American Chemical Society), 1992 (US)
Non-Patent Document 2: Michio Urushizaki, and four others: *Macromolecules*, vol. 32, p. 322-327 (1999)

DISCLOSURE OF THE INVENTION

Problem to be Solved by the Invention

The inventors have learned that, owing to the fact that α-(unsaturated alkoxyalkyl)acrylates which undergo the distinctive type of polymerization known as cyclopolymerization are special monomers differing from common acrylic monomers, substantially no investigations have hitherto been carried out on effectively utilizing such monomers, and have also learned that such monomers pose different challenges than common acrylic monomers. That is, although α-(unsaturated alkoxyalkyl)acrylates having an acryloyl group and an unsaturated alkoxy group (e.g., allyl ether group) on a single molecule may be regarded as useful monomers which, when subjected to cyclopolymerization, are capable of providing a polymer having cyclic structures on the main chain and the like, because they have a distinctive structure that includes two different types of unsaturated groups, and in particular because α-(allyloxymethyl)acrylates have a readily oxidizable allyl ether group on the molecule, the amount of peroxide formation during production and storage tends to increase. As a result, these monomers given rise to undesirable effects such as the coloration of manufactured articles or gelation during polymerization.

The inventors learned that problems similar to those mentioned above occur also in cases where α-(unsaturated alkoxyalkyl)acrylates are used as reactive diluents or curable composition monomers, from which it became apparent that there remained room for further investigation.

The present invention was ultimately arrived at in light of the above circumstances. It is therefore a first object of the invention to provide stabilized α-(unsaturated alkoxyalkyl) acrylate compositions which enable manufactured products of α-(unsaturated alkoxyalkyl)acrylates such as α-(allyloxymethyl)acrylates to be stored at a high purity for an extended period of time, and which can fully suppress problems such as coloration and gelation from arising during polymerization. A further object of the invention is to provide methods of preparing α-(unsaturated alkoxyalkyl)acrylate compositions, which methods are able to industrially obtain α-(unsaturated alkoxyalkyl)acrylates such as α-(allyloxymethyl)acrylates safely and in a high purity.

A second object of the invention is to provide curable compositions in which the above α-(unsaturated alkoxyalkyl) acrylates serve as a reactive diluent or a monomer ingredient.

Means for Solving the Problem

The inventors have conducted extensive investigations on ways of resolving the above-described problems concerning α-(unsaturated alkoxyalkyl)acrylates and methods of production thereof. As a result, they have discovered that by preparing a composition containing an α-(unsaturated alkoxyalkyl)acrylate and a specific amount of an antioxidant, it is possible to effectively suppress the amount of peroxide that forms and thereby to store the product at a high purity for an extended period of time, and to suppress problems such as coloration and gelation from arising during polymerization. This discovery made it possible to fully resolve the above problems, ultimately leading to the present invention. Accordingly, the invention enables α-(unsaturated alkoxyalkyl)acrylates to be obtained as stabilized starting monomers for cyclic polymers.

In addition, the inventors have also discovered that the foregoing α-(unsaturated alkoxyalkyl)acrylates are useful as reactive diluents and as monomer ingredients for curable compositions.

Accordingly, the invention provides an α-(unsaturated alkoxyalkyl)acrylate composition which includes: an α-(unsaturated alkoxyalkyl)acrylate represented by general formula (1) below

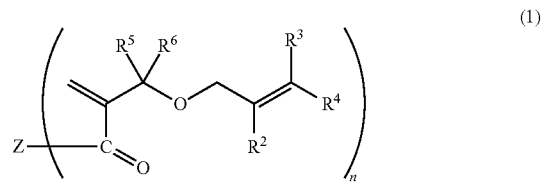

(where $R^2$, $R^3$ and $R^4$ are identically or independently a hydrogen atom or a $C_{1-30}$ organic group; $R^5$ and $R^6$ are identically or independently a hydrogen atom or a $C_{1-18}$ alkyl group which may be substituted; and Z is an n-valent organic group, with n being an integer greater than or equal to 1); and an antioxidant, wherein the antioxidant content is from 0.03 to 0.5 wt % relative to 100 wt % of the α-(unsaturated alkoxyalkyl)acrylate. In addition, "wt %" means "percent by weight".

The invention further provides a curable composition which include the above-described α-(unsaturated alkoxyalkyl)acrylate and an antioxidant.

The invention is described in detail below.

α-(Unsaturated Alkoxyalkyl) Acrylate Composition

The α-(unsaturated alkoxyalkyl)acrylate composition of the invention (also referred to below as "the composition") is a composition which includes an α-(unsaturated alkoxyalkyl) acrylate and also an antioxidant.

The α-(unsaturated alkoxyalkyl)acrylate has two types of unsaturated groups on a single molecule: an unsaturated alkoxy group such as an allyl ether group, and an acryloyl group. In the present invention, the α-(unsaturated alkoxyalkyl)acrylate is supplied and used as a monomer composition which includes also an antioxidant. That is, strictly speaking, the α-(unsaturated alkoxyalkyl)acrylate is not a monomer per se; rather, it is an entity which includes both the monomer itself and also additives and the like, and is commonly referred to and supplied as "the monomer." Therefore, "α-(unsaturated alkoxyalkyl)acrylate composition" refers to an entity which is supplied and used as a "monomer" that includes an α-(unsaturated alkoxyalkyl)acrylate monomer, a small amount of antioxidant and other, optional, additives. It may also be supplied and used as a composition containing other monomers and compounds as well.

α-(Unsaturated Alkoxyalkyl) Acrylate

The above α-(unsaturated alkoxyalkyl)acrylate is a compound of above general formula (1); that is, a compound having a structure in which an unsaturated alkoxyalkyl group ($—C(R^5)(R^6)—O—CH_2—C(R^2)=C(R^2)(R^4)$) is bonded to the α-position carbon atom at the double bond of the acrylate.

The α-(unsaturated alkoxyalkyl)acrylate composition of the invention may include, as the α-(unsaturated alkoxyalkyl) acrylate, a single type of α-(unsaturated alkoxyalkyl)acrylate or may include a plurality of α-(unsaturated alkoxyalkyl) acrylates wherein any one or more of $R^2$, $R^3$, $R^4$, $R^5$, $R^6$ and Z differs.

In above general formula (1), when n is 1, Z represents a monovalent organic group. The monovalent organic group is preferably a group of the formula —$OR^1$ (where $R^1$ is a hydrogen atom or a $C_{1-30}$ organic group).

Thus, embodiments in which n in above general formula (1) is 1, and embodiments in which n in general formula (1) is 1 and Z is a group of the formula —$OR^1$ (where $R^1$ is a hydrogen atom or a $C_{1-30}$ organic group) are all preferred embodiments of the α-(unsaturated alkoxyalkyl)acrylate composition of the invention.

In above general formula (1), when Z is a group of the above formula —$OR^1$ (where $R^1$ is a hydrogen atom or a $C_{1-30}$ organic group), the above α-(unsaturated alkoxyalkyl)acrylate is a compound represented by general formula (2) below

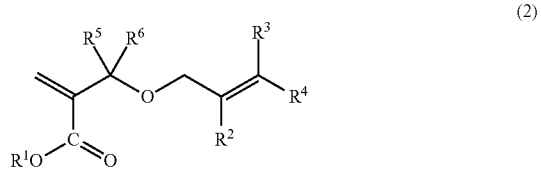

(2)

(where $R^1$ is a hydrogen atom or a $C_{1-30}$ organic group; and $R^2$, $R^3$, $R^4$, $R^5$ and $R^6$ are the same as in general formula (1)).

$R^1$ is a group that forms an ester group and represents a hydrogen atom or a $C_{1-30}$ organic group. $R^1$ is preferably a $C_{1-30}$ organic group.

The organic group may be linear or branched, or may even be cyclic. The number of carbons on the organic group is preferably from 1 to 18, more preferably from 1 to 12, and even more preferably from 1 to 8. The organic group is preferably an organic group composed of a hydrocarbon skeleton or an ether bond-containing hydrocarbon skeleton. The hydrocarbon skeleton is more preferably an acyclic saturated hydrocarbon group, an alicyclic hydrocarbon group, or an aromatic hydrocarbon group. These groups may have a substituent. That is, these groups may be substituted acyclic saturated hydrocarbon groups, substituted alicyclic hydrocarbon groups, or substituted aromatic hydrocarbon groups in which at least some of the hydrogen atoms bonded to the carbon atoms composing the groups have been replaced with a substituent. Of these, an acyclic saturated hydrocarbon which may have a substituent is more preferred.

The organic group composed of an ether bond-containing hydrocarbon skeleton is exemplified by groups with a structure in which an oxygen atom has been inserted on at least one carbon-carbon bond composing the above acrylic hydrocarbon groups, alicyclic hydrocarbon groups, and aromatic hydrocarbon groups.

Illustrative examples of the substituents include halogen atoms such as fluorine atoms, chlorine atoms, bromine atoms and iodine atoms, and also cyano groups and trimethylsilyl groups.

Preferred examples of the acyclic saturated hydrocarbon groups include methyl, ethyl, propyl, butyl, amyl, neopentyl, hexyl, octyl, and 2-ethylhexyl. At least some of the hydrogen atoms bonded to the carbon atoms composing the acyclic saturated hydrocarbon group may be substituted with halogen atoms. Preferred examples include halogen-substituted acyclic saturated hydrocarbon groups.

Preferred examples of the alicyclic hydrocarbon groups include cyclohexyl, cyclohexylmethyl, isobornyl, adamantyl, dicylopentanyl, and dicyclopentenyl. These may likewise be substituted alicyclic hydrocarbon groups in which at least some of the hydrogen atoms bonded to the constituent carbon atoms have been substituted with, for example, hydroxyl groups or halogen atoms.

Preferred examples of the aromatic hydrocarbon groups include phenyl, benzyl, naphthyl, and anthranyl. These may likewise be substituted aromatic hydrocarbon groups in which at least some of the hydrogen atoms bonded to the constituent carbon atoms have been substituted with, for example, alkoxy groups, hydroxyl groups or halogen atoms.

The organic group composed of an ether bond-containing hydrocarbon skeleton is not subject to any particular limitation, provided it has a structure in which an oxygen atom has been inserted on at least one of the carbon-carbon bonds forming the above acyclic saturated hydrocarbon group, acyclic unsaturated hydrocarbon group, alicyclic hydrocarbon group or aromatic hydrocarbon group. Illustrative examples include acyclic ether groups such as methoxyethyl, methoxyethoxyethyl, ethoxyethyl and phenoxyethyl; groups having both an alicyclic hydrocarbon group and an acyclic ether group, such as cyclohexyloxyethyl and dicyclopentenyloxyethyl; groups having both an aromatic hydrocarbon group and an acyclic ether group, such as phenoxyethyl and phenoxyethoxyethyl; and cyclic ether groups such as glycidyl, 3,4-epoxycyclohexylmethyl, tetrahydrofuranyl and tetrahydrofurfuryl.

In cases where n in above general formula (1) is an integer that is 2 or more, Z represents an n-valent linkage. Such embodiments in which Z in above general formula (1) is an n-valent linkage, with n being an integer equal to or greater than 2, are also preferred embodiments of the α-(unsaturated alkoxyalkyl)acrylate composition of the invention.

In this way, compounds with two or more partial structures other than Z in general formula (1) have crosslinkability, and thus are useful as reactive diluents and polymerizable oligomers.

In cases where n in above general formula (1) is equal to or greater than 2, n is not subject to any particular limitation so long as it is equal to or greater than 2. However, from the standpoint of ease of synthesis and storage stability, n is preferably from 2 to 100, and more preferably from 2 to 50. When the compound represented by general formula (1) is used in applications requiring a low viscosity, such as a reactive diluent, n is even more preferably from 2 to 10, and most preferably from 2 to 6. When the compound is used in applications requiring film-forming properties, such as a binder resin for paints and inks, n is even more preferably from 5 to 50, and most preferably from 10 to 50.

In cases where n in above general formula (1) is equal to or greater than 2, Z in general formula (1) is not subject to any particular limitation, provided it is a linkage capable of forming two or more covalent bonds with the carbonyl groups to which Z is bonded in general formula (1), that is, a covalently bondable linkage having a valence of 2 or more. Thus, it may be a linkage with a valence of 2 or more which bonds through a single atom, or a linkage with a valence of 2 or more which bonds through two or more atoms. However, from the standpoint of ease of synthesis and chemical stability, a linkage with a valence of 2 or more which bonds through two or more atoms is preferred.

Above Z is exemplified by corresponding polyhydric compounds which are capable of forming ester groups in combination with an α-(unsaturated alkoxyalkyl)acrylic acid. The starting material employed is not subject to any particular limitation, provided it has such a structure. Illustrative examples include low-molecular-weight dihydric alcohols such as ethylene glycol, diethylene glycol, tetraethylene glycol, propylene glycol, tripropylene glycol, butanediol, hexanediol, neopentyl glycol, 1,4-dimethylolcyclohexane, xylylene glycol, bisphenol A, bisphenol F, bisphenol S and bisphenol fluorene; low-molecular-weight trihydric alcohols such as glycerol, trimethylolpropane and ethylene oxide adducts of isocyanuric acid; low-molecular-weight tetrahydric alcohols such as pentaerythritol and ditrimethylolpropane; low-molecular-weight hexahydric alcohols such as dipentaerythritol; polyhydric phenol compounds such as phenol-novolak resins; hydroxyl group-containing polymers such as hydroxyethyl(meth)acrylate copolymers and hydroxypropyl(meth)acrylate copolymers; compounds obtained by the ring-opening addition of one or more molecule of an alkylene oxide such as ethylene oxide, propylene oxide or butylene oxide to the above low-molecular-weight polyhydric alcohols; and compounds obtained by the ring-opening addition of one or more molecule of a cyclic ester compound such as ε-caprolactone to the above low-molecular-weight polyhydric alcohols.

The compound represented by above general formula (1), wherein n is an integer equal to or greater than 2, can be prepared by reacting a polyfunctional compound with a monofunctional α-(unsaturated alkoxyalkyl)acrylate or the like. Illustrative examples of such processes include methods involving the transesterification of a polyhydric compound with an α-(unsaturated alkoxyalkyl)acrylate, methods involving the dehydration condensation of a polyhydric compound with an α-(unsaturated alkoxyalkyl)acrylic acid, methods involving the addition of a polyhydric compound with an epoxy group-containing α-(unsaturated alkoxyalkyl) acrylate such as glycidyl α-allyloxy acrylate, methods involving the addition esterification of a polycarboxylic acid with a hydroxyl group-containing α-(unsaturated alkoxyalkyl)acrylate such as hydroxyethyl α-allyloxy acrylate, methods involving the addition esterification of a polycarboxylic acid with an epoxy group-containing α-(unsaturated alkoxyalkyl)acrylate, methods involving the addition esterification of a polyepoxy compound with an α-(unsaturated alkoxyalkyl)acrylic acid, methods involving the reaction of a hydroxyl group-containing α-(unsaturated alkoxyalkyl)acrylate with a polyisocyanate compound, methods involving the addition esterification of an α-(unsaturated alkoxyalkyl) acrylic acid with a polyisocyanate compound, and methods involving the reaction of a hydroxyl group-containing α-(unsaturated alkoxyalkyl)acrylate with a polycarboxylic anhydride. The use of a method involving the transesterification of a polyhydric alcohol compound with an α-(unsaturated alkoxyalkyl)acrylate is preferred.

Examples of the polyhydric compounds include ethylene glycol, glycerol, trimethylolpropane and digylcerol. Examples of the polycarboxylic acids include succinic acid and (meth)acrylic acid polymers. Examples of the polyepoxy compounds include compounds obtained by reacting epichlorohydrin with a polyhydric alcohol compound. Examples of the polyisocyanate compounds include hexamethylene diisocyanate and isocyanurates. Examples of the polycarboxylic anhydrides include maleic anhydride copolymers.

In above general formula (1), $R^2$, $R^3$ and $R^4$ are each independently a hydrogen atom or a $C_{1-30}$ organic group. The $C_{1-30}$ organic group is the same as the $C_{1-30}$ organic group which $R^1$ may represent. A monovalent organic group or a hydrogen atom is preferred. Of these, it is more preferable for $R^2$, $R^3$ and $R^4$ to be hydrogen atoms. In this case, the compound of general formula (1) is a compound having a structure that includes an allyloxyalkyl group ($-C(R^5)(R^6)-O-CH_2-CH=CH_2$); that is, an α-(allyloxyalkyl)acrylate. In this way, embodiments in which the α-(unsaturated alkoxyalkyl)acrylate includes an α-(allyloxyalkyl)acrylate are also preferred embodiments of the invention.

In above general formula (1), $R^5$ and $R^6$ are each independently a hydrogen atom or a $C_{1-18}$ alkyl group, which alkyl group may be substituted. The alkyl group may be linear, branched, or even cyclic.

Of these, a hydrogen atom or a $C_{1-10}$ alkyl group is preferred, a hydrogen atom or a $C_{1-5}$ alkyl group is more preferred, and a hydrogen atom is especially preferred. Embodiments in which $R^5$ and $R^6$ in general formula (1) are hydrogen atoms are also preferred embodiments of the invention.

That is, it is especially preferable for the compound of general formula (1) to be a compound of general formula (3) below

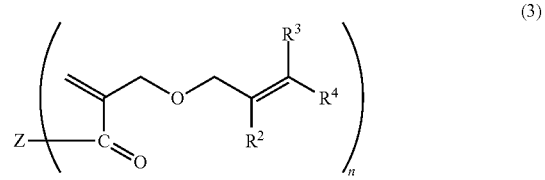

(where $R^2$, $R^3$, $R^4$, Z and n are the same as in general formula (1)). Of these, it is most preferable for the compound to be a monofunctional or polyfunctional α-(allyloxymethyl)acrylate.

That is, embodiments in which the above α-(unsaturated alkoxyalkyl)acrylate includes an α-(allyloxymethyl)acrylate are also preferred embodiments of the invention.

The above α-(allyloxymethyl)acrylate is preferably a compound of general formula (4) below

(where Z and n are the same as in general formula (1)).

In particular, in cases where Z in general formula (1) is a group represented by $-OR^1$ ($R^1$ being a hydrogen atom or a $C_{1-30}$ organic group), the above α-(unsaturated alkoxyalkyl)acrylate is preferably a compound of general formula (5) below

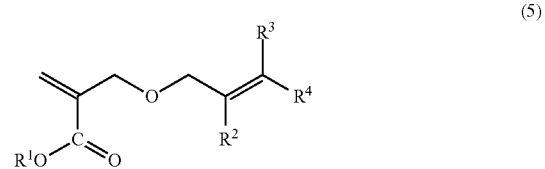

(where $R^1$, $R^2$, $R^3$ and $R^4$ are the same as in general formula (2)), and most preferably a compound of general formula (6) below

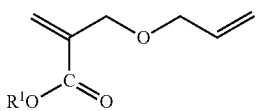

(6)

(where $R^1$ is the same as $R^1$ in general formula (2)).

In cases where the inventive composition includes an α-(allyloxymethyl)acrylate as the α-(unsaturated alkoxyalkyl)acrylate, the α-(allyloxymethyl)acrylate may be of one type or may include a plurality of α-(allyloxymethyl)acrylates of differing Z.

Illustrative examples of the α-(allyloxymethyl)acrylate include the following compounds.

Acyclic saturated hydrocarbon group-containing α-(allyloxymethyl)acrylates such as α-allyloxymethyl acrylic acid, methyl α-allyloxymethyl acrylate, ethyl α-allyloxymethyl acrylate, n-propyl α-allyloxymethyl acrylate, i-propyl α-allyloxymethyl acrylate, n-butyl α-allyloxymethyl acrylate, s-butyl α-allyloxymethyl acrylate, t-butyl α-allyloxymethyl acrylate, n-amyl α-allyloxymethyl acrylate, s-amyl α-allyloxymethyl acrylate, t-amyl α-allyloxymethyl acrylate, neopentyl α-allyloxymethyl acrylate, n-hexyl α-allyloxymethyl acrylate, s-hexyl α-allyloxymethyl acrylate, n-heptyl α-allyloxymethyl acrylate, n-octyl α-allyloxymethyl acrylate, s-octyl α-allyloxymethyl acrylate, t-octyl α-allyloxymethyl acrylate, 2-ethylhexyl α-allyloxymethyl acrylate, capryl α-allyloxymethyl acrylate, nonyl α-allyloxymethyl acrylate, decyl α-allyloxymethyl acrylate, undecyl α-allyloxymethyl acrylate, lauryl α-allyloxymethyl acrylate, tridecyl α-allyloxymethyl acrylate, myristyl α-allyloxymethyl acrylate, pentadecyl α-allyloxymethyl acrylate, cetyl α-allyloxymethyl acrylate, heptadecyl α-allyloxymethyl acrylate, stearyl α-allyloxymethyl acrylate, nonadecyl α-allyloxymethyl acrylate, eicosyl α-allyloxymethyl acrylate, ceryl α-allyloxymethyl acrylate and melissyl α-allyloxymethyl acrylate.

Hydroxy-substituted acylic saturated hydrocarbon group-containing α-(allyloxymethyl)acrylates such as hydroxyethyl α-allyloxymethyl acrylate, hydroxypropyl α-allyloxymethyl acrylate and hydroxybutyl α-allyloxymethyl acrylate. Halogen-substituted acyclic saturated hydrocarbon group-containing α-(allyloxymethyl)acrylates such as fluoroethyl α-allyloxymethyl acrylate, difluoroethyl α-allyloxymethyl acrylate, chloroethyl α-allyloxymethyl acrylate, dichloroethyl α-allyloxymethyl acrylate, bromoethyl α-allyloxymethyl acrylate and dibromoethyl α-allyloxymethyl acrylate.

Alicyclic hydrocarbon group-containing α-(allyloxymethyl)acrylates such as cyclopentyl α-allyloxymethyl acrylate, cyclopentylmethyl α-allyloxymethyl acrylate, cyclohexyl α-allyloxymethyl acrylate, cyclohexylmethyl α-allyloxymethyl acrylate, 4-methylcyclohexyl α-allyloxymethyl acrylate, 4-t-butylcyclohexyl α-allyloxymethyl acrylate, tricyclodecanyl α-allyloxymethyl acrylate, isobornyl α-allyloxymethyl acrylate, adamantyl α-allyloxymethyl acrylate, dicyclopentanyl α-allyloxymethyl acrylate and dicyclopentenyl α-allyloxymethyl acrylate. Aromatic hydrocarbon group-containing α-(allyloxymethyl)acrylates such as phenyl α-allyloxymethyl acrylate, methylphenyl α-allyloxymethyl acrylate, dimethylphenyl α-allyloxymethyl acrylate, trimethylphenyl α-allyloxymethyl acrylate, 4-t-butylphenyl α-allyloxymethyl acrylate, benzyl α-allyloxymethyl acrylate, diphenylmethyl α-allyloxymethyl acrylate, diphenylethyl α-allyloxymethyl acrylate, triphenylmethyl α-allyloxymethyl acrylate, naphthyl α-allyloxymethyl acrylate and anthranyl α-allyloxymethyl acrylate.

Acyclic ether group-type saturated hydrocarbon group-containing α-(allyloxymethyl)acrylates such as methoxyethyl α-allyloxymethyl acrylate, methoxyethoxyethyl α-allyloxymethyl acrylate, methoxyethoxyethoxyethyl α-allyloxymethyl acrylate, 3-methoxybutyl α-allyloxymethyl acrylate, ethoxyethyl α-allyloxymethyl acrylate, ethoxyethoxyethyl α-allyloxymethyl acrylate, phenoxyethyl α-allyloxymethyl acrylate and phenoxyethoxyethyl α-allyloxymethyl acrylate. α-(allyloxymethyl)acrylates having both an alicyclic hydrocarbon group and an acyclic ether group, such as cyclopentoxyethyl α-allyloxymethyl acrylate, cyclohexyloxyethyl α-allyloxymethyl acrylate, cyclopentoxyethoxyethyl α-allyloxymethyl acrylate, cyclohexyloxyethoxyethyl α-allyloxymethyl acrylate and dicyclopentenyloxyethyl α-allyloxymethyl acrylate. α-(allyloxymethyl) acrylates having both an aromatic hydrocarbon group and an acyclic ether group, such as phenoxyethyl α-allyloxymethyl acrylate and phenoxyethoxyethyl α-allyloxymethyl acrylate. Cyclic ether group-type acyclic saturated hydrocarbon group-containing α-(allyloxymethyl)acrylates such as glycidyl α-allyloxymethyl acrylate, β-methylglycidyl α-allyloxymethyl acrylate, β-ethylglycidyl α-allyloxymethyl acrylate, 3,4-epoxycyclohexylmethyl α-allyloxymethyl acrylate, 2-oxetanemethyl α-allyloxymethyl acrylate, 3-methyl-3-oxetanemethyl α-allyloxymethyl acrylate, 3-ethyl-3-oxetanemethyl α-allyloxymethyl acrylate, tetrahydrofuranyl α-allyloxymethyl acrylate, tetrahydrofurfuryl α-allyloxymethyl acrylate, tetrahydropyranyl α-allyloxymethyl acrylate, dioxazolanyl α-allyloxymethyl acrylate and dioxanyl α-allyloxymethyl acrylate.

In the inventive composition, the α-(unsaturated alkoxyalkyl)acrylate content is preferably at least 80 wt % per 100 wt % of the composition. This embodiment, which is an embodiment having an increased α-(unsaturated alkoxyalkyl)acrylate concentration, is preferred in cases where an α-(unsaturated alkoxyalkyl)acrylate itself is to be used. For example, high-purity α-(unsaturated alkoxyalkyl)acrylate compositions in which the amount of peroxide product that has formed is low are preferred for use as the "monomer" in cyclopolymerization.

The upper limit in the content of the α-(unsaturated alkoxyalkyl)acrylate is preferably 99.97 wt % or less. The lower limit is more preferably at least 90 wt %, and even more preferably at least 95 wt %.

Antioxidant

The above α-(unsaturated alkoxyalkyl)acrylate composition includes an antioxidant as an essential ingredient. However, given that the antioxidant changes after having achieved an anti-oxidant action in the composition, it is not necessary for all the antioxidant itself to be present without change at all times time within the composition. That is, the antioxidant is thought to gradually diminish after having achieved an antioxidant action. Therefore, it suffices for the inventive composition to be a composition to which an antioxidant has been added. Although the antioxidant content in the composition may fall below the above-indicated lower limit with the passage of time, to the extent that the antioxidant is added in a specific amount, such a state also falls within the technical range of the invention.

The time of antioxidant addition may be during production of the α-(unsaturated alkoxyalkyl)acrylate, or after such production. Carrying out such addition during production is preferable in that the antioxidant can be induced to act even in the reaction step or a purification step such as distillation. For example, the antioxidant may be added during production so as to remain following production, or the purification step may be modified so that the antioxidant used in the reaction step and the purification step is not completely removed in the purification step and remains even after production. In the case of addition following production, addition may be carried out after the reaction step or the purification step, or addition may be carried out during storage. Addition is preferably carried out to a given concentration following the purification step. From the standpoint of suppressing both coloration of the α-(unsaturated alkoxyalkyl)acrylate composition as the product and the amount of peroxide that forms, addition so as to set the antioxidant to a given concentration at an early stage following the purification step is more preferred.

In cases where the starting material for producing the α-(unsaturated alkoxyalkyl)acrylate includes an antioxidant and in cases where the compounds, monomers and the like present in the α-(unsaturated alkoxyalkyl)acrylate composition include an antioxidant, the antioxidants included therein may be used as the antioxidant in the α-(unsaturated alkoxyalkyl)acrylate composition of the invention. In such cases, although the operation of adding an antioxidant itself to the α-(unsaturated alkoxyalkyl)acrylate composition is not carried out, this does not change the fact that the composition is one to which an antioxidant has been added in such cases as well. However, it is preferable to add the antioxidant to a given concentration after the purification step, as in the subsequently described inventive methods of preparation.

The antioxidant in the invention is a compound which inhibits oxidizing effects on the α-(unsaturated alkoxyalkyl) acrylate, and therefore is a compound or composition which inhibits an increase in the amount of peroxide which forms. Any compound which, in technical fields where monomers are used, is recognized as an antioxidant by persons of ordinary skill in the art will suffice. Compounds or compositions which are generally recognized as radical polymerization inhibitors or radical chain inhibitors may be used as the antioxidant. However, in the practice of the invention, because the effects differ considerably depending on the type of antioxidant and other factors, it is preferable to select the antioxidant according to the application in which the α-(unsaturated alkoxyalkyl)acrylate is to be employed and the methods of storage and use. Moreover, because the fact that unsaturated alkoxy groups such as allyl ether groups readily oxidize is thought to be one cause of the above-described problems, it may be regarded as preferable to select an antioxidant which exhibits effects against the oxidation of unsaturated alkoxy groups such as allyl ether groups. Preferred forms of the antioxidant will be mentioned later.

The above α-(unsaturated alkoxyalkyl)acrylate composition contains from 0.03 to 0.5 wt % of antioxidant per 100 wt % of α-(unsaturated alkoxyalkyl)acrylate. As noted above, in the present invention, it is thought that all of the antioxidant which has been added to the α-(unsaturated alkoxyalkyl) acrylate does not remain unchanged, but rather gradually decreases after achieving an anti-oxidant action. Therefore, the phrase "contains from 0.03 to 0.5 wt % of antioxidant per 100 wt % of the α-(unsaturated alkoxyalkyl)acrylate" means that the total amount of antioxidant added to the α-(unsaturated alkoxyalkyl)acrylate should be from 0.03 to 0.5 wt % per 100 wt % of the α-(unsaturated alkoxyalkyl)acrylate. At an antioxidant content below the above range, the effects anticipated from addition of the antioxidant may not appear. On the other hand, at an antioxidant content greater than the above range, the amount of antioxidant becomes excessive and falls outside of the range at which suitable effects are achieved. The lower limit value is preferably at least 0.04 wt %, and more preferably at least 0.05 wt %. The upper limit value is preferably 0.4 wt % or less, more preferably 0.3 wt % or less, still more preferably 0.2 wt % or less, and most preferably 0.1 wt % or less.

Moreover, in the above composition, because the α-(unsaturated alkoxyalkyl)acrylate is to be used as a monomer, it is preferable for the antioxidant to be included in a total amount which falls within the above range during storage. Therefore, in cases where antioxidant is added during α-(unsaturated alkoxyalkyl)acrylate production and removed in the purification step, the antioxidant that has been removed in the purification step is not included in the total amount of antioxidant in the α-(unsaturated alkoxyalkyl)acrylate composition during storage.

More Preferred Embodiments of the Composition

Preferred embodiments of the α-(unsaturated alkoxyalkyl) acrylate composition of the invention include (1) an embodiment in which the antioxidant includes a phenolic antioxidant and/or a phosphorus-based antioxidant; (2) an embodiment which has a content of unsaturated alkyl ester or of acrylate having a hydroxyalkyl group at the α-position per 100 wt % of the α-(unsaturated alkoxyalkyl)acrylate of 1 wt % or less, (3) an embodiment in which the nitrogen content per 100 wt % of the α-(unsaturated alkoxyalkyl)acrylate is 100 ppm or less, and (4) an embodiment in which the amount of peroxide per 100 wt % of the α-(unsaturated alkoxyalkyl)acrylate is 50 ppm or less. These preferred embodiments (constituent features) may be arranged so that any one constituent feature is satisfied or so that any combination of two or more constituent features is satisfied.

These preferred embodiments are described below in order.

In the above embodiment (1) in which the antioxidant includes (as an essential component) a phenolic antioxidant and/or a phosphorus-based antioxidant, the oxidation-suppressing effects and the amount of peroxide formation-suppressing effects on the α-(unsaturated alkoxyalkyl)acrylate are pronounced. The action in suppressing the oxidation of unsaturated alkoxy groups such as allyl ether groups appears to be particularly effective. The antioxidant is effective both during production and during storage. In cases where the above antioxidant is added during production, it is preferable for the antioxidant to be present at the time of storage as well. It is also acceptable for the antioxidant to be added only during storage.

Of the above phenolic antioxidant and phosphorus-based antioxidant, either type of antioxidant may be used or both types of oxidant may be used. However, an embodiment in which a phenolic antioxidant is used, and particularly an embodiment in which (1-1) a quinone-type antioxidant is used or an embodiment in which (1-2) a phenolic antioxidant and a phosphorus-based antioxidant are both used, is preferred. In the case of (1-2), it is preferable to combine the phenolic antioxidant as a primary antioxidant, i.e., a radical chain inhibitor (radical scavenger), with the phosphorus-based antioxidant as a secondary antioxidant, i.e., a peroxide-decomposing agent for reducing the amount of peroxide that forms. In this way, gelation during polymerization using the α-(unsaturated alkoxyalkyl)acrylate can be effectively suppressed. The weight ratio when combining the phenolic antioxidant and the phosphorus-based antioxidant is set to a phenolic antioxidant to phosphorus-based antioxidant ratio of preferably from 10:90 to 90:10, and more preferably from 25:75 to 75:25. A form in which these are used in a ratio of substantially 1:1 is most preferred.

Here, "the antioxidant includes (as an essential component) a phenolic antioxidant and/or a phosphorus-based antioxidant" means that some or all of the antioxidant used in the invention is a phenolic antioxidant and/or a phosphorus-based antioxidant, with the use of a phenolic antioxidant and/or a phosphorus-based antioxidant as the chief component of the antioxidant being preferred, and the use of substantially a phenolic antioxidant and/or a phosphorus-based antioxidant alone as the antioxidant being more preferred.

One, two or more of each of the phenolic antioxidant and the phosphorus-based antioxidant may be used.

Preferred examples of the phenolic antioxidant include quinone-type antioxidants such as hydroquinone, 2-t-butylhydroquinone, 2,5-di-t-amylhydroquinone, 2,5-di-t-butylhydroquinone, 2,2'-methylenebis(4-methyl-6-t-butylphenol) and 2,2'-methylenebis(4-ethyl-6-t-butylphenol); and alkylphenol-type antioxidants such as p-methoxyphenol, 2,6-di-t-butyl-4-methylphenol, 1,1,3-tris-(2-methyl-4-hydroxy-5-t-butylphenol)butane, tris(3,5-di-t-butyl-4-hydroxybenzyl) isocyanurate, 4,4-butyridenebis(3-methyl-6-t-butylphenol), n-octadecyl-3-(3',5'-di-t-butyl-4'-hydroxyphenyl)propionate, tetrakis(methylene-3-(3',5'-di-t-butyl-4'-hydroxyphenyl)propionate)methane, triethylene glycol bis[3-(3-t-butyl-5-methyl-4-hydroxyphenyl)propionate, N,N-bis-3-(3',5'-di-t-butyl-4-hydroxyphenyl)propionyl hexamethylene diamine and 1,3,5-trimethyl-2,4,6-tris(3,5-di-t-butyl-4-hydroxybenzyl)benzene.

The phosphorus-based antioxidant used may be a phenyl phosphite-type compound or some other phosphorus atom-containing compound. Preferred examples include triphenylphosphine, triphenyl phosphite, diphenylisodecyl phosphite, phenyldiisodecyl phosphite, 4,4'-butyridenebis(3-methyl-6-t-butylphenylditridecyl) phosphite, cyclic neopentanetetraylbis(octadecyl phosphite), tris(nonylphenyl) phosphite, tris(mono and/or dinonylphenyl) phosphite, diisodecylpentaerythritol diphosphite, di(2,4-di-tert-butylphenyl)-pentaerythritol diphosphite, 9,10-dihydro-9-oxa-10-phosphaphenanthrene-10-oxide, 10-(3,5-di-t-butyl-4-hydroxybenzyl)-9,10-dehydro-9-oxa-10-phosphaphenanthrene-10-oxide, 10-decyloxy-9,10-dihydro-9-oxa-10-phosphaphenanthrene, tris(2,4-di-t-butylphenyl) phosphite, cyclic neopentanetetraylbis(2,4-di-t-butylphenyl) phosphite, cyclic neopentanetetraylbis(2,6-di-t-butyl-4-methylphenyl)phosphite, 2,2-methylenebis(4,6-di-t-butylphenyl)octyl phosphite and 3,5-di-tert-butyl-4-hydroxybenzylphosphate diethyl ether.

The above embodiment (2) which has a content of unsaturated alkyl ester or acrylate having a hydroxyalkyl group at the α-position per 100 wt % of the α-(unsaturated alkoxyalkyl)acrylate of 1 wt % or less is achieved by suppressing the content within the product of unsaturated alkyl ester which generally forms as a by-product during α-(unsaturated alkoxyalkyl)acrylate production or of acrylate having a hydroxyalkyl group at the α-position which can be used during α-(unsaturated alkoxyalkyl)acrylate production. For example, by making the content of unsaturated alkyl ester low, concerns in the present invention such as coloration of the polymer or gelation at the time of polymerization can be effectively resolved. Moreover, by making the content of acrylate having a hydroxyalkyl group at the α-position low, the amount of hydroxyl groups (OH groups) that are reactive during polymerization decreases, enabling side reactions to be suppressed in various treatments of the polymer.

Also, in this specification, "unsaturated alkyl ester" which may be included in the composition refers to an ester of an unsaturated alcohol represented by general formula (7) below

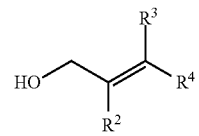

(7)

(where $R^2$, $R^3$ and $R^4$ are the same as in above general formula (1)) and an acrylate that is a starting material, a product and/or a by-product, which ester is one of the starting materials for the α-(unsaturated alkoxyalkyl) acrylate. The content of such an unsaturated alkyl ester (unsaturated alkyl ester content) refers to the combined amount of esters of the α-(hydroxymethyl)acrylate used as a starting material or intermediate and the unsaturated alcohol of general formula (7), esters of α-(unsaturated alkoxyalkyl)acrylate which obtained as the product and the unsaturated alcohol of general formula (7), and esters, which are by-products, of α-(alkoxyalkyl)acrylic acids and unsaturated alcohols. For example, in a case where the above α-(unsaturated alkoxyalkyl)acrylate is α-(allyloxymethyl)acrylate, the content is the combined amount of allyl α-(hydroxymethyl)acrylate, which is the allyl ester of α-(hydroxymethyl)acrylate serving as a starting material or an intermediate; allyl α-(allyloxymethyl)acrylate which is the allyl ester obtained as the product; and allyl α-(alkoxymethyl)acrylates which are by-products.

In cases where the α-(unsaturated alkoxyalkyl)acrylate is an α-(allyloxyalkyl)acrylate, the above-mentioned unsaturated alkyl ester is the allyl ester.

Given that the unsaturated alcohol of general formula (7) is one of the starting materials of the α-(unsaturated alkoxyalkyl)acrylate, when the α-(unsaturated alkoxyalkyl)acrylate is an α-(allyloxymethyl)acrylate, the unsaturated alcohol is allyl alcohol. Including allyl alcohol in the above unsaturated alcohol is also a preferred embodiment of the invention. In the subsequently described methods of preparing α-(unsaturated alkoxyalkyl)acrylates, including allyl alcohol in the unsaturated alcohol is also a preferred embodiment of the invention.

Here, in order to control the unsaturated alkyl ester content in the α-(unsaturated alkoxyalkyl)acrylate product, the preparation method for obtaining an α-(unsaturated alkoxyalkyl)acrylate may be a method which includes the step of reacting an α-(hydroxymethyl)acrylate with an unsaturated alcohol of general formula (7) by the dropwise addition of the unsaturated alcohol. Alternatively, unsaturated alkyl ester may be thoroughly removed in the purification step in α-(unsaturated alkoxyalkyl)acrylate production. The combined use of these two methods is preferred.

Of the foregoing modes for reducing the amount of unsaturated alkyl ester, in a method for the dropwise addition of an unsaturated alcohol, the amount of unsaturated alkyl ester produced can be fully suppressed by carrying out dropwise addition of the unsaturated alcohol rather than batchwise addition. In this way the purification step can be simplified, and the yield of α-(unsaturated alkoxyalkyl)acrylate purification can be increased.

With regard to the method of removing the unsaturated alkyl ester in the purification step, because it appears as if the amount of unsaturated alkyl ester cannot be controlled in commonly carried out purification steps, in a preferred embodiment of the invention, the unsaturated alkyl ester content is controlled so as to fall within the above range (the upper limit). It is preferable to carry out distillation so as to achieve this unsaturated alkyl ester content, and more preferable to carry out distillation using a distillation column having a number of plates. The upper limit is more preferably 0.7 wt % or less, and even more preferably 0.5 wt % or less. The lower limit is preferably such that the unsaturated allyl ester content becomes substantially 0 (zero), although the outstanding effects of the invention can be fully achieved at a content within the above range (upper limit).

Measurement of the unsaturated alkyl ester content may be carried out immediately after production via a purification step and/or during storage following production. However, because there appears to be substantially no increase in the amount of unsaturated alkyl ester in an ordinary storage state, aside from cases in which the amount of unsaturated alkyl ester is controlled as described above, measurement may be carried out at any time.

The "acrylate having a hydroxyalkyl group at the α-position" which may be included in the composition refers to one of the compounds that may be used as a starting material or an intermediate to obtain an α-(unsaturated alkoxyalkyl)acrylate, and has general formula (8) below

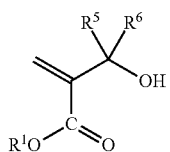

(8)

(where $R^1$, $R^5$ and $R^6$ are the same as in general formula (2)). For example, in cases where the α-(unsaturated alkoxyalkyl)acrylate is a compound of general formula (5), the acrylate having a hydroxyalkyl group at the α-position corresponds to an α-(hydroxymethyl)acrylate in which $R^5$ and $R^6$ in general formula (8) above are hydrogen atoms.

For an embodiment in which the content of acrylate having a hydroxyalkyl group at the α-position has been reduced, it is preferable to obtain an α-(unsaturated alkoxyalkyl)acrylate by subsequently described Preparation Method 3 and/or Preparation Method 4. In this way, an α-(unsaturated alkoxyalkyl)acrylate composition in which the content of acrylate having a hydroxyalkyl group at the α-position has been sufficiently reduced can be advantageously obtained.

As noted above, the upper limit in the content of acrylate having a hydroxyalkyl group at the α-position per 100 wt % of the α-(unsaturated alkoxyalkyl)acrylate is preferably 1 wt % or less, more preferably 0.7 wt % or less, and even more preferably 0.5 wt % or less. It is preferable for the lower limit in the content of acrylate having a hydroxyalkyl group at the α-position to be substantially 0 (zero), although the outstanding effects of the invention can be fully achieved within the above-indicated range (at or below the upper limit).

Here, in cases where the α-(unsaturated alkoxyalkyl)acrylate composition includes both an unsaturated alkyl ester and an acrylate having a hydroxyalkyl group at the α-position, the respective contents of the unsaturated alkyl ester and the acrylate having a hydroxyalkyl group at the α-position per 100 wt % of the α-(unsaturated alkoxyalkyl)acrylate are preferably 1 wt % or less, more preferably 0.7 wt % or less, and even more preferably 0.5 wt % or less. In particular, the total amount of the unsaturated alkyl ester and the acrylate having a hydroxyalkyl group at the α-position per 100 wt % of the α-(unsaturated alkoxyalkyl)acrylate is preferably 1 wt % or less, more preferably 0.7 wt % or less, and even more preferably 0.5 wt % or less.

The above embodiment (3) in which the nitrogen content per 100 wt % of the α-(unsaturated alkoxyalkyl)acrylate is 100 ppm or less is achieved by suppressing the content within the product of the amine catalysts (and, in cases where the catalysts chemically change, compounds having the nitrogen atoms of the catalysts) commonly used in the production of α-(unsaturated alkoxyalkyl)acrylate. In this way, concerns within the invention, such as coloration of the polymer or gelation during polymerization, can be effectively resolved. In order to control the nitrogen content in the α-(unsaturated alkoxyalkyl)acrylate product, the amine catalyst should be fully removed in the purification step during preparation of the α-(unsaturated alkoxyalkyl)acrylate. However, because it appears to be impossible to control the nitrogen content in the purification steps commonly carried out, in a preferred embodiment of this invention, the nitrogen content is controlled so as to fall within the above range (at or below the upper limit).

In order to have the nitrogen content reach the above range (at or below the upper limit), an especially preferred purification condition is to remove the amine catalyst by thorough rinsing with water prior to purification by distillation. The upper limit in the nitrogen content is more preferably 80 ppm or less, and even more preferably 50 ppm or less. The lower limit is preferably a nitrogen content of substantially 0 (zero), although the outstanding effects of the invention can be fully achieved within the above range (at or below the upper limit).

The time at which the nitrogen content is measured may be, for example, immediately after production via a purification step and/or during storage following production. Because it is thought that the nitrogen content substantially does not increase during a normal storage state, measurement at any time is appropriate, except in cases where the nitrogen content is controlled as mentioned above.

In above embodiment (4) in which the amount of peroxide per 100 wt % of the α-(unsaturated alkoxyalkyl)acrylate is 50 ppm or less, by suppressing in this way the amount of peroxide formed, concerns in the invention, such as coloration of the polymer or gelation during polymerization, can be effectively resolved. The means for controlling the amount of peroxide in the α-(unsaturated alkoxyalkyl)acrylate product is to use an antioxidant on the α-(unsaturated alkoxyalkyl)acrylate, and serves as the preferred embodiment recited in this specification.

The upper limit in the amount of peroxide is more preferably 40 ppm or less, and even more preferably 30 ppm or less. The lower limit is preferably an amount of peroxide which is substantially 0 (zero), although realistically a small amount of peroxide is assumed to be remaining. Still the outstanding effects of the invention can be fully achieved within the above range (at or below the upper limit).

The time at which the amount of peroxide is measured may be, for example, during production and/or during storage following production. However, when α-(unsaturated alkoxyalkyl)acrylate is used as the monomer, from the standpoint of suppressing polymer coloration and gelation during polymerization, it is preferable for measurement of the peroxide amount to be carried out in a storage state and for the amount to fall within the above-indicated range (at or below the upper limit).

In the above preferred embodiments of the invention, the measurement methods used in the subsequently described examples of the invention may be employed to measure the unsaturated alkyl ester content, the nitrogen content and the amount of peroxide.

Above embodiments (2) to (4) specify the quality or state in the α-(unsaturated alkoxyalkyl)acrylate composition product. However, because these numerical ranges (upper limits) all relate to coloration of the polymer or gelation during polymerization, it is preferable to employ an embodiment which combines two or more of the above. For example, it is more preferable to adopt an embodiment in which both (2) the content of unsaturated alkyl ester of acrylate having a hydroxyalkyl group at the α-position is 1 wt % or less and (3) the nitrogen content is 100 ppm or less, and still more preferable to adopt an embodiment which additionally satisfies (4) the condition that the amount of peroxide is 50 ppm or less. In order to achieve an embodiment in which any two or more of (2) to (4) above have been combined, the increase in the amount of peroxide is suppressed using an antioxidant for the α-(unsaturated alkoxyalkyl)acrylate, in addition to which both the content of nitrogen from the amine catalyst and the like, and the content of unsaturated alkyl ester as a by-product in the purification step at the time of production are reduced to within the above-indicated ranges (at or below upper limits). In this way, not only will the α-(unsaturated alkoxyalkyl) acrylate composition have been highly purified as a chemical product, the unprecedented attribute of suppressing polymer coloration and gelation during polymerization will be achieved.

Moreover, as mentioned above, even when used as a reactive diluent or as a monomer component in a curable composition, the α-(unsaturated alkoxyalkyl)acrylate composition is useful for enhancing the physical properties of the cured product.

Other Ingredients

The inventive composition may include other compounds in addition to the α-(unsaturated alkoxyalkyl)acrylate and the antioxidant. For example, when the composition is to be used as a polymerization starting material, it may include one, two or more other radical polymerizable monomers which polymerize with the α-(unsaturated alkoxyalkyl)acrylate (i.e., radical polymerizable, double bond-containing compounds other than α-(unsaturated alkoxyalkyl)acrylates; also referred to below as "radical polymerizable monomers"). These monomers are radical polymerizable unsaturated group-containing monomers which polymerize under the effect of heating or exposure of actinic energy radiation. The types and amounts of other radical polymerizable monomers used may be suitably selected according to the properties and intended use of the polymer produced. One, two or more additives, such as chain transfer agents, may also be included.

The above radical polymerizable monomer is exemplified by various types of monomers. Preferred use may be made of, for example, at least one monomer selected from the group composed of (meth)acrylic acid esters, (meth)acrylamides, unsaturated monocarboxylic acids, unsaturated polycarboxylic acids, unsaturated monocarboxylic acids that have been chain extended between the unsaturated group and the carboxyl group, unsaturated acid anhydrides, aromatic vinyls, N-substituted maleimides, macromonomers, conjugated dienes, vinyl esters, vinyl ethers, N-vinyl compounds and unsaturated isocyanates. Use of the following radical polymerizable monomers is industrially advantageous.

When use is made of a composition which includes a compound wherein n in general formula (1) of the invention is an integer greater than or equal to 2, because such a composition is cross-linkable and has excellent adhesive properties, it can be advantageously used as a curable composition. Of course, the effects of the antioxidant are achieved even in cases where a compound in which n in general formula (1) is an integer greater than or equal to 2 is used.

Preparation Methods

Methods of preparing the α-(unsaturated alkoxyalkyl) acrylate compositions of the invention are described below.

The steps in the preparation of an α-(unsaturated alkoxyalkyl)acrylate of the invention are initially described below in brief, but are not limited to this abbreviated account. Even when preparation has been carried out by another method, cases in which a composition or preparation method of the invention fall within the scope of the invention.

In the present invention, for example, following preparation of the α-(unsaturated alkoxyalkyl)acrylate, the inventive composition can be obtained by carrying out a purification step, followed by a step in which the antioxidant is added and mixed therewith.

For example, a preferred example of a method for preparing an α-(allyloxymethyl)acrylate is a process in which the following reaction steps (a) to (c) are carried out. It is preferable for all of these reaction steps to use an amine catalyst. That is, processes in which these reaction steps include a step wherein reaction is carried out in the presence of an amine catalyst are also preferred embodiments of the invention.

(a) The step of reacting an acrylic acid ester with paraformaldehyde to obtain α-(hydroxymethyl)acrylate.

(b) The step of obtaining 2,2'-[oxybis(methylene)]bisacrylate from α-(hydroxymethyl)acrylate.

(c) The step of reacting 2,2'-[oxybis(methylene)]bisacrylate with allyl alcohol to form α-(allyloxymethyl)acrylate and α-(hydroxymethyl)acrylate.

Of the above steps, it is also desirable to combine the above reaction steps (b) and (c), and thereby carry out a step in which an α-(hydroxymethyl)acrylate and allyl alcohol are reacted to form an α-(allyloxymethyl)acrylate and an α-(hydroxymethyl)acrylate. That is, it is preferable for the above preparation method to include a step in which an acrylate having a hydroxyalkyl group at the α-position, such as an α-(hydroxymethyl)acrylate, is reacted with an unsaturated alcohol of above general formula (7). Alternatively, the respective steps may be carried out separately and α-(hydroxymethyl)acrylate or 2,2'-[oxybis(methylene)]bisacrylate formed as the intermediate and reacted, or either compound may be added as the reaction starting material and reacted.

In the above reaction steps, an α-(hydroxymethyl)acrylate forms together with the α-(allyloxymethyl)acrylate serving as the target substance, but this α-(hydroxymethyl)acrylate may be reused as a starting material for obtaining an α-(allyloxymethyl)acrylate.

In the above reaction steps, a method in which the hydroxyl group on α-(hydroxymethyl)acrylate is acetylated to form α-(acetoxymethyl)acrylate, and this α-(acetoxymethyl)acrylate is reacted with allyl alcohol is also preferred.

In embodiments which include the step of carrying out the reaction in the presence of an amine catalyst, the above reaction steps are carried out in the presence of an amine catalyst.

The amine catalyst is exemplified by primary amine compounds, secondary amine compounds and tertiary amine compounds, although the use of a tertiary amine compound, i.e., a tertiary amine catalyst, is preferred. By using such an amine catalyst, side reactions are reduced, enabling a high-purity α-(allyloxymethyl)acrylate composition to be more efficiently produced.

Illustrative examples of tertiary amine catalysts include monoamine compounds such as trimethylamine, triethylamine, tri-n-butylamine, dimethylethylamine and dimethyl-n-butylamine; diamine compounds such as tetramethylethylenediamine, tetramethylpropylenediamine and tetramethylbutylenediamine; cyclic structure-containing amine compounds such as 1,4-diazabicyclo[2.2.2]octane, DBU (available under this trade name from San-Apro Ltd.) and DBN (available under this trade name from San-Apro Ltd.); and weakly basic ion-exchange resins such as Diaion WA-10 (available under this trade name from Mitsubishi Chemical Corporation), Dowex MWA-1 (available under this trade name from Dow Chemical) and Amberlite IRA-68 (available under this trade name from Rohm and Haas Company). These catalysts, in the case of compounds such as trimethylamine having a low boiling point, may be used as solutions in water or an inert organic solvent. Moreover, a single type of catalyst may be used alone, or two or more types may be suitably mixed. Of these, monoamine compounds and/or cyclic structure-containing amine compounds are preferred. Trimethylamine and/or 1,4-diazabicyclo[2.2.2]octane are more preferred.

The amount of the amine catalyst used is preferably from 0.01 to 50 mol % per 100 mol % of paraformaldehyde in above reaction step (a). The amount of the amine catalyst used is preferably from 0.01 to 50 mol % per 100 mol % of acrylate having a hydroxyalkyl group at the α-position in above reaction step (b). The amount of the amine catalyst used is preferably from 0.01 to 50 mol % per 100 mol % of 2,2'-[oxybis(methylene)]bisacrylate in above reaction step (c). At an amount below 0.01 mol % in any of the steps, the catalyst activity may not be fully achieved, the reaction time may become too long, and it may become impossible to efficiently produce an α-(unsaturated alkoxyalkyl)acrylate such as an α-(allyloxymethyl)acrylate. On the other hand, at an amount in excess of 50 mol %, further improvement in the catalyst effects, such as shortening of the reaction time, which are proportional to the increase in the amount of catalyst is unlikely to occur, resulting in wasteful use of some of the catalyst added, which may be economically disadvantageous. In each step, addition in an amount of from 0.5 to 20 mol % is more preferred.

In order to suppress polymerization of the starting material, intermediate and product, it is preferable for the reaction temperature in above reaction steps (a) to (c) to be from 10 to 150° C.

With regard to above reaction step (c), it is preferable for allyl alcohol to be used in an amount relative to methyl 2,2'-[oxybis(methylene)]bisacrylate which is such as to set the molar ratio of methyl 2,2'-[oxybis(methylene)]bisacrylate to allyl alcohol at from 0.05 to 20.

In order to suppress the polymerization of methyl acrylate, methyl α-(hydroxymethyl)acrylate, methyl 2,2'-[oxybis(methylene)bisacrylate and methyl α-(allyloxymethyl)acrylate, it is preferable to use a polymerization inhibitor or molecular oxygen.

The method of preparing the α-(unsaturated alkoxyalkyl)acrylate is preferably one which involves preparation via a transesterification reaction from a lower ester of an α-allyloxymethyl acrylic acid such as methyl α-allyloxymethyl acrylate or ethyl α-allyloxymethyl acrylate. In this case, it is preferable to carry out transesterification between a lower ester of an α-(unsaturated alkoxyalkyl)acrylic acid in which the unsaturated alkyl ester content, nitrogen content and/or amount of peroxide have been reduced to the above-indicated preferred ranges and an unsaturated alcohol, and using a transesterification catalyst. By also optionally carrying out purification and, after purification, adding an antioxidant, it is possible to obtain the α-(unsaturated alkoxyalkyl)acrylate composition of the invention. Such an embodiment is also a preferred embodiment of the invention.

Next, the purification step is described. The purification step may be any step which carries out a purification method that can be used in the technical field of the invention. Preferred examples include steps in which at least one of the methods of, for example, rinsing, extraction and distillation is carried out. The purification conditions may be suitably selected depending on the impurities such as catalyst and by-products which are present in the crude α-(unsaturated alkoxyalkyl)acrylate, and on the extent to which these are to be removed to obtain the purified α-(unsaturated alkoxyalkyl)acrylate. Preferably, in order to obtain the above-described preferred embodiments of the inventive α-(unsaturated alkoxyalkyl)acrylate composition, the purification method and purification conditions should be suitably selected in such a way that the nitrogen content and unsaturated alkyl ester content fall within the above-indicated ranges (at or below the upper limits). An embodiment which includes a step wherein the amine catalyst is removed by rinsing with water and a step wherein the unsaturated alkyl ester content is reduced by distillation are also contained in the preferred embodiment of the invention.

In the step wherein an antioxidant is added to the above purified α-(unsaturated alkoxyalkyl)acrylate, adding the antioxidant as soon as possible following the purification step is preferable for suppressing an increase in the amount of peroxide. Also, as mentioned above, it is possible to add a single antioxidant, or to add two or more different antioxidants. Addition may be carried out all at once, successively, or continuously.

Preparation Method 1

The first preparation method of the invention (referred to below as "Preparation Method 1") is a method for preparing an α-(unsaturated alkoxyalkyl)acrylate composition which includes a step of reacting an acrylate having a hydroxyalkyl group at the α-position with an unsaturated alcohol represented by above general formula (7) by dropwise addition of the unsaturated alcohol. That is, the unsaturated alcohol, rather than being added all at once, is preferably added in a dropwise manner, thereby enabling the amount of unsaturated alkyl ester that forms to be more fully suppressed. By thus suppressing the formation of unsaturated alkyl ester in the reaction step, it is possible to simplify the subsequent purification step and further enhance the purification yield. Moreover, in purification by distillation, for example, when an attempt is made to obtain high-purity α-(unsaturated alkoxyalkyl)acrylate from a reaction mixture containing a large amount of unsaturated alkyl ester having a higher boiling point than the target α-(unsaturated alkoxyalkyl)acrylate, owing to the need to increase the reflux ratio or reduce the distillation rate, it may be impossible to achieve a better efficiency and a more complete purification yield may not be obtained.

In above Preparation Method 1, in the step wherein an acrylate having a hydroxyalkyl group at the α-position is reacted with an unsaturated alcohol, the unsaturated alcohol is added in a dropwise manner. The dropwise addition time may be suitably set depending on the amount of starting material used. For example, this time is set to preferably from 30 minutes to 8 hours, and more preferably from 1 to 4 hours. Following dropwise addition of the unsaturated alcohol, it is preferable to carry out an aging step.

In the above reaction step, the amount of unsaturated alcohol used (total amount) is preferably from 0.1 to 10 moles, and more preferably from 1 to 5 moles, per mole of the acrylate having a hydroxyalkyl group at the α-position.

The reaction temperature is preferably from 10 to 150° C.

Preparation Method 2

The second preparation method of the invention (referred to below as "Preparation Method 2") is a method for preparing a composition containing an α-(unsaturated alkoxyalkyl)acrylate represented by above general formula (1). This method for producing an α-(unsaturated alkoxyalkyl)acrylate composition includes a steps of purifying crude α-(unsaturated alkoxyalkyl)acrylate to obtain purified α-(unsaturated alkoxyalkyl)acrylate, and then adding an antioxidant to the purified α-(unsaturated alkoxyalkyl)acrylate. The α-(unsaturated alkoxyalkyl)acrylate composition obtained by such a preparation method is preferably the above-described α-(unsaturated alkoxyalkyl)acrylate composition of the present invention.

Above Preparation Method 2 preferably further includes the step of reacting an acrylate having a hydroxyalkyl group at the α-position with an unsaturated alcohol represented by above general formula (7).

In the step of adding an antioxidant to the purified α-(unsaturated alkoxyalkyl)acrylate, adding the antioxidant as soon as possible following the purification step is preferable for suppressing an increase in the amount of peroxide.

As mentioned above, the antioxidant added may be of one type, or may be of two or more types. Addition may be carried out all at once, successively or continuously.

Preparation Method 3

The third preparation method of the invention (referred to below as "Preparation Method 3") is a method for preparing an α-(alkoxyalkyl)acrylate, which method includes the steps of, in order, reacting an acrylate having a hydroxyalkyl group at the α-position with an unsaturated alcohol represented by above general formula (7) to obtain a crude α-(unsaturated alkoxyalkyl)acrylate composition which contains the acrylate having a hydroxyalkyl group at the α-position, and treating the crude composition with an inorganic alkali. By thus using an inorganic alkali to treat the crude composition (i.e., the crude α-(alkoxyalkyl)acrylate composition containing an acrylate having a hydroxyalkyl group at the α-position) obtained by the reaction, it is possible to fully remove, from the crude composition, acrylate having a hydroxyalkyl group at the α-position. Hence, with a method of preparation that includes such a treatment step, it is possible to industrially obtain, in an easy and efficient manner, high-purity α-(alkoxyalkyl)acrylate. Such a method of preparation can be advantageously used particularly in methods of preparing α-(unsaturated alkoxyalkyl)acrylates in which an acrylate having a hydroxyalkyl group at the α-position is used in the reaction. In such cases, the effect of being able to industrially produce high-purity α-(unsaturated alkoxyalkyl)acrylate with ease is more clearly achieved. That is, above Preparation Method 3 achieves desirable effects particularly in methods of preparing α-(unsaturated alkoxyalkyl)acrylates having an unsaturated bond-containing organic group at the α-position and in purification methods. Hence, such a Preparation Method 3 is a highly industrially significant technology that enables α-(unsaturated alkoxyalkyl)acrylates, distinctive monomers which have not hitherto been investigated, to be easily and efficiently obtained in a high purity by using conventional industrial purification techniques.

The above Preparation Method 3 is able, in a method for obtaining α-(alkoxyalkyl)acrylate by using in the reaction an acrylate having a hydroxyalkyl group at the α-position, to industrially obtain high-purity α-(alkoxyalkyl)acrylate easily and efficiently by treating the crude composition with an alkali and thereby removing the acrylate having a hydroxyalkyl group at the α-position. This is thought to take place via the following mechanism.

FIG. 1 is a diagram showing what is presumed to be the difference in reactivity between methyl α-(hydroxymethyl)acrylate, which is one type of acrylate having a hydroxyalkyl group at the α-position, and methyl α-(allyloxymethyl)acrylate, which is one type of α-(alkoxyalkyl)acrylate obtained using the former in the reaction.

When methyl α-(hydroxymethyl)acrylate is used in the reaction, because all the methyl α-(hydroxymethyl)acrylate used in the reaction is not converted to the target product, methyl α-(hydroxymethyl)acrylate and the target substance methyl α-(allyloxymethyl)acrylate are both present in the reaction product (crude composition) obtained from this reaction.

In methyl α-(hydroxymethyl)acrylate, because the oxygen atom of the carbonyl group and the hydrogen atom of the hydroxyl group coordinate by hydrogen bonding, the nucleophilicity of the carbon atom (carbonyl carbon) on the carbonyl group in the methyl α-(hydroxymethyl)acrylate rises, increasing the reactivity with alkali. By contrast, in methyl α-(allyloxymethyl)acrylate, hydrogen bonding does not arise and the reactivity with alkali is not particularly enhanced. Hence, methyl α-(hydroxymethyl)acrylate reacts selectively with the alkali and is hydrolyzed. Because the solubility of methyl α-(hydroxymethyl)acrylate in water increases and transfer to the aqueous phase occurs when oil-water separation is carried out, separation becomes easy, as a result of which, presumably, high-purity methyl α-(allyloxymethyl) acrylate can be carried out.

The above mechanism may be regarded as a phenomenon characteristic to cases in which an acrylate having a hydroxyalkyl group at the α-position is used in a reaction to obtain an α-(alkoxyalkyl)acrylate. It is presumed that high-purity α-(alkoxyalkyl)acrylate can be easily obtained via a similar mechanism in cases where another acrylate having a hydroxyalkyl group at the α-position is used or in cases where another α-(alkoxyalkyl)acrylate is obtained.

In Preparation Method 3, the α-(alkoxyalkyl)acrylate obtained as the product has a structure in which an alkoxyalkyl group is bonded to the α-position carbon atom on the double bond in the acrylate. A $C_{1-10}$ alkoxy group is preferred as the alkoxy group on the alkoxyalkyl group, and the alkyl group of the acrylate having a hydroxyalkyl group at the α-position (α-(hydroxyalkyl)acrylate) which serves as the starting material is preferred as the alkyl group on the alkoxyalkyl group. The alkoxy groups may each have a substituent, which substituent may be a cyclic alkyl group or an aryl group.

Illustrative examples of the alkoxy group include acyclic saturated alkoxy groups such as methoxy, ethoxy, n-propoxy, i-propoxy, n-butoxy, t-butoxy, n-amyloxy, s-amyloxy, t-amyloxy, n-hexyloxy, s-hexyloxy, n-heptyloxy, n-octyloxy, s-octyloxy, t-octyloxy, 2-ethylhexyloxy, capryloxy, nonyloxy and decyloxy; alicyclic alkoxy groups such as cyclopentyloxy, cyclohexyloxy, 4-methylcyclohexyloxy, 4-t-butylcyclohexyloxy, tricyclodecanyloxy, isobornyloxy, adamantyloxy, dicyclopentanyloxy, dicyclopentenyloxy and tetrahydrofurfuryloxy; and unsaturated alkoxy groups such as vinyloxy, allyloxy, methallyloxy, crotyloxy and propargyloxy.

From the standpoint of more readily achieving the effects of the invention, compounds which are especially preferred as the above α-(alkoxyalkyl)acrylate are α-(unsaturated alkoxyalkyl)acrylates having a structure in which an alkoxyalkyl group having an unsaturated bond is bonded to the α-position carbon atom composing the double bond in acrylate. In this case, the boiling point difference between the acrylate having a hydroxyalkyl group at the α-position which is used in the reaction and the α-(unsaturated alkoxyalkyl)acrylate obtained as the product is very small, making separation by an ordinary distillation and purification process difficult. However, because separation that is industrially easy and efficient is possible via the preparation method of the invention, the effects of the invention are more clearly achieved. Hence, it is preferable for the above preparation method to be a method of preparing an α-(unsaturated alkoxyalkyl)acrylate or a method of preparing a composition containing an α-(unsaturated alkoxyalkyl)acrylate. The preparation method is more preferably a method of preparing an α-(unsaturated alkoxyalkyl)acrylate represented by above general formula (1), or a method of preparing a composition containing an α-(unsaturated alkoxyalkyl)acrylate represented by above general formula (1). An α-(allyloxymethyl)acrylate is more preferred as the α-(unsaturated alkoxyalkyl)acrylate.

Details and preferred forms of the α-(unsaturated alkoxyalkyl)acrylate represented by above general formula (1) and of the α-(allyloxymethyl)acrylate are as mentioned above.

In other words, above Preparation Method 3 is a method of preparing an α-(alkoxyalkyl)acrylate using as the starting material and/or intermediate an acrylate having a hydroxyalkyl group at the α-position.

In Preparation Method 3, synthesis is carried out using an acrylate having a hydroxyalkyl group at the α-position as the starting material, or synthesis is carried out by using another starting material to form an acrylate having a hydroxyalkyl group at the α-position as the intermediate. Alternatively, synthesis is carried out by a combination thereof.

In Preparation Method 3, "using in the reaction an acrylate having a hydroxyalkyl group at the α-position" means, in the synthesis of an α-(alkoxyalkyl)acrylate, to pass through an acrylate having a hydroxyalkyl group at the α-position, signifying that the invention is applied to methods of preparation via such an acrylate having a hydroxyalkyl group at the α-position. In the preparation of an α-(alkoxyalkyl)acrylate, a method which passes through an acrylate having a hydroxyalkyl group at the α-position is industrially useful, but this invention also strives to resolve purification-related problems that arise at that time.

In a preferred embodiment of Preparation Method 3, an acrylate having a hydroxyalkyl group at the α-position is reacted with an alcohol to obtain an α-(alkoxyalkyl)acrylate. That is, the above "embodiment using in the reaction an acrylate having a hydroxyalkyl group at the α-position" is preferably a step in which an acrylate having a hydroxyalkyl group at the α-position is reacted with an alcohol. A step in which an acrylate having a hydroxyalkyl group at the α-position is reacted with an alcohol having an unsaturated group is more preferred. In this case, an α-(unsaturated alkoxyalkyl) acrylate can be obtained. A step in which an acrylate having a hydroxyalkyl group at the α-position is reacted with an unsaturated alcohol of above general formula (7) is even more preferred.

Preferred embodiments of the reaction step between an acrylate having a hydroxyalkyl group at the α-position and an unsaturated alcohol of general formula (7) are as described above. In the above reaction step, the above-mentioned unsaturated alcohol may be added in a dropwise manner. That is, embodiments which combine the above Preparation Method 1 and Preparation Method 3 are also preferred embodiments. Embodiments which combine above Preparation Method 1 and/or 2 with Preparation Method 3 are preferred embodiments as well.

Above Preparation Method 3, by using an inorganic alkali to treat the crude α-(alkoxyalkyl)acrylate composition which has been obtained by reaction using an acrylate having a hydroxyalkyl group at the α-position and which contains an acrylate having a hydroxyalkyl group at the α-position, carries out the operation of removing the acrylate having a hydroxyalkyl group at the α-position. That is, the above preparation method includes the step of removing the acrylate having a hydroxyalkyl group at the α-position with an alkali including an inorganic alkali. In other words, the above preparation method may be said to include the step of treating unreacted starting material and/or unreacted intermediate using an inorganic alkali. The above preparation method may also be said to be a purification method which includes, in a reaction to obtain an α-(alkoxyalkyl)acrylate using an acrylate having a hydroxyalkyl group at the α-position as the starting material and/or intermediate, the step of using an inorganic alkali to treat and remove unreacted starting material and/or unreacted intermediate.

Here, "crude α-(alkoxyalkyl)acrylate composition" refers to a product which contains both the acrylate having a hydroxyalkyl group at the α-position obtained by the above reaction and the α-(alkoxyalkyl)acrylate serving as the target product. This crude composition is preferably a reaction solution obtained by the reaction; that is, a solution obtained by an α-(alkoxyalkyl)acrylate synthesizing reaction.

The content of acrylate having a hydroxyalkyl group at the α-position in the crude composition is not subject to any particular limitation, but is generally at least 3 wt % per 100 wt % of the α-(alkoxyalkyl)acrylate. Judging from the effects achieved by the invention, the upper limit in the content, although not subject to any particular limitation, is preferably 30 wt % or less.

In cases where preparation is carried out by synthesizing an α-(alkoxyalkyl)acrylate by way of an acrylate having a hydroxyalkyl group at the α-position, it is substantially impossible to completely convert, in an industrial production step, the acrylate having a hydroxyalkyl group at the α-position in the reaction solution obtained from the reaction. That is, all of the acrylate having a hydroxyalkyl group at the α-position used in the reaction is not converted to α-(alkoxyalkyl)acrylate. Hence, because acrylate having a hydroxyalkyl group at the α-position remains in the reaction solution obtained following synthesis of the α-(alkoxyalkyl)acrylate, a purification step for removing this acrylate is carried out. In this purification step, it is generally preferable for operations to be carried out so as to remove also impurities such as catalyst and by-products.

At this time, in the preparation method of the invention, the crude composition (reaction solution) obtained by the reaction is treated using an inorganic alkyl. The effects of the invention are most clearly achieved in cases where an α-(hydroxymethyl)acrylate is used as the acrylate having a hydroxyalkyl group at the α-position.

The above alkali treatment step is a step which carries out the operation of removing acrylate having a hydroxyalkyl group at the α-position from the crude composition by treating the crude composition using an inorganic alkali. This step is preferably one in which, after adding an inorganic alkali-containing alkali to the above crude product, oil-water separation is carried out and the aqueous phase portion is removed. The acrylate having a hydroxyalkyl group at the α-position in the crude product and the α-(alkoxyalkyl)acrylate (particularly the α-(unsaturated alkoxyalkyl)acrylate) have substantially no boiling point difference, making separation by a conventional purification techniques difficult. However, by adding an alkali, as explained above, owing to differences in reactivity with the alkali, the acrylate having a hydroxyalkyl group at the α-position reacts selectively with the alkali and is hydrolyzed. As a result, the acrylate having a hydroxyalkyl group at the α-position has an increased solubility in water, and moves into the aqueous phase when oil-water separation is carried out. This enables high-purity α-(alkoxyalkyl)acrylate to be obtained by the simple operation of oil-water separation.

Depending on the intended use, in order to obtain an α-(alkoxyalkyl)acrylate of even higher purity, following the treatment step using an inorganic alkali to remove the acrylate having a hydroxyalkyl group at the α-position, purification by distillation may be carried out. The effects of the invention are most clearly achieved in cases where the α-(hydroxyalkyl) acrylate serving as the starting material and the α-(alkoxyalkyl)acrylate serving as the product have a small boiling point difference therebetween. Even in cases where the boiling point difference is large, because treatment with an alkali containing an inorganic alkali enables purification by distillation to be simplified, the advantageous effects of the invention can be achieved. A preparation method which obtains an even higher purity α-(alkoxyalkyl)acrylate by thus carrying out purification by distillation following alkali treatment is also a preferred embodiment of the invention.

The above inorganic alkali is an alkali that is an inorganic compound. Because inorganic alkalis have a high reactivity with acrylates having a hydroxyalkyl group at the α-position, it is possible to fully remove the acrylate having a hydroxyalkyl group at the α-position. One, two or more inorganic alkalis may be used. Moreover, one, two or more alkalis which are organic compounds (organic alkalis) may be concomitantly used. Here, the inorganic alkali accounts for preferably at least 70 wt %, more preferably at least 80 wt %, even more preferably at least 90 wt %, and most preferably 100 wt %, of the total amount (100 wt %) of alkali used. The above alkali may be used in the form of an aqueous solution, in which case the concentration is not subject to any particular limitation.

Exemplary inorganic alkalis include the hydroxides, carbonates and bicarbonates of metals such as alkali metals, alkaline earth metals and transition metals. Exemplary organic alkalis include ammonias and amines. Suitable use may be made of alkalis that range from strong alkalis to weak alkalis. More preferred inorganic alkalis include the hydroxides, carbonates and bicarbonates of alkali metals.

In the invention, where necessary, selective use may be made of strong alkalis and weak alkalis, or these may be used in combination. It is also preferable to suitably set the amount of addition according to the strength of the alkali, or to carry out treatment two or more times. For example, in cases where a strong alkali (e.g., a metal hydroxide) is used, if the amount of addition is too large, there is a possibility that the α-(alkoxyalkyl)acrylate which has formed will decompose. By contrast, when a weak alkali (e.g., a metal carbonate or bicarbonate, or an organic alkali) is used, decomposition does not readily occur even with a large amount of addition; hence, the amount of addition may be set in accordance with the strength of such alkalis. Alternatively, two or more treatments involving the addition of a small amount of strong alkali may be carried out in order to efficiently increase the purity while suppressing decomposition. Or a strong alkali and a weak alkali may be used in combination by carrying out treatment with a strong alkali, and subsequently, when the amount of acrylate having a hydroxyalkyl group at the α-position has decreased to a certain degree, carrying out treatment with a weak alkali.

As described above, the amount of the alkali used is suitably set according to the strength of the alkali. For example, it is preferable to set the total amount of alkali used per mole of the acrylate having a hydroxyalkyl group at the α-position in the crude composition to from 0.3 to 10 moles. At less than 0.3 mole, it may not be possible to sufficiently remove the acrylate having a hydroxyalkyl group at the α-position, whereas at more than 10 moles, decomposition of the α-(alkoxyalkyl)acrylate serving as the product may proceed. The amount of alkali added is more preferably at least 0.5 mole, and even more preferably at least 0.6 mole, and is more preferably 8 moles or less, and even more preferably 5 moles or less.

Particularly in cases where a strong alkali is used as the above alkali, the amount of alkali used per treatment is set to preferably 3 moles or less, and more preferably 2 moles or less. Moreover, in cases where a strong alkali is used, it is preferable to set the number of treatments to two or more, and to have the amount of alkali used in each treatment step be small. In this way, it is possible to obtain an α-(alkoxyalkyl) acrylate having a higher purity while fully suppressing decomposition of the product.

In cases where a treatment step with an alkali is carried out two or more times, a different alkali may be used in the respective treatment steps or the same alkali may be used, although it is preferable to include at least a step in which treatment with a strong alkali is carried out. If the number of treatments with an alkali is too high, the production steps become cumbersome; hence, it is preferable for the total number of treatments to be four or less.

In the treatment steps with the above alkali, the crude composition is reacted with the alkali, following which oil-water separation is carried out and the aqueous phase is removed. The specific procedure may be the same as that carried out in conventional industrial production, and is not subject to any particular limitation. In the present invention, by reacting the crude composition with an alkali in this way, the acrylate having a hydroxyalkyl group at the α-position is selectively hydrolyzed, enabling the acrylate and the α-(alkoxyalkyl)acrylate product to be easily separated by the simple operation of ordinary oil-water separation.

Preparation Method 3 is also suitable as a method for obtaining the above described α-(unsaturated alkoxyalkyl) acrylate composition of the invention. That is, it is a method for preparing a composition containing both an α-(unsaturated alkoxyalkyl)acrylate represented by above general formula (1) and also from 0.03 to 0.5 wt % of antioxidant per 100 wt % of the α-(unsaturated alkoxyalkyl)acrylate. This preparation method, which is a method for preparing an α-(unsaturated alkoxyalkyl)acrylate composition that includes the step of reacting an acrylate having a hydroxyalkyl group at the α-position with an unsaturated alcohol represented by above general formula (7) to obtain a crude, α-(unsaturated alkoxyalkyl)acrylate composition which contains the acrylate having a hydroxyalkyl group at the α-position; and a step of treating the crude α-(unsaturated alkoxyalkyl)acrylate composition with an inorganic alkali, is also one aspect of the present invention. Such a preparation method preferably includes as well the step of adding an antioxidant.

Preparation Method 4

The fourth method of preparation of the invention (referred to below as "Preparation Method 4") is a method for preparing an α-(unsaturated alkoxyalkyl)acrylate which includes the step of reacting an acrylate having a hydroxyalkyl group at the α-position with an unsaturated alcohol of general formula (7) to obtain a crude α-(unsaturated alkoxyalkyl)acrylate composition which contains the acrylate having a hydroxyalkyl group at the α-position (which reaction solution is also referred to as "the crude α-(unsaturated alkoxyalkyl)acrylate composition"), and a step of derivatizing the acrylate having a hydroxyalkyl group at the α-position in the composition and carrying out distillation. A monofunctional α-(unsaturated alkoxyalkyl)acrylate is particularly useful in Preparation Method 4. By converting (derivatizing) to another compound the acrylate having a hydroxyalkyl group at the α-position which remains in the reaction solution and carrying out distillation, it is possible to separate the acrylate having a hydroxyalkyl group at the α-position within the reaction solution and the α-(unsaturated alkoxyalkyl)acrylate which is the target product, and thereby increase the purity of the target product. With such a preparation method, the industrially and technically significant and outstanding effect of being able to obtain an α-(unsaturated alkoxyalkyl)acrylate as a highly purified starting monomer for cyclopolymerization using an ordinary industrial purification technique can be achieved.

In above Preparation Method 4, the α-(unsaturated alkoxyalkyl)acrylate serving as the product is an α-(unsaturated alkoxyalkyl)acrylate with a structure in which an alkoxyalkyl group having an unsaturated bond is bonded to the carbon atom at the α-position of the double bond in the acrylate. As explained above, the boiling point difference between the acrylate having a hydroxyalkyl group at the α-position used in the reaction and the α-(unsaturated alkoxyalkyl)acrylate serving as the product is very small, making separation by ordinary distillation and purification difficult. However, with above Preparation Method 4, because industrial separation that is both easy and efficient is possible, the effects of the invention are more clearly achieved. Moreover, it is preferable for the above preparation method to be a method of preparing a composition containing an α-(unsaturated alkoxyalkyl)acrylate, and even more preferable for the preparation method to be a method of preparing an α-(unsaturated alkoxyalkyl)acrylate represented by above general formula (1) or a method of preparing a composition containing an α-(unsaturated alkoxyalkyl)acrylate of general formula (1). The α-(unsaturated alkoxyalkyl)acrylate is more preferably an α-(allyloxymethyl)acrylate.

Details and preferred embodiments of the α-(unsaturated alkoxyalkyl)acrylate of general formula (1) and the α-(allyloxymethyl)acrylate are as described above.

In Preparation Method 4, details of embodiments which use an acrylate having a hydroxyalkyl group at the α-position in the reaction and preferred embodiments thereof are the same as the embodiments described with regard to Preparation Method 3. Moreover, an embodiment in which at least one selected from the group consisting of above-described Preparation Method 1, Preparation Method 2 and Preparation Method 3 is combined with Preparation Method 4 is also a preferred embodiment.

Preparation Method 4 includes also the step of derivatizing the acrylate having a hydroxyalkyl group at the α-position in the reaction solution obtained in the reaction, and carrying out distillation. "The reaction solution obtained in the reaction" refers herein to the solution obtained by the reaction in which the α-(unsaturated alkoxyalkyl)acrylate is synthesized (post-reaction solution).

As described above, in cases where preparation involves synthesizing an α-(unsaturated alkoxyalkyl)acrylate via an acrylate having a hydroxyalkyl group at the α-position, because acrylate having a hydroxyalkyl group at the α-position remains in the reaction solution (crude α-(alkoxyalkyl)acrylate composition) obtained following synthesis of the α-(unsaturated alkoxyalkyl)acrylate, a purification step for removing the acrylate having a hydroxyalkyl group at this α-position is carried out. In this purification step, an operation to remove impurities such as catalyst and by-products is generally carried out.

At this time, in above Preparation Method 4, the acrylate having a hydroxyalkyl group at the α-position which is present in the reaction solution obtained from the reaction is derivatized, and distillation is carried out. The effects of the invention are clearly achieved in cases where α-(hydroxymethyl)acrylate is used as the acrylate having a hydroxyalkyl group at the α-position.

In other words, the above preparation method includes the step of derivatizing unreacted starting material and/or unreacted intermediate, and carrying out distillation.

When thus derivatizing an acrylate having a hydroxyalkyl group at the α-position, it is preferable to carry out derivatization using a derivatizing agent. In such derivatization, of the hydroxyl group, carboxylic acid ester moiety (—COOR) and double bond moiety included as functional groups on the acrylate having a hydroxyalkyl group at the α-position, carrying out the addition reaction of a compound which is a derivatizing agent at the hydroxyl group is preferred. This is both because reaction with the hydroxyl group is easy and also because, in cases where an attempt is made to derivatize the carboxylic acid ester moiety (—COOR) or the double bond moiety, given that these moieties are present also in the α-(unsaturated alkoxyalkyl)acrylate obtained as the product, derivatizing only the acrylate having a hydroxyalkyl group at the α-position from among the product obtained by the reaction is difficult. R in the above formula is a monovalent organic group that is a constituent of the ester group; preferred embodiments of R are mentioned subsequently.

Therefore, the derivatizing agent may be suitably selected from among compounds which react with the hydroxyl group on an acrylate having a hydroxyalkyl group at the α-position, although it is preferable to select a compound which enables the boiling point difference between the derivative of an acrylate having a hydroxyalkyl group at the α-position and the α-(unsaturated alkoxyalkyl)acrylate that is the target product to be made large enough to enable sufficient fractionation when carrying out distillation and purification.

In cases where the hydroxyl group of an acrylate having a hydroxyalkyl group at the α-position is reacted with a derivatizing agent to form an acrylate derivative having a hydroxyalkyl group at the α-position, a reaction temperature, a reaction time, and an amount of derivatizing agent relative to the amount of acrylate having a hydroxyalkyl group at the α-position or the amount of hydroxyl groups present in the reaction mixture which are able in such a reaction to lower the amount of acrylate having a hydroxyalkyl group at the α-position may be suitably selected as the derivatizing conditions. In cases where using a catalyst for reacting the hydroxyl group with the derivatizing agent is effective for promoting the reaction, derivatization using a catalyst is preferred. The catalyst used here can be thoroughly removed by subsequent purification steps such as rinsing with water and distillation.

With regard to the amount of decrease in the acrylate having a hydroxyalkyl group at the α-position during derivatization, letting the amount of acrylate having a hydroxyalkyl group at the α-position after reaction completion and prior to derivatizing treatment be 100 wt %, the weight ratio of acrylate having a hydroxyalkyl group at the α-position following derivatizing treatment (residual ratio) may be set to, for example, from 0.001 to 50 wt %. The weight ratio of acrylate having a hydroxyalkyl group at the α-position following derivatizing treatment (residual ratio) is more preferably from 0.01 to 40 wt %, and even more preferably from 0.1 to 30 wt %.

The distillation step in above Preparation Method 4 should be a step which carries out a distillation method capable of being used in the technical field of the invention following the above derivatizing treatment. The distillation conditions may be suitably selected in such a way that the derivative obtained by derivatization of the acrylate having a hydroxyalkyl group at the α-position within the above reaction solution is fully removed.

In addition, it is preferable for impurities such as catalysts and by-products to be fully removed. A distillation solvent or an azeotropic solvent may also be used. In distillation and purification, it is possible either to have substances other than the target product distilled off, or instead to have the target product distilled off.

With regard to the distillation conditions, distillation is carried out at normal pressure or under reduced pressure, although it is generally preferable to carry out distillation under a reduced pressure. The reduced-pressure conditions are an upper limit of preferably 30 kPa or less, and more preferably 10 kPa or less, and a lower limit of preferably at least 0.01 kPa, and more preferably at least 0.1 kPa. The distillation temperature conditions may be suitably set according to the distillation solvent and the like, although the upper limit is preferably 150° C. or less, and more preferably 120° C. or less. The lower limit is preferably at least 30° C., and more preferably at least 40° C. The distillation step is generally carried out industrially using a distillation column, with the column head temperature preferably being set in such a temperature range.

Moreover, in the above distillation step, a step in which the low-boiling components are distilled off may be carried out beforehand, or a plurality of components having differing boiling points may be sequentially distilled off in stages from the low-boiling components to the high-boiling components. Also, the distillation step may be carried out as part of the purification step. At least one purification method other than distillation, such as washing or extraction, may be carried out before and/or after the distillation step.

In Preparation Method 4, it is preferable for derivatization to be carried out using at least one type of derivatizing agent selected from the group consisting of acid anhydrides, isocyanates, phosphoric acid anhydrides and epoxides.

That is, it is also a preferred embodiment of the invention for the derivatizing step on the acrylate having a hydroxyalkyl group at the α-position to be a step in which the acrylate having a hydroxyalkyl group at the α-position is derivatized using at least one type of derivatizing agent selected from the group consisting of acid anhydrides, isocyanates, phosphoric acid anhydrides and epoxides.

The preferred embodiment in the above derivatization is preferred because of the good reactivity when the acrylate having a hydroxyalkyl group at the α-position within the reaction solution is derivatized, and also because of the good suitability for an industrial process.

Of the foregoing, embodiments in which the derivatizing agent contains an acid anhydride and/or an isocyanate, i.e., embodiments which use, of the derivatizing agents in the above preferred embodiments, an acid anhydride and/or an isocyanate, are especially preferred. Such embodiments are advantageous from the standpoint of the reaction time in derivatization. Moreover, such embodiments are more effective also for lowering the residual ratio of acrylate having a hydroxyalkyl group at the α-position that is present as an unreacted starting material and/or an unreacted intermediate.

In the above preferred embodiments, the acid anhydride group (—CO—O—CO—), isocyanate (NCO) group, phosphoric acid anhydride ($P_4O_{10}$) active site and epoxy group which are the respective reactive groups on the acid anhydrides, isocyanates, phosphoric acid anhydrides and epoxides react with the hydroxyl group on the acrylate having a hydroxyalkyl group at the α-position in the reaction solution. The compound is preferably one in which structural sites other than the reactive group in these compounds either do not react with or have difficulty reacting with the functional group (e.g., double bond, acrylic acid ester site) on the acrylate having a hydroxyalkyl group at the α-position which serves as the starting material and/or the intermediate.

Illustrative examples of acid anhydrides include aliphatic carboxylic anhydrides such as acetic anhydride, adipic anhydride, succinic anhydride, sebacic anhydride, azelaic anhydride, glutaric anhydride, propionic anhydride and maleic anhydride; and aromatic carboxylic anhydrides such as phthalic anhydride, tetrahydrophthalic anhydride, pyromellitic anhydride and benzoic anhydride. Of these, phthalic anhydride and acetic anhydride are especially preferred.

Illustrative examples of the above isocyanates include monofunctional aliphatic isocyanates such as methyl isocyanate, ethyl isocyanate, propyl isocyanate, butyl isocyanate and hexyl isocyanate; monofunctional cyclic isocyanates such as cyclohexyl isocyanate; monofunctional aromatic isocyanates such as phenyl isocyanate; difunctional aromatic isocyanates such as hexamethylene diisocyanate, trimethylhexamethylene diisocyanate and dimer acid diisocyanate; difunctional cyclic isocyanates such as isophorone diisocyanate, dicyclohexylmethane diisocyanate and norbornene diisocyanate; and difunctional aromatic isocyanates such as tolylene diisocyanate, diphenylmethane diisocyanate, naphthalene diisocyanate, tetramethylene xylylene diisocyanate and xylylene diisocyanate. Of these, aromatic isocyanates are preferred. Monofunctional aromatic isocyanates are more preferred, and phenyl isocyanates are even more preferred.

Aside from phosphoric acid anhydride itself ($P_4O_{10}$), the above phosphoric acid anhydrides may include also the related compounds phosphoric acid, phosphorous acid, condensed phosphoric acid, and one, or two or more metal salts thereof, although the content of phosphoric acid anhydride is preferably high. Therefore, it is desirable for the phosphoric acid anhydrides to have a content of phosphoric acid anhydride itself per 100 wt % of the phosphoric acid anhydrides overall of preferably at least 60 wt %, more preferably at least 70 wt %, even more preferably at least 80 wt %, and still more preferably at least 90 wt %. It is most preferable for the phosphoric acid anhydrides to be composed substantially of phosphoric acid anhydride alone. In other words, the higher the phosphoric acid anhydride content, the better.

Preferred epoxides include ethylene oxide, propylene oxide, butylene oxide and cyclohexane oxide. Of these, propylene oxide is especially preferred.

Examples of the derivatization step in the above preferred embodiments are shown in reaction formulas (i) to (iv) below.

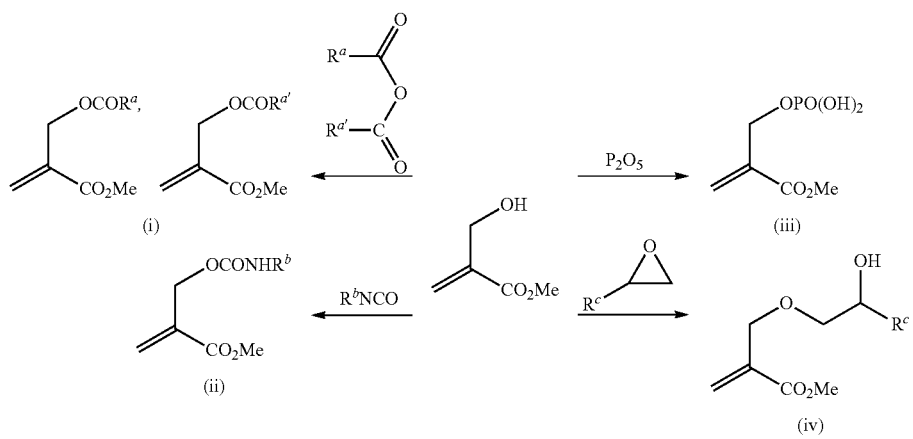

Reaction conditions in the above derivatization step, such as the type and molar ratio of the catalyst and the reaction temperature and time, may be set as appropriate. However, in cases where an α-(hydroxymethyl)acrylate is used as the acrylate having a hydroxyalkyl group at the α-position and allyl alcohol is used as the unsaturated alcohol, the preferred derivatization conditions may be as follows. These derivatization conditions may be employed for any acrylate having a hydroxyalkyl group at the α-position and any unsaturated alcohol, although they are especially preferred in cases where an α-(hydroxymethyl)acrylate and allyl alcohol are used.

In above reaction step (i), the amount of acid anhydride used is preferably from 0.1 to 5.0 equivalents per equivalent of hydroxyl groups in the reaction mixture. The catalyst used is preferably an acid catalyst or an amine catalyst, and the amount of catalyst is preferably from 0.1 to 50 mol % relative to the amount of hydroxyl groups in the reaction mixture. The reaction temperature is preferably from 10 to 80° C., and more preferably from 30 to 70° C. The reaction time may be suitably set according to how the reaction proceeds, although a period of from 0.1 to 8 hours is preferred.

In above reaction step (ii), the amount of isocyanate used is preferably from 0.1 to 5.0 equivalents per equivalent of hydroxyl groups in the reaction mixture. The catalyst used is preferably an acid catalyst or an amine catalyst, and the amount of catalyst is preferably from 0.1 to 50 mol % relative to the amount of hydroxyl groups in the reaction mixture. The reaction temperature is preferably from 10 to 80° C., and more preferably from 30 to 70° C. The reaction time may be suitably set according to how the reaction proceeds, although a period of from 0.1 to 8 hours is preferred.

In above reaction step (iii), the amount of phosphoric acid anhydride used is preferably from 0.1 to 5.0 equivalents per equivalent of hydroxyl groups in the reaction mixture. The catalyst used is preferably an acid catalyst or an amine catalyst, and the amount of catalyst is preferably from 0.1 to 50 mol % relative to the amount of hydroxyl groups in the reaction mixture. The reaction temperature is preferably from 10 to 80° C., and more preferably from 30 to 70° C. The reaction time may be suitably set according to how the reaction proceeds, although a period of from 0.1 to 16 hours is preferred.

In above reaction step (iv), the amount of epoxide used is preferably from 0.1 to 5.0 equivalents per equivalent of hydroxyl groups in the reaction mixture. The catalyst used is preferably an acid catalyst or an amine catalyst, and the amount of catalyst is preferably from 0.1 to 50 mol % relative to the amount of hydroxyl groups in the reaction mixture. The reaction temperature is preferably from 10 to 80° C., and more preferably from 30 to 70° C. The reaction time may be suitably set according to how the reaction proceeds, although a period of from 0.1 to 16 hours is preferred.

Preferred examples of the acid catalyst used in the above derivatizing reaction step include organic acids such as onium salts, sulfone compounds, sulfonic acid ester compounds, sulfonamide compounds, diazomethane compounds, p-toluenesulfonic acid, benzenesulfonic acid and trifluoromethanesulfonic acid; and inorganic acids such as hydrochloric acid, sulfuric acid, nitric acid and phosphoric acid. Of these, inorganic acids are more preferred, and sulfuric acid is even more preferred.

As mentioned above, the amine catalyst used in derivatization is not limited only to tertiary amines; use may also be made of primary and secondary amines and aromatic amines such as pyridines. Because a tertiary amine is generally used in the above α-(unsaturated alkoxyalkyl)acrylate synthesizing reaction, derivatization may be carried out using as the catalyst the amine (tertiary amine) already in the reaction mixture, or derivatization may be carried out after the subsequent addition of amine as the catalyst.

In cases where derivatization is carried out using amine (tertiary amine) in the reaction mixture as the catalyst, the tertiary amine catalyst used in forming the α-(unsaturated alkoxyalkyl)acrylate may also be used in the derivatization step. Preferred examples of tertiary amine catalysts are as mentioned above.

Preparation Method 4 is also preferred as a method for obtaining the above-described α-(unsaturated alkoxyalkyl) acrylate composition of the invention. That is, it is a method of preparing a composition containing an α-(unsaturated alkoxyalkyl)acrylate represented by above general formula (1) and from 0.03 to 0.5 wt % of antioxidant per 100 wt % of the α-(unsaturated alkoxyalkyl)acrylate. Thus, a method for preparing an α-(unsaturated alkoxyalkyl)acrylate composition, which method includes a step of reacting an acrylate having a hydroxyalkyl group at the α-position with an unsaturated alcohol of general formula (7) to obtain a crude α-(unsaturated alkoxyalkyl)acrylate composition which contains the acrylate having a hydroxyalkyl group at the α-position); and a step of derivatizing an acrylate having a hydroxyalkyl group at the α-position in the crude composition obtained in the reaction step and carrying out distillation, is also one aspect of the invention. It is preferable for such a preparation method to include as well the step of adding an antioxidant.

Preferred Uses of α-(Alkoxyalkyl) Acrylate Compositions Polymer

The α-(unsaturated alkoxyalkyl)acrylate composition of the invention, and compositions containing the α-(allyloxyalkyl)acrylate or α-(unsaturated alkoxyalkyl)acrylate obtained by above Preparation Methods 1 to 4, are able to provide polymers having cyclic structures on the main chain, etc. through polymerization involving addition polymerization and simultaneous cyclization as described above. The α-(allyloxymethyl)acrylate polymer thus obtained has a weight-average molecular weight (Mw) which may be suitably selected according to the intended purpose and application. However, when used in liquid applications such as radical curable resin compositions or colorant dispersing compositions, to achieve good flow properties, the weight-average molecular weight is preferably not more than 100000, more preferably not more than 70000, and even more preferably not more than 50000. To fully achieve the properties as a polymer, the weight-average molecular weight is preferably at least 1000, and more preferably at least 3000.

The above α-(allyloxymethyl)acrylate polymer has a polydispersity (Mw/Mn), which expresses the molecular weight distribution, of preferably 5.0 or less, more preferably 4.0 or less, and even more preferably 3.0 or less. In the preparation method of the invention, to suppress branching of the polymer, Mw/Mn may be made small.

The methods of measuring the weight-average molecular weight (Mw) and the polydispersity (Mw/Mn) are not subject to any particular limitation. For example, the measurement methods used in the subsequently described examples may be used.

Reactive Diluent

The applicant has also found that the α-(unsaturated alkoxyalkyl)acrylate of the invention is a radical polymerizable monomer which is particularly useful as a reactive diluent. This radical polymerizable monomer is described below.

The α-(unsaturated alkoxyalkyl)acrylate of the invention is a compound represented by above general formula (1), and is useful as a radical polymerizable monomer.

Of above general formula (1), embodiments in which n is an integer of 2 or more, i.e., embodiments having a functionality of two or more, function also as a crosslinking agent, thus enabling more preferred use in various applications such as the following. Of the compounds of general formula (1), compounds represented by general formula (4) above in which n is an integer of 2 or more, and compounds represented by above general formula (6) are particularly useful as radical polymerizable monomers. Because these compounds cure rapidly, have an excellent surface curability and thin-film curability, do not readily incur the inhibition of polymerization by oxygen, have a higher radical curability than the (meth)acrylic monomers commonly used as reactive diluents and are low-shrinking (have a small cure shrinkage), and moreover because cured forms of such compounds have outstanding adhesive and mechanical properties, they are useful as reactive diluents in various applications, including coating materials, adhesives, sealants, pressure-sensitive adhesives, paints, inks, resists, dental materials, lenses, and molding materials.

The radical-curable composition which contains the above α-(unsaturated alkoxyalkyl)acrylate (radical-polymerizable monomer) are also an aspect of the invention by the present applicant. And, the radical-curable composition containing the above α-(unsaturated alkoxyalkyl)acrylate composition are likewise a further aspect of the invention by the present applicant.

The above radical-polymerizable monomer and a radical-polymerizable monomer curing method which involves curing the radical-polymerizable monomer in the radical curable composition are also further aspects of the invention by the present applicant.

A cured product obtained by curing a radical-polymerizable monomer by the above curing method are a yet further aspect of the invention by the present applicant.

These inventions are described in detail below.

Radical-Polymerizable Monomer

The radical-polymerizable monomer is a compound represented by above general formula (1). Of these, the particularly useful compounds represented by general formula (4) in which n is an integer of 2 or more, and compounds represented by general formula (6) (sometimes referred to below as "AMA monomers") are described. There compounds have a higher radical curability and a smaller shrinkage during curing than (meth)acrylic monomers, and the cured product obtained by curing these compounds have excellent adhesive and mechanical properties. Such characteristics are thought to arise from the polymerizable groups represented by general formula (9) below

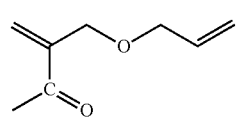

(9)

(structures in which an allyloxymethyl group has been inserted at the α-position of the acryloyl group; sometimes referred to below as the "AMA group").

"Curing" refers to the formation of a high-molecular-weight material by polymerization reaction, such as the formation of a viscous liquid substance useful as a pressure-sensitive adhesive, or the formation of a hard, solid substance useful as a coating material; the notion of "curing" as used herein does not require solidification or the formation of crosslinkages.

As mentioned above, the radical-polymerizable monomer has an excellent radical curability, in addition to which the cured product has excellent adhesive and mechanical properties. This is thought to be a consequence primarily of the distinctive radical polymerizability of the AMA group.

The radical curing mechanism of the AMA group is described below.

It is something of a surprise that the AMA group, in spite of including the allyl ether group which readily gives rise to degradative chain transfer (readily forms allyl radicals) and in spite of the fact that the α-position of the double bond which is conjugated with the carbonyl group is sterically crowded, exhibits a higher radical curability than the (meth)acryloyl group. However, it is conceivable that, because the AMA group does not readily give rise to an allyl radical, a methylene radical which has a high polymerization activity being formed instead as the growth radical, the oxygen curing inhibition observed in conventional (meth)acryloyl group radical addition polymerization does not readily occur. This mechanism is described in detail while referring to the conceptual diagrams shown in FIGS. 2 and 3.

FIG. 2 is a conceptual diagram showing that, in the mechanism of AMA group radical addition polymerization, an allyl radical does not readily form; rather, a methylene radical, which has a high polymerization activity as a growth radical, forms instead. In the AMA group, two types of double bonds ((I) and (II) in FIG. 2) are present. It is thought that the initiation radical or growth end radical (X•) conjugates with the neighboring carbonyl group and selectively attacks the activated double bond (I). If it were to attack (II), an allyl radical would immediately form, resulting in the deactivation of polymerization (degradative chain transfer). The radical that forms when X• attacks (I) is capable of two types of addition polymerization, leading to the formation of mutually differing structures. Pathway (a) is a mechanism in which an intermolecular growth reaction arises following a cyclizing reaction; an allyl radical does not form. Pathway (b) is a mechanism in which an intermolecular growth reaction arises immediately and an allyl ether group remains present; the allyl ether group that remains becomes a cause of degradative chain transfer, i.e., polymerization deactivation. The initial step (cyclizing reaction) of Pathway (a) is an intramolecular reaction, which is much faster than the growth reaction that is an intermolecular reaction. Also, on comparing the growth radicals in the two pathways, the growth radical in Pathway (a) is a methylene radical which is not sterically crowded, and has a higher polymerization activity than the growth radical in Pathway (b) (a sterically crowded tertiary radical having an allyloxymethyl group substituted at the α-position). Hence, although it has two steps, Pathway (a) appears to be better. Thus, in an AMA group radical addition polymerization reaction, because the mechanism that does not form an allyl radical (attack by X• of double bond (I)→Pathway (a) cyclopolymerization) is better, formation of an allyl radical does not readily occur, with a methylene radical having a high polymerization activity instead forming as the growth radical.

FIG. 3 is a conceptual diagram showing that the AMA group does not readily give rise to oxygen curing inhibition. In conventional (meth)acryloyl group radical addition polymerization, a growth radical and an active oxygen react, readily giving rise to a stable radical having no addition polymerization activity. However, in radical addition polymerization on an AMA group, an active oxygen absorbing site other than the growth radical is present; moreover, it appears that, even after conversion to a structure which has absorbed active oxygen, the addition polymerization activity is maintained. For this reason, curing does not appear to be readily inhibited by oxygen.

In the case of an AMA monomer, curing by way of the above mechanism is possible. However, with a low boiling point monomer, there is a tendency for the curability to diminish depending on the conditions (such as, for example, in cases where a thin-film state is formed and curing is carried out in air). This causes problems when using it as a reactive diluents. The reason is not well understood, although when the boiling point is low, the activity of the growth radical becomes too high, which appears to have the opposite effect of lowering the curability due to a mechanism such as the growth radicals, which should react with the unreacted monomer present nearby in a large amount, reacting instead with the active oxygen present in a very small amount, or reacting instead with hydroperoxide structures that have formed at the oxygen absorption site, leading to the termination of polymerization.

In addition, the above radical polymerizable monomer has a smaller shrinkage during curing than the (meth)acrylic monomer. It is thought that this may be due to the fact that the monomer polymerizes while cyclizing, as shown in Pathway (a) of FIG. 2 and the polymerization rate is extremely high. That is, compared with the polymerization of an ordinary (meth)acrylic monomer (the same mechanism as in Pathway (b) of FIG. 2), it is thought that shrinkage may be suppressed because polymerization occurs while giving rise to a bulky cyclic structure.

The cured product obtained by curing the above radical polymerizable monomer has a high adhesion. This is presumably due to, as shown in Pathway (a) in FIG. 2, the tetrahydrofuran ring included in the structure shown in general formula (10) below

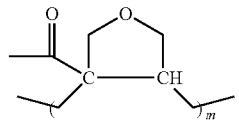

(10)

and the methylene groups adjoining the tetrahydrofuran ring on both sides. The tetrahydrofuran ring acts as a so-called Lewis base (a donor of a lone pair of electrons), facilitating interactions between the tetrahydrofuran ring and functional groups at the substrate surface, which presumably manifest as a good adhesion. The methylene groups adjoining the tetrahydrofuran ring on both sides are thought to increase the flexibility of the polymer chain, giving rise more effectively to the above interactions. In addition, cured product of the above radical polymerizable monomer also have an excellent heat resistance, colorant dispersibility, compatibility and mechanical properties, the appearance of such properties presumably being attributable to the structure shown in general formula (10).

The above radical-polymerizable monomer is preferably one having a boiling point at 1333 Pa of 95° C. or more. This expresses the desirability that the temperature at 1333 Pa on the vapor pressure curve for the above radical polymerizable monomer be at least 95° C. In the above radical-polymerizable monomer, it has been confirmed that a strong correlation exists between the boiling point and the curability; when the boiling point at 1333 Pa is 95° C. or more, an even better curability is achieved. Moreover, by having such a boiling point, the above radical-polymerizable monomer is endowed with an even better curing rate, surface curability and thin-film curability.

That is, radical polymerizable monomers which are represented by above general formula (1) and have a boiling point at 1333 Pa of at least 95° C. are also a preferred embodiment of the invention by the present applicant.

It is another preferred embodiment of the invention for the α-(unsaturated alkoxyalkyl)acrylate in the α-(unsaturated alkoxyalkyl)acrylate composition of the invention to have a boiling point of at least 95° C. at 1333 Pa.

The boiling point at 1333 Pa of the radical polymerizable monomer is more preferably 99° C. or more, and even more preferably 103° C. or more.

The reason for specifying in this way the boiling point of the above radical polymerizable monomer as the boiling point at 1333 Pa is that, because the radical polymerizable monomer has a high reactivity, the boiling point is difficult to measure at normal pressure. However, if the boiling point of the radical polymerizable monomer is to be specified as the boiling point at normal pressure, such specification may be done as follows.

For example, a method of estimating any boiling point from a single measured value has been disclosed (Shuzo Oe: Bussei Suisan-hō [Methods for estimating physical properties] (Databook Shuppan), p. 73; formula (4.32)). Because the radical polymerizable monomer is a polar liquid, estimation may be carried out using the following numerical formula (1).

$$P^{0.105} = 14.1T^{0.105} + C \quad (1)$$

where
P: vapor pressure (mmHg)
T: temperature (K)
C: physical constant

Using above formula (1), the physical constant C is determined from a single measured value, enabling the boiling point at any pressure to be calculated. That is, the boiling point at normal pressure can be calculated from the boiling point of the measured value at 1333 Pa (10 mmHg).

Even when the boiling point at normal pressure determined as described above is less than 205° C., the AMA monomer will cure depending on the conditions, although a boiling point at normal pressure of 205° C. or more is required to obtain a good curability. The boiling point at normal pressure is preferably at least 210° C., and most preferably at least 215° C. Thus, an α-(unsaturated alkoxyalkyl)acrylate of above general formula (1) which has a boiling point at normal pressure, determined as described above, of 205° C. or more can be advantageously used as the reactive diluent.

That is, a radical polymerizable monomer which is a radical polymerizable monomer of above general formula (1) and has a boiling point at 101.3 kPa, as determined using the following numerical formula (1)

$$P^{0.105} = 14.1T^{0.105} + C \quad (1)$$

(where P is the vapor pressure (mmHg), T is the absolute temperature (K), and C is a physical constant), of 205° C. or more is also a preferred embodiment of the invention by the present applicant.

Using the above formula, it is possible to estimate the boiling point at any pressure. For example, in cases where the boiling point at 1333 Pa cannot be measured, but the boiling points at less than 1333 Pa can be measured, it is possible to determine the boiling point at 1333 Pa from the boiling points at below 1333 Pa. However, in the case of high-boiling radical polymerizable monomers, even at a pressure below 1333 Pa, polymerizable may occur before the boiling point is reached. With regard to radical polymerizable monomer boiling points which can actually be measured, for example, at a pressure of 533 Pa that can presumably be attained by an ordinary vacuum unit, the measurable range is thought to be about 110° C. When the vapor phase is at 110° C., the radical polymerizable monomer is heated at or above this temperature; attempts to measure higher boiling points may result in polymerization, making measurement impossible. The boiling point at 1333 Pa and the boiling point at normal pressure of a radical polymerizable monomer having a boiling point at 533 Pa of 110° C., as determined using the above formulas, are respectively 126° C. and 245° C. For example, in boiling point measurement and the distillation step, when trying to obtain an amount of vapor sufficient to enable measurement of the boiling point, in cases where the vapor phase temperature is 110° C., it is thought to be necessary for the radical polymerizable monomer in the liquid phase to be heated to a temperature of at least 130° C. That is, in cases where a sufficient amount of vapor cannot be obtained even with heating to a temperature of 130° C. or more at a pressure of 533 Pa, thus making it impossible to measure the boiling point of radical polymerizable monomer, the boiling point at 1333 Pa may be treated as 126° C. or more and the boiling point at normal pressure may be treated as 245° C. or more.

Thus, the excellent radial curability of the above radical polymerizable monomers appears to originate from the AMA group, and moreover from its boiling point. Also, the low cure shrinkage of the above monomer and the excellent adhesive and mechanical properties of the cured product obtained therefrom appear to be attributable to the tetrahydrofuran ring-containing structure that forms in polymerization of the AMA group. Hence, the above-described monomer of general formula (1) may be used as the radical polymerizable monomer.

Radical Polymerizable Curable Composition

The radical curable composition containing the above radical polymerizable monomer (which composition is also referred to below simply as the "curable composition") may include a radical polymerizable monomer which is copolymerizable with the α-(unsaturated alkoxyalkyl)acrylate of this invention. In addition, aside from the polymerizable monomer, various additives may be included according to the intended purposes and applications. Such additives include, but are not particularly limited to, cure accelerators, other polymerizable monomers, stabilizers, binder resins, solvents, fillers, colorants, dispersants, adhesion enhancers, parting agents, plasticizers, ultraviolet absorbers, delusterants, defoamers, leveling agents, antistatic agents, slip agents, surfactants, silane, aluminum or titanium-based coupling agents, and acid generators. Of these, cure accelerators such as radical polymer initiators, radical polymerization accelerators and light sensitizers are preferred ingredients for addition in order to better elicit the performance of the radical polymerizable monomer.

Major additives are described below.

(A) Radical Polymerization Initiator

The radical polymerizable monomer can be cured by heating and/or exposure of actinic energy radiation such as electromagnetic waves or an electron beam to initiate radical polymerization, although curing may be carried out more effectively with the concomitant use of a radical polymerization initiator. Hence, it is also a preferred embodiment for the radical curing composition to additionally include a radical polymerization initiator.

The radical polymerization initiator may be a thermo-radical polymerization initiator which generates a radical when heated, or a photo-radical polymerization initiator which generates a radical upon exposure of actinic energy radiation. Generally, one, two or more commonly used radical polymerization initiators may be employed. It is desirable to also add one, two or more commonly used radical polymerization accelerators and optical sensitizers, as needed.

Radical polymerization accelerators which may be used together with the above thermo-radical polymerization initiator are agents which promote the decomposition of the thermo-radical polymerization initiator (the generation of initiating radicals). Use may be made of any that is commonly employed.

By using a photosensitizer or a radical polymerization accelerator together with the photo-radical polymerization initiator, the sensitivity and curability can be improved. Commonly employed photosensitizers and radical polymerization accelerators may be used as such photosensitizers and radical polymerization accelerators.

The radical polymerization initiator is not an essential ingredient in the above curable composition; the addition or lack of addition thereof, and the amount of addition if used, may be suitably set according to the intended purposes and applications. In cases where the above radical polymerization initiator is employed, the amount of addition is not subject to any particular limitation, although in terms of the balance among curability, the adverse influence of decomposition products and cost effectiveness, the amount of addition when employing such a radical polymerization initiator is preferably from 0.01 to 30 wt %, more preferably from 0.05 to 20 wt %, and even more preferably from 0.1 to 15 wt %, based on the total weight of the radical polymerizable compounds, including the above radical polymerizable monomer.

In the above curable composition, the radical polymerization accelerator and photosensitizer are not essential ingredients; the addition or lack of addition thereof, and the amount of addition if used, may be suitably set according to the intended purposes and applications. In cases where the above radical polymerization accelerator and photosensitizer are employed, the amounts of addition are not subject to any particular limitations, although in terms of the balance between curability and cost effectiveness, the amount of additions when employing such a radical polymerization accelerator and such a photosensitizer are each preferably from 0.001 to 20 wt %, more preferably from 0.01 to 10 wt %, and even more preferably from 0.05 to 10 wt %, based on the total weight of the radical polymerizable compounds, including the above radical polymerizable monomer.

(B) Cure Accelerators Other than Radical Polymerization Initiators

Cure accelerators other than radical polymerization initiators include polyfunctional thiols. Because polyfunctional thiols are capable of acting as polyfunctional chain transfer agents in radical curing, and are also capable of acting as crosslinking agents based on an ene-thiol reaction mechanism with allyl ether groups, they are able to increase the curability of the curable composition. Such polyfunctional thiols are not subject to any particular limitation, so long as they are compounds having two or more mercapto groups on a single molecule. Illustrative examples include trimethylolpropane tris(3-mercaptopropionate), pentaerythritol tetrakis (3-mercaptopropionate), pentaerythritol tetrakis(3-mercaptobutyrate), dipentaerythritol hexakis(3-mercaptopropionate), 1,4-bis(3-mercaptobutyryloxy)butane, 1,3,5-tris(3-mercaptobutyloxyethyl)-1,3,5-triazine-2,4,6-(1H,3H,5H)-trione. These may be used singly or as combinations of two or more thereof.

(C) Polymerizable Monomers Other Than the Above Radical Polymerizable Monomers

Taking into account the performance balance and cost effectiveness, the curable composition may include polymerizable monomers other than the above radical polymerizable monomers, so long as doing so that does not compromise the outstanding characteristics of the composition. Examples of such other polymerizable monomers include, but are not particularly limited to, compounds having a radical polymerizable group, such as a carbon-carbon unsaturated bond; compounds having a cation polymerizable group, such as an epoxy group, an oxetanyl group or a vinyl ether group; and hybrid compounds having both a radical polymerizable group and a cation polymerizable group. One, two or more of the above may be used, depending on the intended purposes and applications. Radical polymerizable monomers other than the above radical polymerizable monomers which can be cured by the same mechanism as the above radical polymerizable monomers are preferred.

The above other radical polymerizable monomers may be divided into monofunctional radical polymerizable monomers having only one radical polymerizable unsaturated group on the same molecule, and polyfunctional radical polymerizable monomers having two or more such groups on the same molecule.

(D) Binder Resin

The binder resin is an oligomer or polymer which has a filler-type role, such as imparting/enhancing film formability and preventing a loss of shape. Depending on the intended purpose and application, various functions are additionally imparted, such as alkali developability, colorant dispersibility and heat resistance. Such a binder resin may be made of one, or two or more of various oligomers or polymers commonly employed as binder resins, and is not subject to any particular limitation. For example, by using an alkali-soluble oligomer, such as a carboxyl-modified vinyl ester resin or a (meth) acrylic acid copolymer, as the binder resin, the above curable composition can be employed in alkali-developable permanent resist applications such as solder resists, resists for color filters, and protective film resists. Moreover, by using as the binder resin a (meth)acrylic acid ester polymer or other polymer having a suitable glass transition temperature and compatibility with the colorant and dispersant, the curable composition can be employed in paint and ink applications.

(E) Solvent

A solvent is used for such purposes as to lower the viscosity by dilution, to adjust the applied film thickness, and to uniformly mix/disperse various ingredients in the curable composition. Where necessary, a solvent may be included in the curable composition. The solvent may be a low-viscosity organic solvent or water which is capable of dissolving or dispersing the various ingredients in the curable composition. The solvent used is not subject to any particular limitation, and may be one that is commonly employed in curable compositions.

Curing Method

The method of curing the above radical polymerizable monomer or the radical polymerizable monomer in the above radical curable composition is also one aspect of the invention by the present applicant. As already explained, the above radical polymerizable monomer and curable composition undergo curing via addition polymerization by a radical mechanism, and can be cured by heating and/or exposure of actinic energy radiation. Such curing may be effected using only a single such method, or using a combination of two methods. That is, a method of curing a radical polymerizable monomer which entails curing the above radical polymerizable monomer or the radical polymerizable monomer in the above radical curable composition and which includes the step of curing by way of heating and/or exposure of actinic energy radiation is also a preferred embodiment.

The heating conditions, i.e., the curing temperature, in the above curing method via heating may be suitably selected according to the combination of ingredients in the composition. In cases where a cure accelerator is not included, the curing temperature is preferably set to from 30 to 400° C., more preferably from 70 to 350° C., and even more preferably from 100 to 350° C. By setting the temperature to such a level, curing without a cure accelerator can easily be carried out, and thermal degradation due to excessive heating can be reduced. In cases where a cure accelerator is included, curing may be carried out at a lower temperature than when an accelerator is not included, the curing temperature being preferably from 0 to 400° C., more preferably from 10 to 350° C., and even more preferably from 20 to 350° C. Curing by heating may be carried out in two or more stages, or may be carried out before curing by exposure of actinic energy radiation or after such curing. For example, a step referred to as "post-bake" or "post-cure, which enables curing to proceed even further, is preferable in which, after implementing curing to a certain extent by heating at a low temperature or by exposure of actinic energy radiation for a short time, then treatment such as development has been subsequently carried out, curing is induced at an elevated temperature of preferably at least 150° C., more preferably at least 180° C., and even more preferably at least 200° C."

In the curing method involving exposure of actinic energy radiation, the actinic energy radiation used may be any that is commonly employed. Illustrative examples include electromagnetic waves such as gamma rays, x-rays, ultraviolet light, visible light and infrared light; and particle beams such as electron beams, neutron beams and proton beams. Of these, from the standpoint of the energy intensity and the energy radiation generators, gamma rays, x-rays, ultraviolet light, visible light and electron beams are preferred; ultraviolet light, visible light and electron beams are more preferred; and ultraviolet light is most preferred. In cases where a cure accelerator is not included, the use of intense actinic energy radiation such as gamma rays, x-rays and electron beams is preferred. In cases where a cure accelerator is included, preferred use can be made of actinic energy radiation which has a relatively weak energy but is easy and inexpensive to generate, such as ultraviolet light and visible light.

Cured Product

The cured product obtained by using the foregoing curing method to cure the above-described radical polymerizable monomer or the above-described radical polymerizable monomer-containing curable composition is also one aspect of the invention by the present applicant. That is, the cured product which contains the above ingredients other than the radical polymerizable monomer and is obtained by curing is also an aspect of the invention. As mentioned in the above "Curable Composition" section, examples of ingredients other than the above-described radical polymerizable monomer include radical initiators, other radical polymerizable monomers, stabilizers and solvents. Therefore, the cured product may be in a state that includes solvent, or may be rendered into a state containing substantially no solvent by drying via a step in which solvent is removed from such a cured product. As mentioned earlier, the cured product includes the structure shown in above general formula (10), and is thereby able to exhibit advantageous actions and effects in terms of curability and adhesive and mechanical properties. Moreover, it also has an excellent heat resistance, colorant dispersibility and compatibility.

With regard to the curability, as shown in the above-described curing mechanism, basically, the properties due to curing reactions involving radicals are excellent. For the radical curability to be excellent means that the curing properties due to radicals generated by heating and/or exposure of actinic energy radiation are excellent.

With regard to the adhesive and mechanical properties of the cured product, these are properties which are presumably exhibited due to the recurring unit structure (structures having methylene groups adjoining the tetrahydrofuran ring on both sides) that arise primarily from the radical curing mechanism. For the adhesive properties to be excellent means that the cured product obtained by the above-described curing method adheres well to a substrate (e.g., glass, resin, metal) and is difficult to separate therefrom. For the mechanical properties to be excellent means that the cured product obtained by the above-described curing method has a high toughness (is hard and tenacious).

With regard to the curability, in cases where a radical polymerizable monomer or radical curable composition is applied onto a substrate and irradiated with UV light, when the UV irradiation time required for the surface to cure is measured, a shorter irradiation time indicates a better radical curability (in this case, a better UV curability). With regard to the cure shrinkage, in cases where a radical polymerizable monomer or a radical curable composition is applied onto a substrate and irradiated with UV light, when the shrinkage after curing is measured, a smaller shrinkage means that shrinkage due to curing arises with greater difficulty, indicating a better cure performance.

The adhesive properties of the cured product may be expressed as the proportion of squares that remain adhering in a crosscut adhesion test, or the tensile strength required to separate two substrates laminated together by means of the cured product. The higher these values, the better the adhesive properties.

The mechanical properties of the cured product may be expressed in terms of the energy and elongation at break and the modulus of elasticity. When these values are high, this indicates a higher tenacity, meaning that the cured product is harder and more tenacious.

Characteristics such as the above curability, adhesion and mechanical properties may take on various values depending on the curing conditions and measurement conditions which can be variously set according to the intended applications. When evaluating a radical polymerizable monomer or a radical curable composition, the performance thereof may be understood by applying, for example, the conditions in subsequently described Evaluation Example 11 and thereafter, and by comparison therewith. The above radical polymerizable monomer, radical curable composition and curing methods thereof are able, in the respective performances thereof, to exhibit characteristics attributable to the boiling point of the radical polymerizable monomer and the AMA group in the monomer, and thus can be advantageously employed in various applications, particularly in reactive diluent applications. For example, the above characteristics such as curability, adhesion and mechanical properties are desired in various technical fields and applications, including coating materials, adhesives, sealants, pressure-sensitive adhesives, paints, inks, resists, dental materials, lenses and molding materials. If these characteristics can be enhanced, the achievement of outstanding actions and effects in these technical fields will be recognized and appreciated. Accordingly, the above-described radical polymerizable monomers, radical curable compositions and curing methods endowed with the above-described excellent characteristics can be advantageously employed in various technical fields and applications, enabling outstanding actions and effects to be achieved.

The α-(unsaturated alkoxyalkyl)acrylate compositions of the invention are stabilized compositions which enable α-(unsaturated alkoxyalkyl)acrylate (e.g., α-(allyloxymethyl)acrylate) products to be stored at a high purity for an extended period of time, and fully suppress problems such as coloration and gelation from arising during polymerization. Moreover, the inventive methods of preparing α-(unsaturated alkoxyalkyl)acrylate compositions exhibit the outstanding effect of enabling high-purity α-(unsaturated alkoxyalkyl) acrylates such as α-(allyloxymethyl)acrylate to be industrially obtained in a safe manner. Finally, the α-(unsaturated alkoxyalkyl)acrylates of the invention are useful as reactive diluents or monomer components in curable compositions.

BRIEF DESCRIPTION OF THE DRAWINGS

FIG. 1 is a diagram showing what is presumed to be the difference in reactivity between methyl α-(hydroxymethyl) acrylate (one type of acrylate having a hydroxyalkyl group at the α-position) and the methyl α-(allyloxymethyl)acrylate (one type of α-(alkoxyalkyl)acrylate) obtained by using the former in a reaction.

FIG. 2 is a conceptual diagram showing that, in the radical addition polymerization mechanism involving an AMA group, an allyl radical does not readily form; instead, a methylene radical having a high polymerization activity forms as the growth radical.

FIG. 3 is a conceptual diagram showing that an AMA group does not readily give rise to oxygen curing inhibition.

FIG. 10 is a diagram showing the $^1$H-NMR chart and assignments for α-(unsaturated alkoxyalkyl)acrylate in Example 24.

BEST MODES FOR CARRYING OUT THE INVENTION

Figure 4:
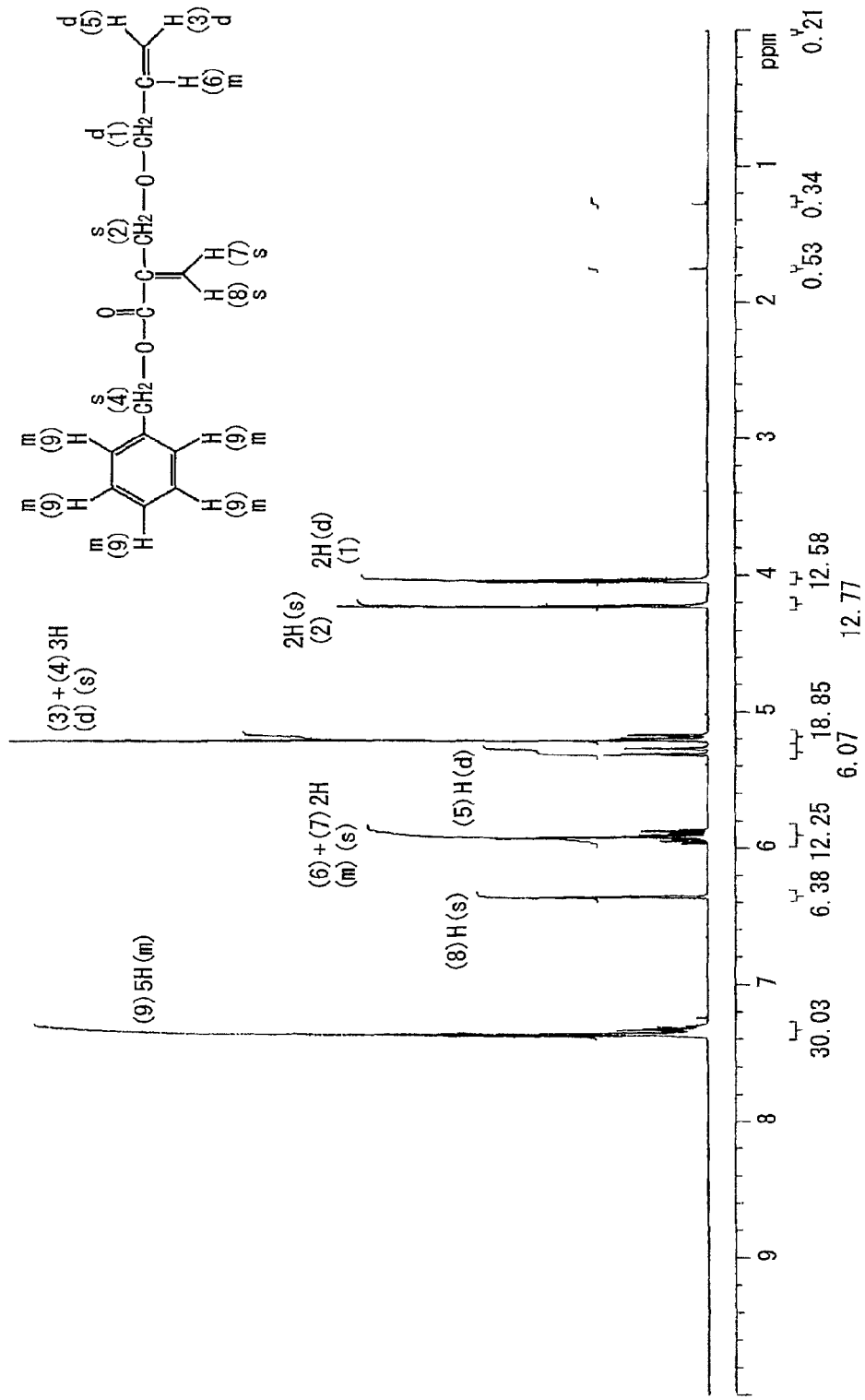
FIG. 4 is a diagram showing the $^1$H-NMR chart and assignments for α-(unsaturated alkoxyalkyl)acrylate in Example 17.

The invention is described more fully in the following examples, although the invention is not limited only to these examples. Unless noted otherwise, "parts" refers to parts by weight, and "%" refers to percent by weight (wt %).

In the following examples, the unsaturated alkyl ester contents, amounts of peroxide, and nitrogen contents are given as the respective amounts (wt %) per 100 wt % of the methyl α-(allyloxymethyl)acrylate included in the product.

Evaluation Methods

Reaction Conversion and Yield

The conversion and yield of the reaction were calculated based on measurement results by gas chromatography or high-performance liquid chromatography.

Analysis of Reaction Mixture by Gas Chromatography (GC)

The reaction solution was diluted with n-hexane or acetonitrile, and measured using a gas chromatograph (GC-2010 (trade name) manufactured by Shimadzu Corporation; capillary column, DB-WAX (trade name); 30 m (length)×0.25 mm (i.d.); membrane thickness, 0.25 μm), and determinations were carried out using a working curve prepared beforehand.

Reaction Tracking with High-Performance Liquid Chromatography (HPLC)

The reaction solution was diluted with the diluting solvent indicated below, and analyzed with the following high-performance liquid chromatographs (HPLC) under the conditions indicated below. The relative proportions of the compounds that formed were calculated based on the peak area ratios.

High-Performance Liquid Chromatographs (HPLC): A combination of DGU-20A5, LC-20AD, SIL-20A, SPD-20A and CTO-20A (all manufactured by Shimadzu Corporation).

Diluting Solvent Acetonitrile/methanol=2/1 (weight ratio)

Eluting Solvent: 5 mol % aqueous phosphoric acid/acetonitrile/methanol mixed solvent Separation column: CAPCELL PACK C18 TYPE: AQ (Shiseido Co., Ltd.)

Allyl Ester Content

The allyl ester (allyl α-(hydroxymethyl)acrylate, allyl α-(methoxymethyl)acrylate and allyl α-(allyloxymethyl) acrylate) contents were measured using a gas chromatograph (GC-2010 (trade name) manufactured by Shimadzu Corporation; capillary column, DB-WAX (trade name); 30 m (length)×0.25 mm (i.d.); membrane thickness, 0.25 μm), and determinations were carried out using a working curve prepared beforehand.

Amount of Peroxide

The amount of peroxide was measured by the iodine titration method in which iodine liberated by having potassium iodide act on the specimen is titrated with sodium thiosulfate, which is a reducing agent.

Nitrogen Content

The nitrogen content was measured using a total nitrogen analyzer (model TN-100 (trade name), manufactured by Mitsubishi Chemical).

Polymerization Conversion

The polymerization conversion was measured using a gas chromatograph (GC-2010 (trade name) manufactured by Shimadzu Corporation; capillary column, DB-17HT (trade name); 30 m (length)×0.25 mm (i.d.); membrane thickness, 0.15 μm), and determinations were carried out using a working curve prepared beforehand.

Weight-Average Molecular Weight and Molecular Weight Distribution of Polymer

The weight-average molecular weight and molecular weight distribution of the polymer were measured under the following conditions using a gel permeation chromatograph (GPC System, from Tosoh Corporation).

Column: two Super HZM-M 6.0×150 (trade name, from Tosoh Corp.) columns

Column temperature: 40° C.

Developing Solution: chloroform

Flow rate: 0.6 mL/min

Sample Concentration: 1 mg/cc

Injection Amount: 20 μL

Detector: RI

Working Curve: standard polystyrene (Tosoh Corp.)

Hue (Color Phase)

The Hazen color number was used as the indicator. The Hazen color number was measured in accordance with the method described in JIS K0071-01 (1998).

$^1$H-NMR Measurement

The sample (200 mg) was dissolved in 3 g of tetramethylsilane-containing heavy chloroform or 3 g of dimethylsulfoxide, and measurement was carried out with a nuclear magnetic resonance spectrometer (400 MHz, Varian).

Example 1

Step 1: Reaction Step

A 500 mL four-neck flask equipped with a stirrer, condenser, thermometer, gas inlet and oil bath was charged with 203 g of methyl α-(hydroxymethyl)acrylate, 10 g of 1,4-diazabicyclo[2.2.2]octane as the catalyst, and 0.20 g of hydroquinone monomethyl ether and 0.20 g of 4-hydroxy-2,2,6,6-tetramethylpiperidin-1-oxyl as the polymerization inhibitors. While blowing air into the reaction mixture, the mixture was then raised to a temperature 100° C. and the pressure was lowered to 4 kPa, and the reaction was carried out for 2 hours while distilling off the water that formed. Next, 152 g of allyl alcohol and 10 g of 1,4-diazabicyclo[2.2.2]octane as the catalyst were added dropwise over a period of 2 hours at normal pressure, and the reaction was continued for another 12 hours. The methyl α-(hydroxymethyl)acrylate conversion was 90 mol %, and the yield of methyl α-(allyloxymethyl)acrylate with respect to the methyl α-(hydroxymethyl)acrylate was 62 mol %.

Step 2: Catalyst Removing Step

The reaction mixture was transferred to a separatory funnel and rinsed three times with 50 g of water, thereby removing the 1,4-diazabicyclo[2.2.2]octane serving as the catalyst. The weight of the organic phase was 270 g, and the nitrogen content in the organic phase was 50 ppm.

Step 3: Distillation Step

The reaction mixture was transferred to a distillation apparatus (theoretical number of plates, 13), 0.27 g of hydroquinone monomethyl ether, 0.27 g of 2-t-butyl hydroquinone and 0.27 g of triphenyl phosphite were added as polymerization inhibitors, and distillation was carried out under a reduced pressure. After removing unreacted allyl alcohol at 7 kPa, 143 g of a mixture of unreacted methyl α-(hydroxymethyl)acrylate and methyl α-(allyloxymethyl)acrylate was removed at a column head temperature of 81° C. The composition of the resulting mixture was 10.5 wt % of methyl α-(hydroxymethyl)acrylate and 89.5 wt % of methyl α-(allyloxymethyl)acrylate. This mixture was transferred to a separatory funnel and diluted with 30 g of hexane, then washed five times with 30 g of water, thereby removing the methyl α-(hydroxymethyl)acrylate, after which the hexane was removed under reduced pressure, giving 122 g of purified methyl α-(allyloxymethyl)acrylate (M-1). The methyl α-(allyloxymethyl)acrylate content was 99.3 wt %, the nitrogen content was 4 ppm, the amount of peroxide was 2 ppm, and the content of allyl ester corresponding to the unsaturated alkyl ester was 0.4 wt %. The content of the methyl α-(hydroxymethyl)acrylate starting material was 0.2 wt % per 100 wt % of the methyl α-(allyloxymethyl)acrylate.

Example 2

A methyl α-(allyloxymethyl)acrylate composition was prepared by adding 500 ppm of 2-tert-butylhydroquinone as an antioxidant to the purified methyl α-(allyloxymethyl)acrylate (M-1) obtained in Example 1. The Hazen color number for this composition was less than 10.

Example 3

A methyl α-(allyloxymethyl)acrylate composition was prepared by adding 500 ppm of p-methoxyphenol and 500 ppm of triphenyl phosphite as antioxidants to the purified methyl α-(allyloxymethyl)acrylate (M-1) obtained in Example 1. The Hazen color number for this composition was less than 10.

Example 4

Step 1: Reaction Step

The same procedure was carried out as in Example 1.

Step 2: Catalyst Removing Step

A catalyst removing step was not carried out, but a distillation step was carried out.

Step 3: Distillation Step

The same procedure was carried out as in Example 1, thereby giving 98 g of purified methyl α-(allyloxymethyl)acrylate (M-2). The methyl α-(allyloxymethyl)acrylate content was 99.3 wt %, the nitrogen content was 120 ppm, the amount of peroxide was 5 ppm, and the allyl ester content was 0.4 wt %. The content of the methyl α-(hydroxymethyl)acrylate starting material was 0.2 wt % per 100 wt % of the methyl α-(allyloxymethyl)acrylate.

Example 5

A methyl α-(allyloxymethyl)acrylate composition was prepared by adding 500 ppm of 2-tert-butylhydroquinone as an antioxidant to the purified methyl α-(allyloxymethyl)acrylate (M-2) obtained in Example 4. The Hazen color number for this composition was less than 10.

Example 6

Step 1: Reaction Step

The same procedure was carried out as in Example 1.

Step 2: Catalyst Removing Step

The same procedure was carried out as in Example 1.

Step 3: Distillation Step

Aside from transferring the reaction mixture to a simple distillation apparatus, the same procedure was carried out as in Example 1, thereby giving 113 g of purified methyl α-(allyloxymethyl)acrylate (M-3). The methyl α-(allyloxymethyl)acrylate content was 97.5 wt %, the nitrogen content was 8 ppm, the amount of peroxide was 5 ppm, and the allyl ester content was 2.3 wt %. The content of the methyl α-(hydroxymethyl)acrylate starting material was 0.2 wt % per 100 wt % of the methyl α-(allyloxymethyl)acrylate.

Example 7

A methyl α-(allyloxymethyl)acrylate composition was prepared by adding 500 ppm of 2-tert-butylhydroquinone as an antioxidant to the purified methyl α-(allyloxymethyl)acrylate (M-3) obtained in Example 6. The Hazen color number for this composition was less than 10.

Example 8

Step 1: Reaction Step

Using the same reaction apparatus as in Example 1, the apparatus was charged with 116 g of methyl α-(hydroxymethyl)acrylate, 87 g of allyl alcohol, 50 g of tungstophosphoric acid as the catalyst, 130 g of cyclohexane, and 0.06 g of hydroquinone monomethyl ether and 0.06 g of 4-hydroxy-2,2,6,6-tetramethylpiperidin-1-oxyl as the polymerization inhibitors. Next, while blowing air into the reaction mixture, the reaction mixture was raised to a temperature of 90° C. and reacted for 8 hours while refluxing cyclohexane. The methyl α-(hydroxymethyl)acrylate conversion was 43 mol %, and the yield of methyl α-(allyloxymethyl)acrylate with respect to the methyl α-(hydroxymethyl)acrylate was 7 mol %.

Step 2: Catalyst Removing Step

The reaction mixture was transferred to a separatory funnel and rinsed twice with 50 g of water, thereby removing the tungstophosphoric acid serving as the catalyst.

Step 3: Distillation Step

The same procedure was carried out as in Example 1, thereby giving 8 g of purified methyl α-(allyloxymethyl) acrylate (M-4). The methyl α-(allyloxymethyl)acrylate content was 99.6 wt %, the nitrogen content was 0 ppm, the amount of peroxide was 82 ppm, and the allyl ester content was 0 wt %. The content of the methyl α-(hydroxymethyl) acrylate starting material was 0.3 wt % per 100 wt % of the methyl α-(allyloxymethyl)acrylate.

Example 9

A methyl α-(allyloxymethyl)acrylate composition was prepared by adding 500 ppm of 2-tert-butylhydroquinone as an antioxidant to the purified methyl α-(allyloxymethyl)acrylate (M-4) obtained in Example 8. The Hazen color number for this composition was 30.

Example 10

Step 1: Reaction Step

A 5 L four-neck flask equipped with a stirrer, condenser, thermometer, gas inlet and vacuum apparatus was charged with 2031.3 g of methyl α-(hydroxymethyl)acrylate, 98.5 g of 1,4-diazabicyclo[2.2.2]octane as the catalyst, and 1.02 g of p-methoxyphenol and 1.02 g of 4-hydroxy-2,2,6,6-tetramethylpiperidin-1-oxyl as the polymerization inhibitors. Next, while blowing an oxygen/nitrogen mixed gas (oxygen concentration, 8 vol %) into the reaction mixture, the pressure was lowered to 10 kPa, the reaction mixture was raised to a temperature 100° C. and reaction was carried out for 2 hours while distilling off the water that formed. The pressure was then released and a solution of 99.4 g of 1,4-diazabicyclo [2.2.2]octane dissolved in 1543.7 g of allyl alcohol at 100° C. was added dropwise over a period of two hours at normal pressure, after which the reaction was continued for another 12 hours. Following the reaction, measurement was carried out by gas chromatography, whereupon the yield of methyl α-(allyloxymethyl)acrylate relative to the methyl α-(hydroxymethyl)acrylate was 62 mol %, the methyl α-(hydroxymethyl)acrylate conversion was 89 mol %, and the yield of allyl ester relative to the methyl α-(hydroxymethyl)acrylate was 2 mol %.

Step 2: Low-Boiling Fraction Removing Step

Next, the remaining allyl alcohol was distilled off by simple distillation at reduced pressure (operating pressure, 7 kPa), thereby giving 2766.8 g of reaction mixture. This reaction mixture contained 1629.6 g of methyl α-(allyloxymethyl)acrylate, had an allyl ester content of 5.4 wt % per 100 wt % of methyl α-(allyloxymethyl)acrylate, and had a content of methyl α-(hydroxymethyl)acrylate as the starting material of 12.1 wt % per 100 wt % of the methyl α-(allyloxymethyl)acrylate.

Step 3: Methyl α-(Hydroxymethyl) Acrylate and Catalyst Removing Step

Next, 927.9 g of an 8 wt % sodium hydroxide solution was added to the resulting reaction mixture and stirred at room temperature for 30 minutes, then left at rest for 30 minutes to effect oil-water separation, thereby giving 2097.6 g of an organic phase. Next, 231.6 g of an 8 wt % sodium hydroxide solution was added to this organic phase and stirred at room temperature for 30 minutes, then left at rest for 30 minutes to effect oil-water separation, thereby giving 2011.0 g of the organic phase. This organic phase contained 1500.2 g of methyl α-(allyloxymethyl)acrylate, the allyl ester content was 6.5 wt % per 100 wt % of methyl α-(allyloxymethyl) acrylate, and the content of the methyl α-(hydroxymethyl) acrylate serving as the starting material had decreased to 0.8 wt % per 100 wt % of the methyl α-(allyloxymethyl)acrylate. The resulting organic phase was then washed with a 5 wt % aqueous solution of Glauber's salt, and oil-water separation was effected. After carrying out this procedure one more time, 1916.7 g of the organic phase was obtained.

Step 4: Distillation Step

In this step, 1.92 g of hydroquinone monomethyl ether, 1.92 g of 2-tert-butyl hydroquinone and 1.92 g of triphenyl phosphite were added as polymerization inhibitors to the organic phase. While blowing in an oxygen/nitrogen mixed gas (oxygen concentration, 8 wt %), distillation was carried out using a packed column (equivalent to a theoretical plate number of 10) filled with Dixon packing. The remaining allyl alcohol was removed at 10 kPa, following which 1329.3 g of methyl α-(allyloxymethyl)acrylate having a purity of 99.4% (M-5) was obtained at a column head temperature of 83° C. The product contained 0.4 wt % of allyl ester, the nitrogen content was below the limit of detection for the analyzer (below 0.1 ppm), and the amount of peroxide was 1 ppm. The product also contained 0.1 wt % of the methyl α-(hydroxymethyl)acrylate serving as the starting material.

Example 11

A methyl α-(allyloxymethyl)acrylate composition was prepared by adding 500 ppm of 2-tert-butylhydroquinone as an antioxidant to the purified methyl α-(allyloxymethyl)acrylate (M-5) obtained in Example 10.

Example 12

A methyl α-(allyloxymethyl)acrylate composition (Me-AMA) was prepared by adding 300 ppm of p-methoxyphenol as an antioxidant to the purified methyl α-(allyloxymethyl) acrylate (M-5) obtained in Example 10.

Example 13

Synthesis of Cyclohexyl α-Allyloxymethyl Acrylate (CH-AMA)

A reactor equipped with a stirring apparatus, temperature sensor, gas inlet, three-way adapter, condenser and distillate receiver was charged with 74.6 g of the methyl α-(allyloxymethyl)acrylate synthesized in Example 10 (M-5), 24.04 g of cyclohexanol (CHOH), 6.0 g of dibutyltin (IV) oxide (DBTO) and 1.5 g of p-methoxyphenol, following which the pressure within the reactor was gradually lowered to 27 kPa under stirring and while passing through a stream of oxygen/nitrogen mixed gas (oxygen concentration, 8 vol %). After reaching 27 kPa, temperature ramp-up was begun and the internal temperature was adjusted to 100° C., then reaction was carried out for 6.5 hours while distilling off the methanol that arose due to transesterification. Following reaction completion, analysis was carried out by gas chromatography, whereupon the peak area ratio of CH-AMA, M-5 and CHOH was 39:45:12. Next, the system was cooled and the pressure was lowered to 800 Pa, after which CHOH and M-5 were distilled off until the internal temperature reached 100° C. This was followed by cooling and pressure release.

The reaction mixture was diluted with n-hexane, and a 4% aqueous NaOH solution was added, as a result of which the DBTO settled out, and was removed by filtration. The filtrate was oil-water separated, then the resulting oil phase was washed with a 15% aqueous NaOH solution and oil-water separated. This operation was repeated five times to remove residual M-5 and p-methoxyphenol. Next, 5.0 g of an alkali adsorbent (Kyowaad 700SL, available from Kyowa Chemical Industry Co, Ltd.) was added to the resulting organic phase, which was then stirred at room temperature for 1 hour and subsequently filtered. The filtrate was charged to a reactor equipped with a stirring apparatus, temperature sensor, gas inlet, three-way adapter, condenser and distillate receiver, and the pressure was gradually lowered to 800 Pa under stirring, while passing through a stream of oxygen/nitrogen mixed gas (oxygen concentration, 8 vol %) and while warming the internal temperature to 25 to 30° C. and thereby removing the n-hexane. After reaching 800 Pa, the pressure was held for 20 minutes, following which the pressure was released, giving 26.4 g of purified cyclohexyl α-allyloxymethyl acrylate (CH-AMA). The content of cyclohexyl α-allyloxymethyl acrylate was 98.0 wt %, no allyl ester was present, the nitrogen content was below the limit of detection for the measurement apparatus, and the amount of peroxide was 2 ppm. In addition, 0.6 wt % of methyl α-(allyloxymethyl)acrylate was also present.

Example 14

A cyclohexyl α-(allyloxymethyl)acrylate composition was prepared by adding 500 ppm of 2-tert-butylhydroquinone as an antioxidant to the purified cyclohexyl α-allyloxymethyl acrylate (CH-AMA) obtained in Example 13. The Hazen color number for this composition was 30.

Example 15

A 200 mL four-neck flask equipped with a stirrer, condenser, thermometer, gas inlet and oil bath was charged with 40.6 g of methyl α-(hydroxymethyl)acrylate, 1.96 g of 1,4-diazabicyclo[2.2.2]octane as the catalyst, and 0.02 g of hydroquinone monomethyl ether and 0.02 g of 4-hydroxy-2,2,6,6-tetramethylpiperidin-1-oxyl as the polymerization inhibitors. While blowing air into the reaction mixture, the mixture was then raised to a temperature of 100° C. and the reaction was carried out for 2 hours. Next, 37.9 g of crotyl alcohol (a cis-trans mixture available from Tokyo Chemical Industry Co., Ltd.) and 1.96 g of the catalyst 1,4-diazabicyclo[2.2.2]octane were added dropwise over a period of 2 hours at normal pressure, and the reaction was continued for another 12 hours. Following the reaction, measurement was carried out by gas chromatography, whereupon the yield of methyl α-(crotyloxymethyl)acrylate with respect to the methyl α-(hydroxymethyl)acrylate was 60 mol %, the conversion of methyl α-(hydroxymethyl)acrylate was 90 mol %, and the yield of crotyl ester as the unsaturated alkyl ester was 1.9 mol % with respect to the methyl α-(hydroxymethyl)acrylate.

Next, the remaining crotyl alcohol was distilled off under a reduced pressure (operating pressure, 7 kPa) by simple distillation, following which 18.4 g of an 8 wt % sodium hydroxide solution was added to the resulting reaction mixture. Stirring was then carried out for 30 minutes at room temperature, after which the mixture at left at rest for 30 minutes to effect oil-water separation. Next, 4.6 g of an 8 wt % sodium hydroxide solution was added to this organic phase and stirring was carried out at room temperature for 30 minutes, after which the mixture was left at rest for 30 minutes to effect oil-water separation, thereby giving an organic phase. The resulting organic phase was then washed with a 5 wt % aqueous solution of Glauber's salt, and oil-water separation was carried out. This operation was carried out one more time, after which 53.9 g of an organic phase was obtained. No methyl α-(hydroxymethyl)acrylate starting material was present in the resulting organic phase.

Next, 0.05 g of hydroquinone methyl ether, 0.05 g of 2-t-butyl hydroquinone and 0.05 g of triphenyl phosphite were added to the above organic phase, and simple distillation was carried out under a reduced pressure. Pure methyl α-(crotyloxymethyl)acrylate was obtained at 13 kPa and a column head temperature of 93° C. The methyl α-(crotyloxymethyl) acrylate content was 97.1 wt %, the nitrogen content was below the limit of detection, the amount of peroxide was 2 ppm, and the content of crotyl ester as the unsaturated alkyl ester was 0.8 wt %. Next, 500 ppm of 2-t-butyl hydroquinone was added as an antioxidant to the resulting purified methyl α-(crotyloxymethyl)acrylate, thereby giving a methyl α-(crotyloxymethyl)acrylate composition. The Hazen color number for this composition was below 10.

Example 16

Synthesis of t-Butyl α-Allyloxymethyl Acrylate (tBu-AMA)

A 500 mL four-neck flask equipped with a stirrer, condenser, thermometer, gas inlet and vacuum apparatus was charged with 307.6 parts of t-butyl acrylate, 39.2 parts of paraformaldehyde (92% purity), 4.5 parts of distilled water, 6.8 parts of 1,4-diazabicyclo[2.2.2]octane as the catalyst, and 1.02 parts of 4-hydroxy-2,2,6,6-tetramethylpiperidin-1-oxyl as the polymerization inhibitor. Next, while stirring and blowing in oxygen/nitrogen mixed gas (oxygen concentration, 8 vol %), the reaction mixture was raised to a temperature of 90° C. and reacted for 11 hours. To drive off the remaining t-butyl acrylate, the system was first cooled to 40° C. then, while blowing in oxygen/nitrogen mixed gas (oxygen concentration, 8 vol %), the pressure in the reactor was lowered to 2.0 kPa, and temperature rise and pressure reduction were gradually carried out. The t-butyl acrylate was ultimately driven off completely when the pressure in the reactor reached 1.0 kPa and the temperature of the reaction mixture reached 100° C. The pressure was released and returned to normal pressure, following which a solution of 6.6 parts of 1,4-diazabicyclo[2.2.2]octane dissolved in 90.6 parts of allyl alcohol was added, and the reaction was continued for 14 hours at 100° C. Following the reaction, rinsing with water was carried out so as to remove the 1,4-diazabicyclo[2.2.2]octane serving as the catalyst, and oil-water separation was effective, giving 227.3 parts of an organic phase. Next, the remaining allyl alcohol was driven off by simple distillation under a reduced pressure (operating pressure, 7.0 kPa), the pressure was reduced further to 1.33 kPa, and 137.0 parts of a mixture of t-Bu-AMA and t-butyl α-hydroxymethyl acrylate was obtained. In addition, in order to remove the t-butyl α-hydroxymethyl acrylate, 42.6 parts of acetic anhydride, 4.0 parts of 1,4-diazabicyclo[2.2.2]octane and 0.07 part of 4H-TEMPO were added to this mixture, the reaction was carried out at 80° C. for 6 hours while blowing in an oxygen/nitrogen mixed gas (oxygen concentration, 8 vol %), and only the t-butyl α-hydroxymethyl acrylate was converted to t-butyl α-acetoxymethyl acrylate. Next, rinsing with water was carried out to remove the 1,4-diazabicyclo[2.2.2]octane catalyst and the acetic acid which formed as a by-product, and oil-water separation was carried out. The resulting organic phase was purified by distillation under a reduced pressure of 1333 Pa, thereby giving tBu-AMA having a purity of 99.4 wt %. When the tBu-AMA was distilled off, the distillation temperature was 87° C. p-Methoxyphenol (300 ppm) was added to the resulting tBu-AMA to give a tBu-AMA composition.

Synthesis Example 1

Synthesis of 1-Chloro-3-Methoxy-Tetramethyldistannoxane

The transesterification catalyst 1-chloro-3-methoxy-tetramethyldistannoxane (CMDS, the compound represented by chemical formula (11) below) was synthesized by the method described by Rokuro OKAWARA and Masanori WADA in *Journal of Organometallic Chemistry*, Vol. 1, 81-88 (1963).

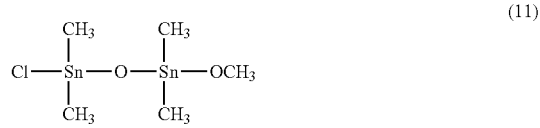

(11)

Example 17

Synthesis of Benzyl α-Allyloxymethyl Acrylate (Bz-AMA)

A reactor equipped with a stirring apparatus, temperature sensor, gas inlet, three-way adapter, condenser and distillate receiver was charged with 115.0 parts of benzyl alcohol (BzOH), 332.2 parts of M-5 synthesized in Example 10, 6.1 parts of CMDS and 4.9 parts of p-methoxyphenol (MEHQ), following which the pressure within the reactor was gradually lowered to 40 kPa under stirring and while passing through a stream of oxygen/nitrogen mixed gas (oxygen concentration, 8 vol %). After reaching 40 kPa, temperature ramp-up was begun, and the methanol that formed in transesterification was distilled off while adjusting the internal temperature to 105 to 110° C. Removal of the methanol by distillation was continued while sampling the reaction mixture once an hour and tracking the reaction product by HPLC. In HPLC analysis, after the peak area of the BzOH was confirmed to be 3% or less of the peak area of the Bz-AMA peak, the pressure was reduced to 1 kPa and maintained at that level for 40 minutes, thereby driving off excess Me-AMA. This was followed by cooling and pressure release.

The reaction mixture was placed in a separatory funnel and diluted with n-hexane, then a 4% solution of sodium hydroxide in water was added, after which the system was thoroughly stirred, left at rest, and the aqueous phase that formed at the bottom was discarded. This procedure was repeated five times, thereby removing CMDS and residual M-5 and MEHQ. The organic phase at the top was removed, 20.0 parts of an alkali adsorbent (Kyowaad 700SL, available from Kyowa Chemical Industry) was added, following which the organic phase was stirred at room temperature for one hour and subsequently filtered. The filtrate was charged to a reactor equipped with a stirring apparatus, temperature sensor, gas inlet, three-way adapter, condenser and distillate receiver, and the pressure was gradually lowered to 1 kPa under stirring while at the same time passing through a stream of oxygen/nitrogen mixed gas (oxygen concentration, 8 vol %) and warming the internal temperature to 25 to 30° C., thereby removing the n-hexane. After reaching 1 kPa, the pressure was held for 20 minutes, following which the pressure was released, giving 197 parts of the target compound Bz-AMA. Next, 0.06 part of MEHQ was added to the resulting Bz-AMA, and the MEHQ concentration was adjusted to 300 ppm. The resulting Bz-AMA was analyzed with a NMR spectrometer. The $^1$H-NMR chart and a diagram with the assignments are shown in FIG. 4.

Example 18

Synthesis of Cyclohexyl α-Allyloxymethyl Acrylate (CH-AMA)

A reactor equipped with a stirring apparatus, temperature sensor, gas inlet, three-way adapter, condenser and distillate receiver was charged with 24.04 parts of cyclohexanol (CHOH), 74.6 parts of M-5 synthesized in Example 10, 6.0 parts of dibutyltin (IV) oxide (DBTO) and 1.5 parts of MEHQ, following which the pressure within the reactor was gradually lowered to 27 kPa under stirring and while passing through a stream of oxygen/nitrogen mixed gas (oxygen concentration, 8 vol %). After reaching 27 kPa, temperature ramp-up was begun and reaction was carried out for 6.5 hours while adjusting the internal temperature to 100° C. and distilling off the methanol that formed in transesterification. Following reaction completion, analysis was carried out by gas chromatography, whereupon the peak area ratio of CH-AMA, M-5 and CHOH were 39:45:12. The system was then cooled and the pressure was lowered to 800 Pa, after which CHOH and M-5 were distilled off until the internal temperature reached 100° C. This was followed by cooling and pressure release.

Figure 5:
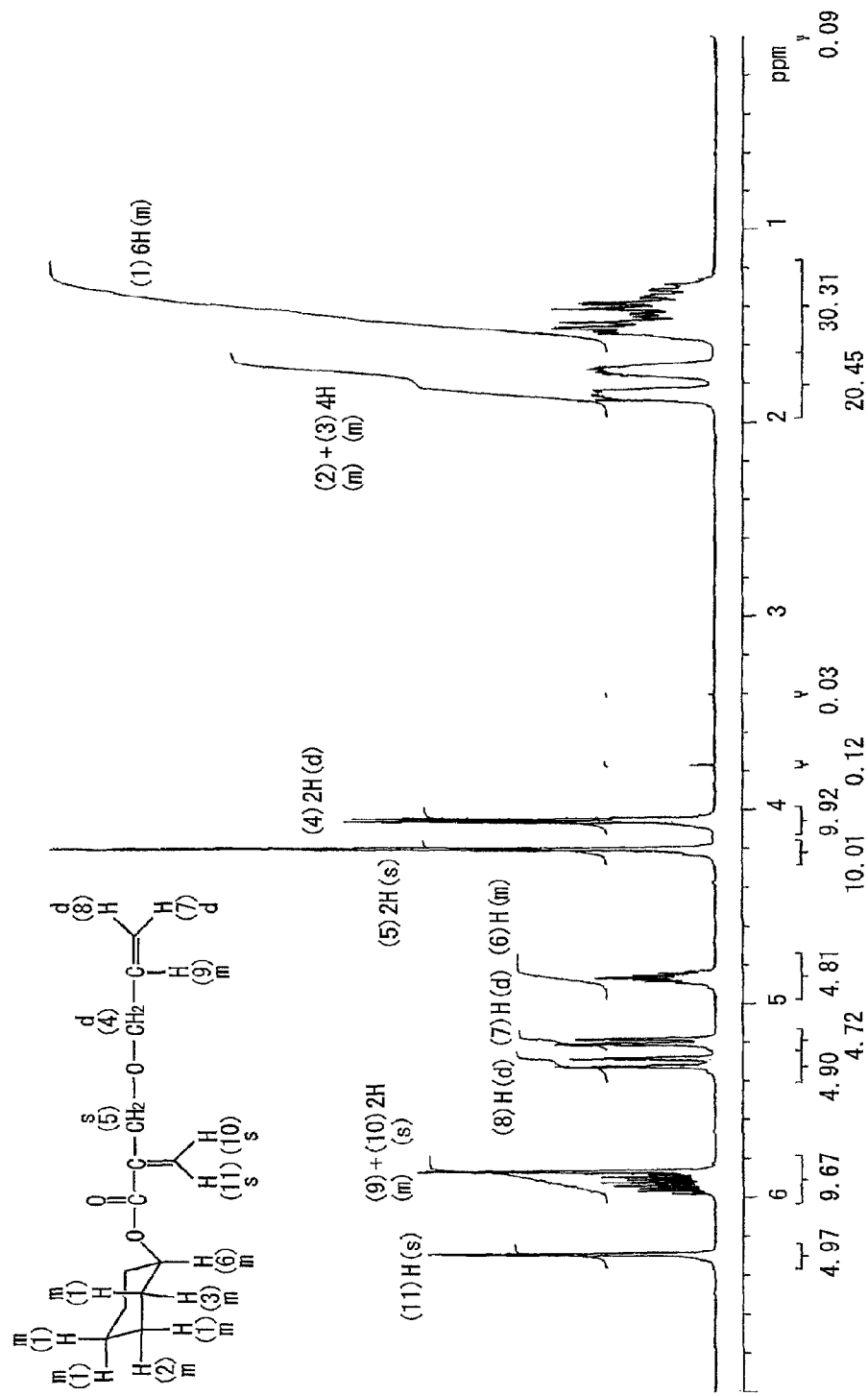
FIG. 5 is a diagram showing the $^1$H-NMR chart and assignments for α-(unsaturated alkoxyalkyl)acrylate in Example 18.

The reaction mixture was diluted with n-hexane, and a 4% aqueous NaOH solution was added, as a result of which the DBTO settled out, and was removed by filtration. The filtrate was oil-water separated, the resulting oil phase was washed with a 15% aqueous NaOH solution and in turn oil-water separated. This operation was repeated five times, thereby removing residual M-5 and MEHQ. Next, 5.0 g of an alkali adsorbent (Kyowaad 700SL, available from Kyowa Chemical Industry Co, Ltd.) was added to the resulting organic phase, which was then stirred at room temperature for 1 hour, and subsequently filtered. The filtrate was charged to a reactor equipped with a stirring apparatus, temperature sensor, gas inlet, three-way adapter, condenser and distillate receiver, and the pressure was gradually lowered to 800 Pa under stirring, while passing through a stream of oxygen/nitrogen mixed gas (oxygen concentration, 8 vol %) and while warming to an internal temperature of 25 to 30° C., thereby removing the n-hexane. After reaching 800 Pa, the pressure was held at this level for 20 minutes, following which the pressure was released, giving 26.4 g of the target compound CH-AMA. Next, 0.008 part of MEHQ was added to the resulting CH-AMA, and the MEHQ concentration was adjusted to 300 ppm. The resulting CH-AMA was analyzed with a NMR spectrometer. The $^1$H-NMR chart and a diagram with the assignments are shown in FIG. 5.

Example 19

Synthesis of Tetrahydrofurfuryl α-Allyloxymethyl Acrylate (THF-AMA)

A reactor equipped with a stirrer, condenser, thermometer and gas inlet was charged with 198.4 parts of tetrahydrofurfuryl alcohol (THFOH), 100.1 parts of the M-5 synthesized in Example 10, 10.9 parts of titanium tetrabutoxide, and 0.10 part of 4H-TEMPO, following which the temperature was raised to 100° C. while passing through a stream of oxygen/nitrogen mixed gas (oxygen concentration, 8 vol %), and the system was reacted for 14 hours. Following reaction completion, gas chromatographic analysis revealed that the peak area ratio for THF-AMA, M-5 and THFOH was 24:11:51. Moreover, n-butyl α-allyloxymethyl acrylate (nBu-AMA), which is an impurity from the catalyst, was present in an amount of 15 area % based on the peak area of the THF-AMA. This reaction mixture was diluted with n-hexane, water was added, and the titanium compound was precipitated out and removed by filtration. The filtrate was oil-water separated and water was added to the resulting organic phase, after which the mixture was thoroughly stirred, then left at rest to allow oil-water separation, and the remaining THFOH was removed to the aqueous phase side. Next, 0.15 part of 4H-TEMPO was added to the resulting organic phase and the mixture was charged to a reactor equipped with a stirring apparatus, temperature sensor, gas inlet, three-way adapter, condenser and distillate receiver, following which the pressure within the reactor was gradually lowered to 400 Pa under stirring and while passing through a stream of oxygen/nitrogen mixed gas (oxygen concentration, 8 vol %). After reaching 400 Pa, the temperature was gradually raised and the remaining M-5 was removed until the internal temperature reached 80° C. This was followed by cooling and pressure release.

Figure 6:
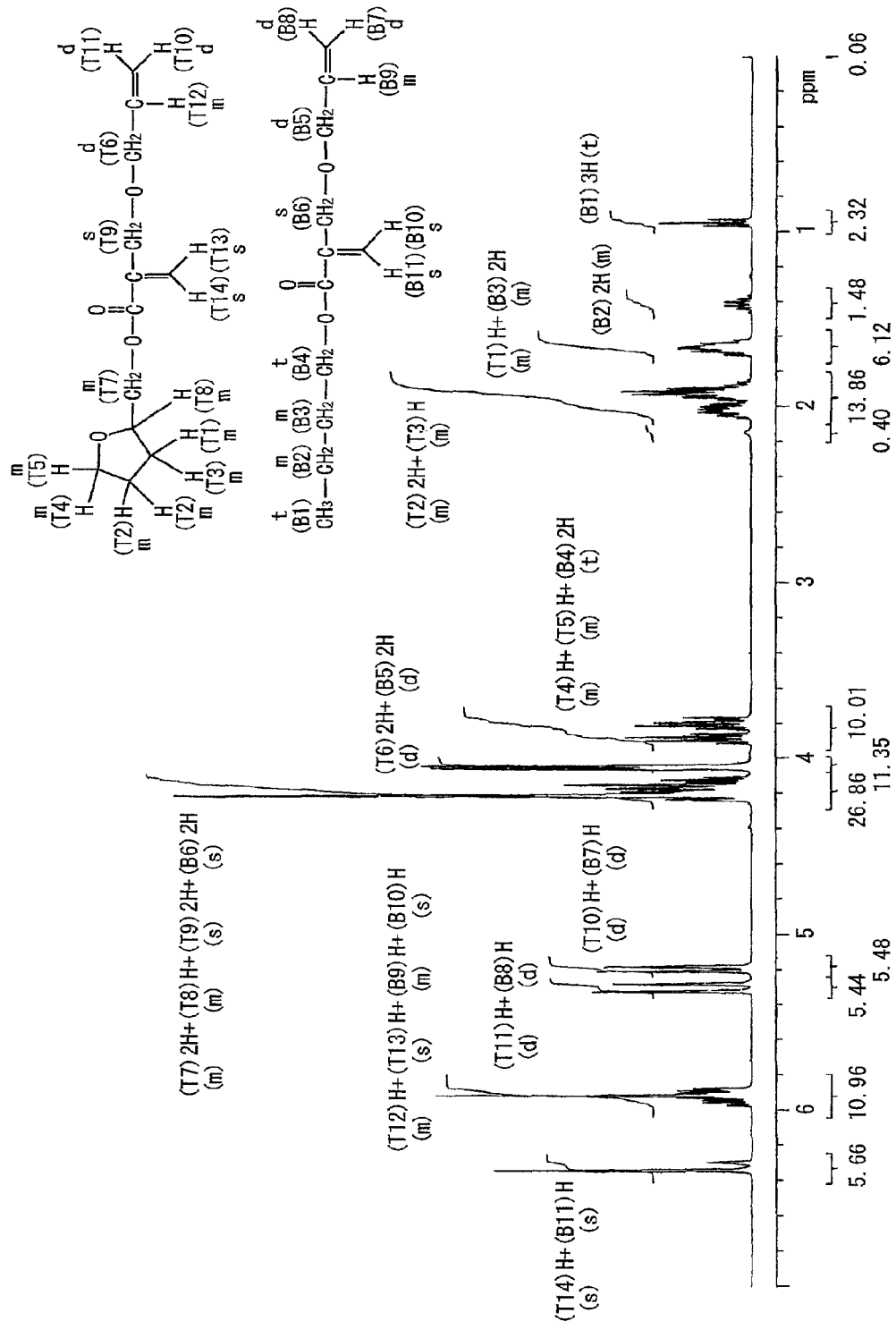
FIG. 6 is a diagram showing the $^1$H-NMR chart and assignments for α-(unsaturated alkoxyalkyl)acrylate in Example 19.

The remaining liquid was diluted with n-hexane, water was added and thorough stirring was carried out, after which the system was left at rest to effect oil-water separation. This operation was repeated three times, thereby removing the 4H-TEMPO. The resulting organic phase was charged to a reactor equipped with a stirring apparatus, temperature sensor, gas inlet, three-way adapter, condenser and distillate receiver, following which the pressure was gradually lowered to 800 Pa under stirring, while passing through a stream of oxygen/nitrogen mixed gas (oxygen concentration, 8 vol %) and while warming to an internal temperature of 25 to 30° C., thereby removing the n-hexane. After reaching 800 Pa, that pressure was maintained for 20 minutes, following which the pressure was released, thereby giving 70.0 parts of the target compound THF-AMA. Next, 0.021 part of MEHQ was added to the resulting THF-AMA, and the MEHQ concentration was adjusted to 300 ppm. The resulting THF-AMA was analyzed by gas chromatography, whereupon this was found to be a mixture of THF-AMA, M-5 and nBu-AMA in a peak area ratio THF-AMA:M-5: nBu-AMA=83:3:14. In addition, analysis was also carried out with a NMR spectrometer. The $^1$H-NMR chart and a diagram with the assignments are shown in FIG. 6.

Example 20

Synthesis of Methoxyethyl α-Allyloxymethyl Acrylate (MOE-AMA)

Figure 7:
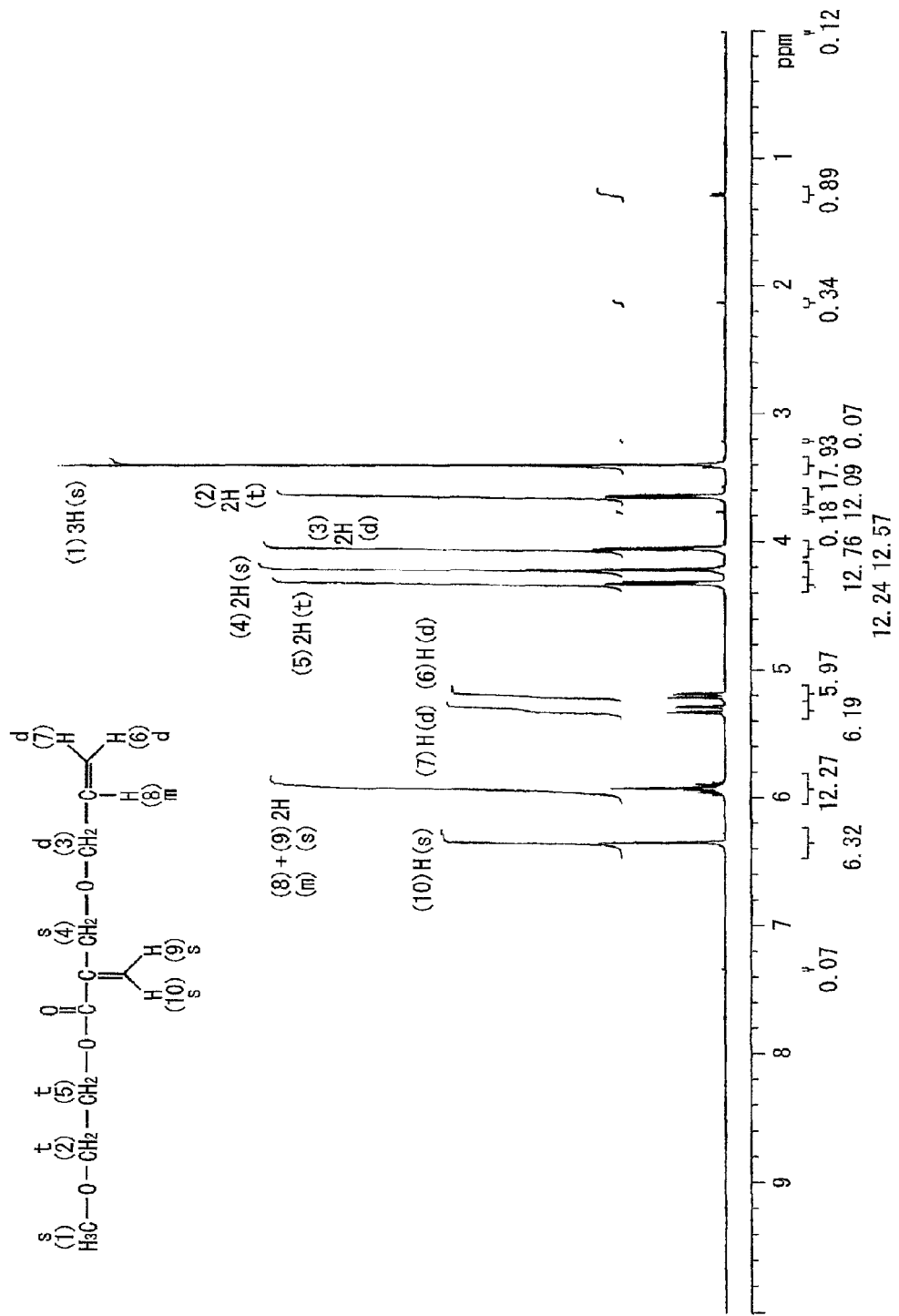
FIG. 7 is a diagram showing the $^1$H-NMR chart and assignments for α-(unsaturated alkoxyalkyl)acrylate in Example 20.

A reactor equipped with a stirrer, condenser, thermometer and gas inlet was charged with 44.0 parts of 2-methoxyethanol (MOEOH), 30.0 parts of M-5 synthesized in Example 10, 2.9 parts of titanium tetraisopropoxide, and 0.03 part of TBH, following which the temperature was raised to 100° C. while passing through a stream of oxygen/nitrogen mixed gas (oxygen concentration, 8 vol %), and reaction was carried out for 8 hours. Following reaction completion, gas chromatographic analysis revealed that the peak area ratio for MOE-AMA, M-5 and MOEOH was 3:1:3. This reaction mixture was diluted with n-hexane, water was added, and the titanium compound was precipitated out and removed by filtration. The filtrate was oil-water separated, then the organic phase and 0.17 part of TBH were charged to a reactor equipped with a stirring apparatus, temperature sensor, gas inlet, Vigreux column, three-way adapter, condenser, still and distillate receiver, following which the pressure within the reactor was lowered to 1333 Pa under stirring and while passing through a stream of oxygen/nitrogen mixed gas (oxygen concentration, 8 vol %). The temperature was gradually raised and the pressure was gradually lowered, thereby driving off and separating, in order: n-hexane, the remaining 2-methoxyethanol, the remaining M-5, and MOE-AMA. The amount of the target product MOE-AMA obtained was 9.1 parts, the final pressure achieved was 533 Pa, and the internal temperature was 110° C. MOE-AMA did not distill off at a pressure of 1333 Pa and an internal temperature of 110° C., but did distill off when the pressure was lowered to 533 Pa. The temperature of the gas phase at this time was 104° C. MEHQ (0.003 part) was added to the resulting MOE-AMA, thereby adjusting the MEHQ concentration to 300 ppm. The resulting MOE-AMA was analyzed with a NMR spectrometer. The $^1$H-NMR chart and a diagram with the assignments are shown in FIG. 7.

Example 21

Synthesis of Ethylhexyl α-Allyloxymethyl Acrylate (EH-AMA)

A reactor equipped with a stirring apparatus, temperature sensor, gas inlet, three-way adapter, condenser and distillate receiver was charged with 21.0 parts of 2-ethylhexanol (EHOH), 50.0 parts of M-5 synthesized in Example 10, 4.0 parts of DBTO and 1.0 part of MEHQ, following which the pressure within the reactor was gradually lowered to 20 kPa under stirring and while passing through a stream of oxygen/nitrogen mixed gas (oxygen concentration, 8 vol %). After reaching 20 kPa, temperature ramp-up was begun and reaction was carried out for 6 hours while adjusting the internal temperature to 100° C. and distilling off the methanol that formed in transesterification. Following reaction completion, analysis was carried out by gas chromatography, whereupon the EHOH had completely converted and the peak area ratio of EH-AMA and M-5 was 36:14. The system was then cooled and the pressure was lowered to 800 Pa, after which M-5 was distilled off until the internal temperature reached 100° C. This was followed by cooling and pressure release.

Figure 8:
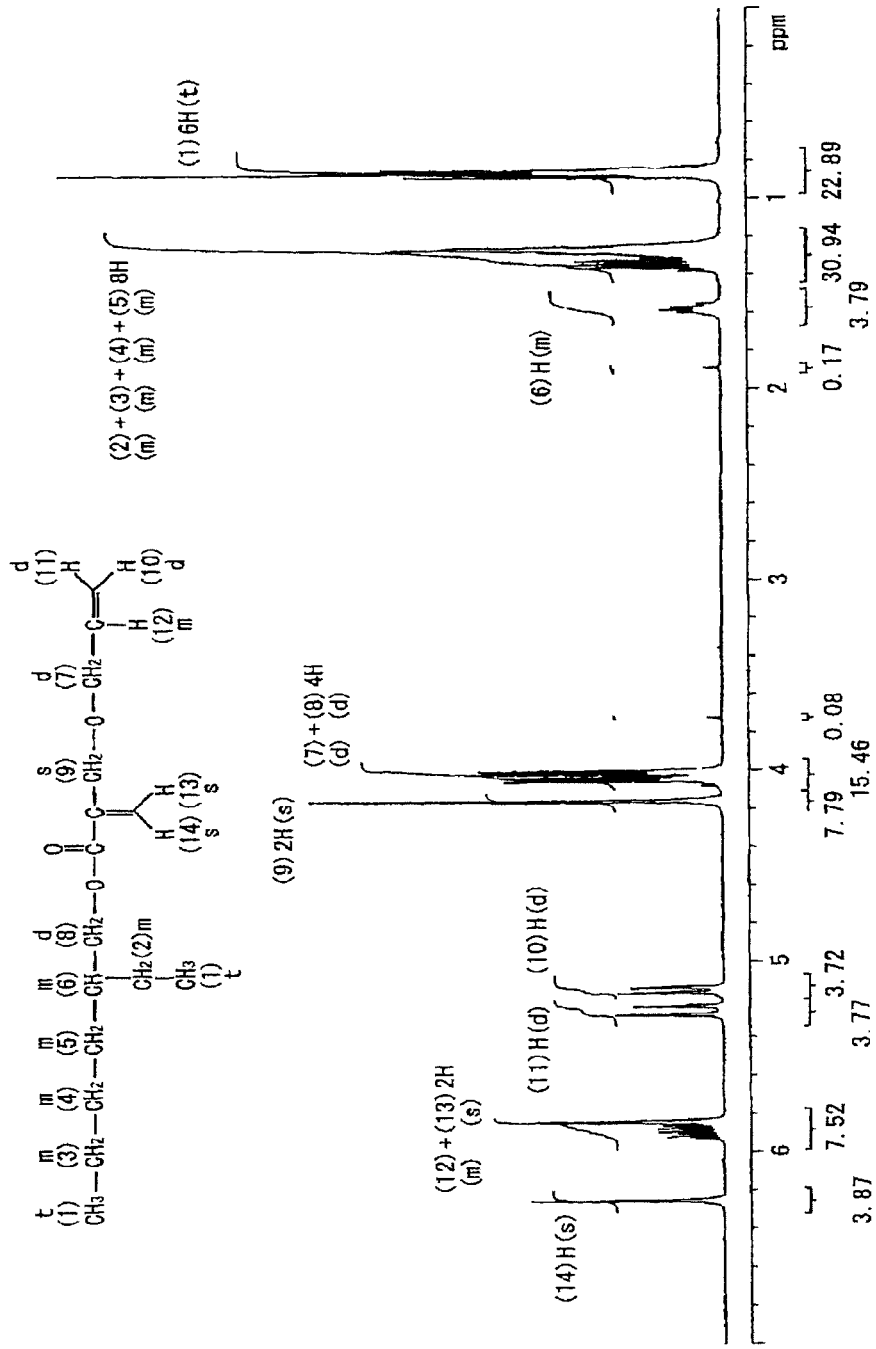
FIG. 8 is a diagram showing the $^1$H-NMR chart and assignments for α-(unsaturated alkoxyalkyl)acrylate in Example 21.

The reaction mixture was diluted with n-hexane, and a 4% aqueous NaOH solution was added, as a result of which the DBTO settled out and was removed by filtration. The filtrate was oil-water separated, and the resulting oil phase was washed with a 15% aqueous NaOH solution and in turn oil-water separated. This operation was repeated five times to remove residual M-5 and MEHQ. Next, 5.0 g of an alkali adsorbent (Kyowaad 700SL, available from Kyowa Chemical Industry Co, Ltd.) was added to the resulting organic phase, which was then stirred at room temperature for 1 hour, and subsequently filtered. The filtrate was charged to a reactor equipped with a stirring apparatus, temperature sensor, gas inlet, three-way adapter, condenser and distillate receiver, and the pressure was gradually lowered to 800 Pa under stirring while passing through a stream of oxygen/nitrogen mixed gas (oxygen concentration, 8 vol %) and warming to an internal temperature of 25 to 30° C., thereby removing the n-hexane. After reaching 800 Pa, the pressure was held for 20 minutes, following which the pressure was released, giving 36.6 g of the target compound EH-AMA. Next, 0.011 part of MEHQ was added to the resulting EH-AMA, and the MEHQ concentration was adjusted to 300 ppm. The resulting EH-AMA was analyzed with a NMR spectrometer. The $^1$H-NMR chart and a diagram with the assignments are shown in FIG. 8.

Example 22

Synthesis of Neopentyl α-Allyloxymethyl Acrylate (NP-AMA)

Figure 9:
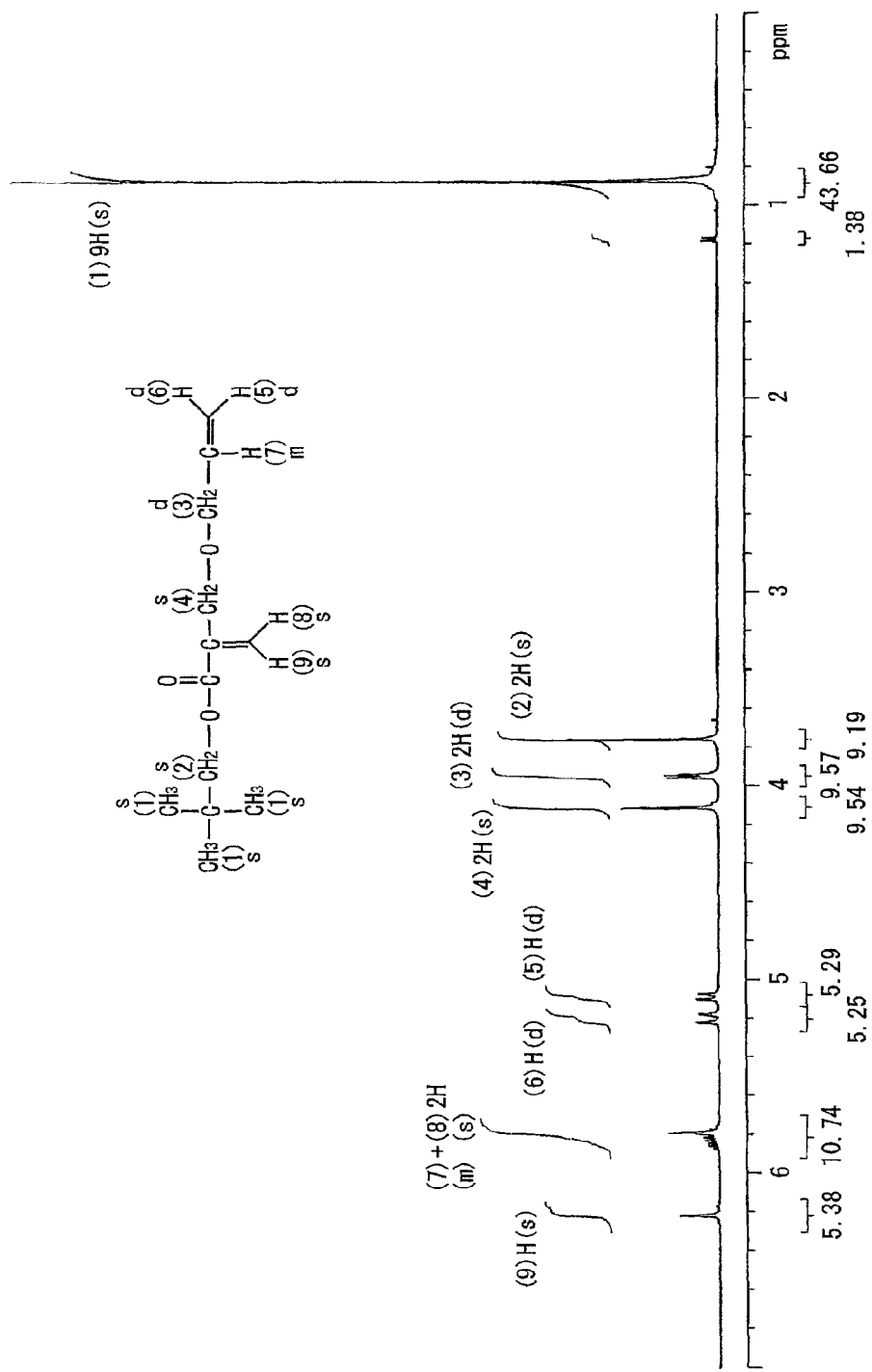
FIG. 9 is a diagram showing the $^1$H-NMR chart and assignments for α-(unsaturated alkoxyalkyl)acrylate in Example 22.

A reactor equipped with a stirrer, condenser, thermometer and gas inlet was charged with 49.5 parts of neopentyl alcohol (NPOH), 88.6 parts of M-5 synthesized in Example 10, 8.1 parts of titanium tetraisopropoxide, and 0.09 part of 4H-TEMPO, following which the temperature was raised to 100° C. while passing through a stream of oxygen/nitrogen mixed gas (oxygen concentration, 8 vol %), and the system was reacted for 6 hours. Following reaction completion, gas chromatographic analysis revealed that the peak area ratio for NP-AMA, M-5 and NPOH was 17:8:7. This reaction mixture was diluted with n-hexane, water was added, and the titanium compound was precipitated out and removed by filtration. The filtrate was oil-water separated, and the organic phase and 0.46 part of 4H-TEMPO were charged to a reactor equipped with a stirring apparatus, temperature sensor, gas inlet, Vigreux column, three-way adapter, condenser, still and distillate receiver, following which the pressure within the reactor was lowered to 1333 Pa under stirring and while passing through a stream of oxygen/nitrogen mixed gas (oxygen concentration, 8 vol %) and the temperature was gradually raised, thereby distilling off and separating, in order: n-hexane, residual NPOH, residual M-5 and NP-AMA. The amount of the resulting target product NP-AMA was 37.1 parts, and the final internal temperature was 110° C. The temperature of the vapor phase during NP-AMA distillation was 106° C. MEHQ (0.011 part) was added to the resulting NP-AMA, thereby adjusting the MEHQ concentration to 300 ppm. The NP-AMA obtained was analyzed with an NMR spectrometer. The $^1$H-NMR chart and a diagram with the assignments are shown in FIG. 9.

Example 23

MEHQ and triphenyl phosphite were each added in amounts of 500 ppm to the NP-AMA composition obtained in Example 22, thereby giving an NP-AMA composition.

Example 24

A reactor equipped with a stirring apparatus, temperature sensor, gas inlet, three-way adapter, condenser and distillate receiver was charged with 50.0 parts of trimethylolpropane (TMP), 350.0 parts of the M-5 synthesized in Example 10, 12.7 parts of CMDS and 3.8 parts of p-methoxyphenol (MEHQ), following which the temperature was raised to 105° C. under stirring and while passing through a stream of oxygen/nitrogen mixed gas (oxygen concentration, 8 vol %). Once the reaction system had become uniform and clear, the pressure within the reactor was gradually lowered to 40 kPa, and removal by distillation of the methanol that had formed due to transesterification was begun. The temperature was adjusted to 105 to 110° C. and the pressure to 40 kPa, following which the reaction mixture was sampled every two hours and removal of the methanol by distillation was continued while tracking the reaction products by HPLC. In HPLC analysis, after confirming that the peak for the compound (TMP-1AMA) obtained by transesterification of only one of the three hydroxyl groups on TMP to an AMA group had vanished and that the peak area for the compound (TMP-2AMA) in which two of the hydroxyl groups were transesterified to AMA groups had fallen to less than $^1/_{10}{}^{th}$ the peak area for the compound (TMP-3AMA) in which all three hydroxyls were transesterified to AMA groups, the pressure was reduced to 1 kPa and maintained at that level for 40 minutes, thereby driving off excess M-5. This was followed by cooling and pressure release.

The reaction mixture was placed in a separatory funnel and diluted with cyclohexane, then a 10% solution of sodium hydroxide in water was added, after which the system was thoroughly permeated, then left at rest and the aqueous phase that formed at the bottom was discarded. This procedure was repeated three times, thereby removing CMDS and residual M-5 and MEHQ. The organic phase at the top was removed, 20.0 parts of an alkali adsorbent (Kyowaad 700SL, available from Kyowa Chemical Industry) was added, following which the organic phase was stirred at room temperature for three hours and subsequently filtered. The filtrate and 0.04 part of MEHQ were charged to a reactor equipped with a stirring apparatus, temperature sensor, gas inlet, three-way adapter, condenser and distillate receiver, and the pressure was lowered under stirring and while passing through a stream of oxygen/nitrogen mixed gas (oxygen concentration, 8 vol %), thereby removing the cyclohexane. While warming the system to a temperature of 25 to 30° C., the pressure was gradually lowered to 1 kPa. After reaching 1 kPa, the pressure was released, giving 120 parts of the target compound: the α-allyloxymethyl acrylic acid ester of TMP (TMP-AMA). The resulting TMP-AMA was analyzed by HPLC, whereupon the peak area ratio of TMP-3A and TMP-2AMA was found to be 98.9/1.1, and no TMP-1AMA or M-5 was observed. The resulting TMP-AMA was also analyzed with an NMR spectrometer. The $^1$H-NMR chart and a diagram with the assignments are shown in FIG. 10.

Example 25

Figure 11:
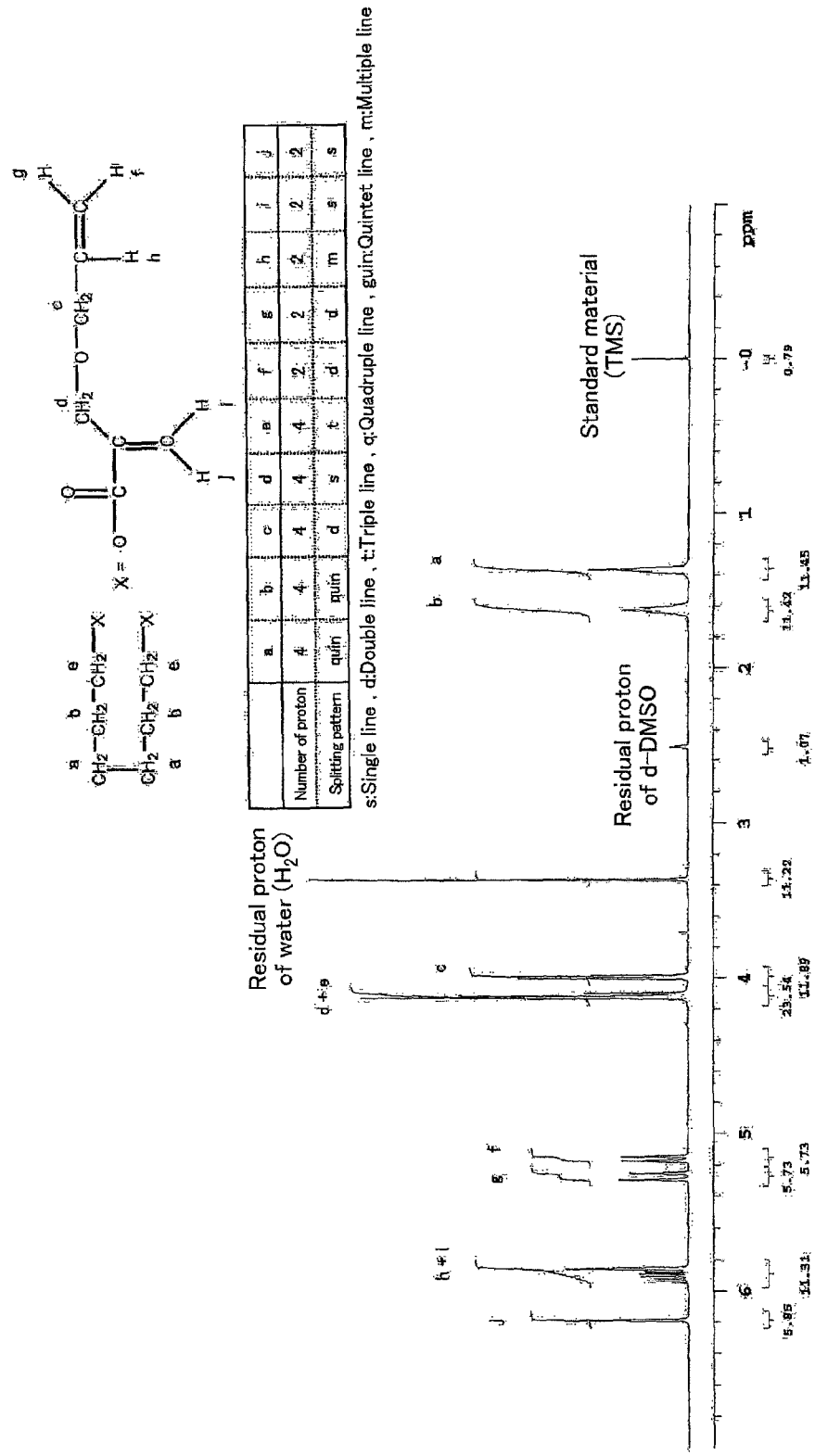
FIG. 11 is a diagram showing the $^1$H-NMR chart and assignments for α-(unsaturated alkoxyalkyl)acrylate in Example 25.

Aside from using 10.4 parts of 1,6-hexanediol (HXD), 55.0 parts of M-5, 2.0 parts of CMDS and 0.7 part of MEHQ as the starting materials charged into the reactor, transesterification was carried out in the same way as in Example 24. After confirming that the peak area for the compound (HXD-1AMA) in which only one of the two hydroxyl groups on HXD was transesterified to an AMA group had fallen to less than $^1/_{10}{}^{th}$ the peak area for the compound (HXD-2AMA) in which both hydroxyl groups were transesterified to AMA groups, the pressure was reduced to 1 kPa and maintained at that level for 40 minutes, thereby driving off excess M-5. This was followed by cooling and pressure release. Next, other than setting the amount of Kyowaad 700SL to 7.0 parts and the amount of MEHQ added to the filtrate to 0.01 part, purification treatment was carried out in the same way as in Example 24, thereby giving 29 parts of the α-allyloxymethyl acrylic acid ester of HXD (HXD-AMA). The resulting HXD-AMA was analyzed by HPLC, whereupon the peak area ratio between HXD-2AMA and M-5 was found to be 99.0/1.0. HXD-1AMA was not observed. The resulting HXD-AMA was analyzed with an NMR spectrometer. The $^1$H-NMR chart and a diagram with the assignments are shown in FIG. 11.

Example 26

Figure 12:
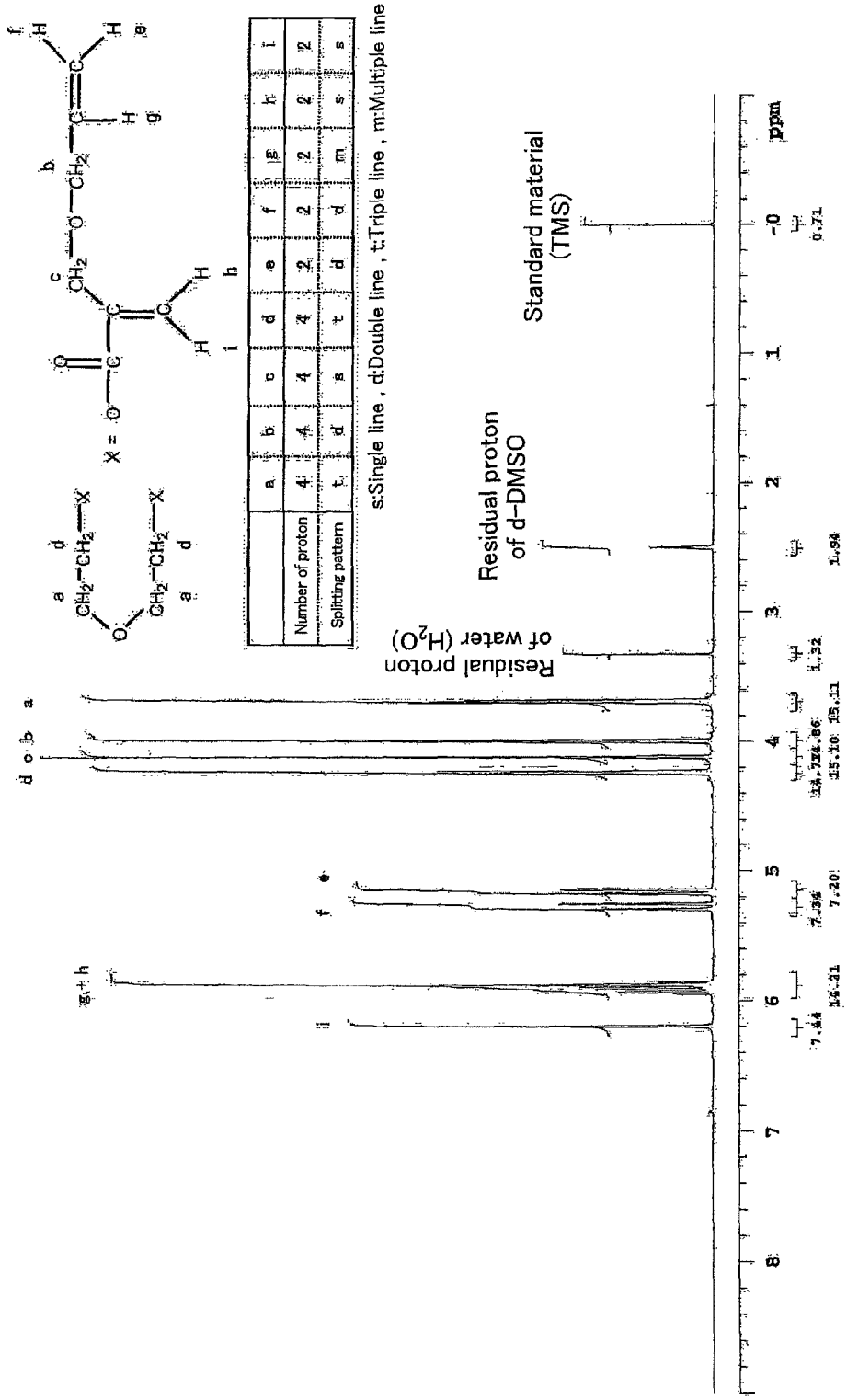
FIG. 12 is a diagram showing the $^1$H-NMR chart and assignments for α-(unsaturated alkoxyalkyl)acrylate in Example 26.

Aside from using 33.0 parts of diethylene glycol (DEG), 195.0 parts of M-5, 3.5 parts of CMDS and 2.2 parts of MEHQ as the starting materials charged into the reactor, transesterification was carried out in the same way as in Example 24. After confirming that the peak area for the compound (DEG-1AMA) in which only one of the two hydroxyl groups on DEG was transesterified to an AMA group had fallen to less than $\frac{1}{10}^{th}$ the peak area for the compound (DEG-2AMA) in which both hydroxyl groups were transesterified to AMA groups, the pressure was reduced to 1 kPa and maintained at that level for 40 minutes, thereby driving off excess M-5. This was followed by cooling and pressure release. Next, other than setting the amount of Kyowaad 700SL to 10.0 parts and the amount of MEHQ added to the filtrate to 0.02 part, purification treatment was carried out in the same way as in Example 24, thereby giving 68 parts of the α-allyloxymethyl acrylic acid ester of DEG (DEG-AMA). The resulting DEG-AMA was analyzed by HPLC, whereupon the peak area ratio between DEG-2AMA and M-5 was found to be 99.1/0.9. DEG-1AMA was not observed. The resulting DEG-AMA was analyzed with an NMR spectrometer. The $^1$H-NMR chart and a diagram with the assignments are shown in FIG. 12.

Example 27

Figure 13:
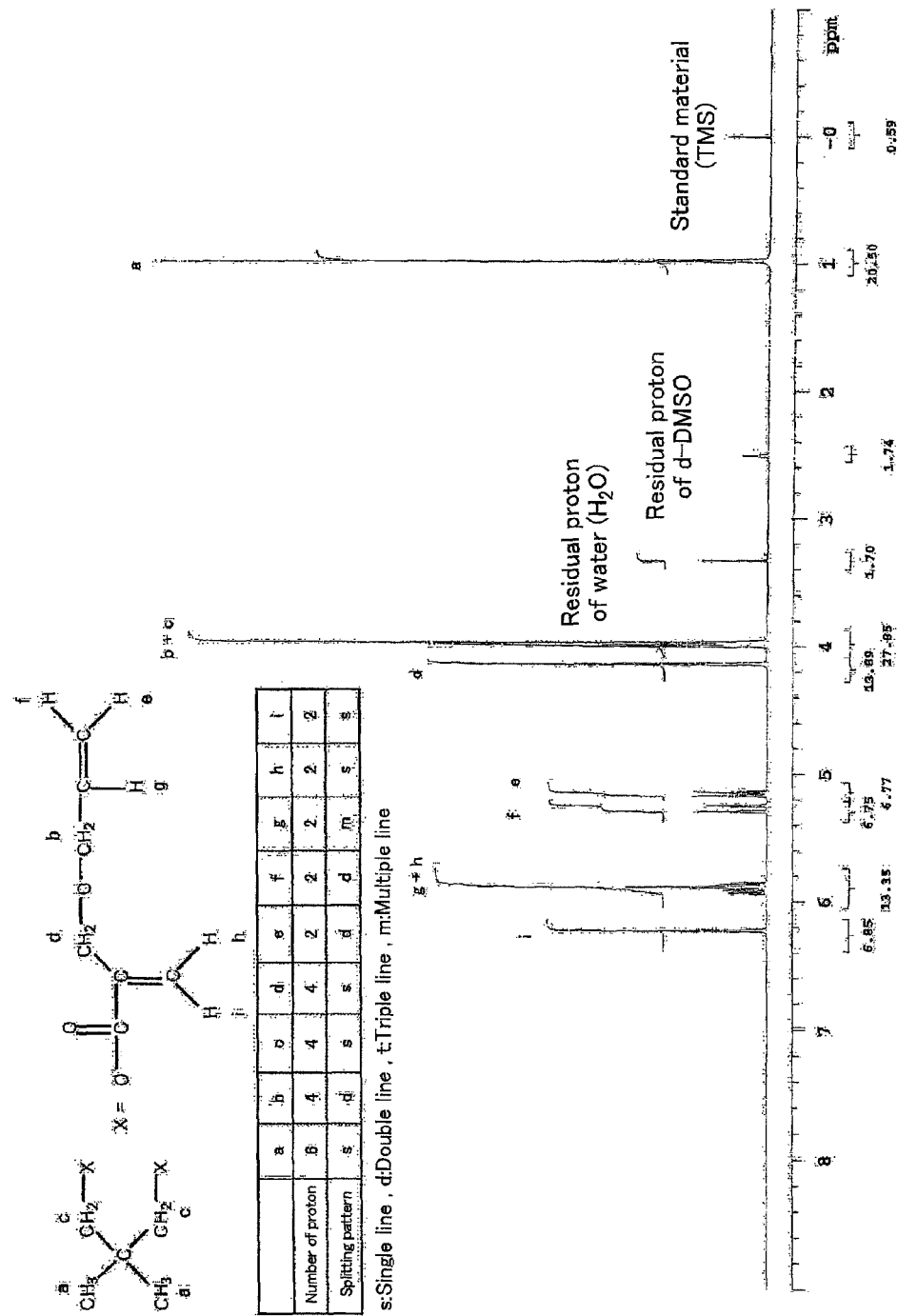
FIG. 13 is a diagram showing the $^1$H-NMR chart and assignments for α-(unsaturated alkoxyalkyl)acrylate in Example 27.

Aside from using 45.0 parts of neopentyl glycol (NPG), 405.0 parts of M-5, 4.9 parts of CMDS and 3.0 parts of MEHQ as the starting materials charged into the reactor, transesterification was carried out in the same way as in Example 24. After confirming that the peak area for the compound (NPG-1AMA) in which only one of the two hydroxyl groups on NPG was transesterified to an AMA group had fallen to less than $\frac{1}{10}^{th}$ the peak area for the compound (NPG-2AMA) in which both hydroxyl groups were transesterified to AMA groups, the pressure was reduced to 1 kPa and maintained at that level for 40 minutes, thereby driving off excess M-5. This was followed by cooling and pressure release. Next, other than setting the amount of Kyowaad 700SL to 20.0 parts and the amount of MEHQ added to the filtrate to 0.04 part, purification treatment was carried out in the same way as in Example 24, thereby giving 132 parts of the α-allyloxymethyl acrylic acid ester of NPG (NPG-AMA). The resulting NPG-AMA was analyzed by HPLC, whereupon the peak area ratio between NPG-2AMA and M-5 was found to be 99.8/0.2. NPG-1AMA was not observed. The resulting NPG-AMA was analyzed with an NMR spectrometer. The $^1$H-NMR chart and a diagram with the assignments are shown in FIG. 13.

Measurement of Boiling Point for α-(Unsaturated Alkoxyalkyl) Acrylate of General Formula (1) at Reduced Pressure, and Calculation of Boiling Point at Normal Pressure A flask equipped with a glass instrument capable of measuring the temperature of the gas phase, a condenser and a pressure reduction apparatus was charged with 100 parts of the M-5 obtained in Example 10 and 0.2 part of 4H-TEMPO, following which the pressure was reduced to 1333 Pa under stirring, and refluxing was carried out while raising the temperature. After confirming that the reflux volume was sufficient, the temperature of the gas phase was measured and found to be 72° C.

The boiling points of the M-5 (methyl α-(allyloxymethyl) acrylate) obtained in Example 10, the tBu-AMA obtained in Example 16 and the NP-AMA obtained in Example 22 were obtained by measuring the temperature of the gas phase during purification by simple distillation at 1333 Pa. The boiling point of the MOE-AMA obtained in Example 20 was obtained by measuring the temperature of the gas phase during purification by simple distillation at 533 Pa. As for the BZ-AMA obtained in Example 17, the CH-AMA obtained in Example 18, the THF-AMA obtained in Example 19 and the EH-AMA obtained in Example 21, because these did not distill out when a sample thereof was charged into the flask, the pressure was reduced to 533 Pa and an oil bath for heating the flask was heated to 130° C., the respective boiling points at 1333 Pa were regarded to be 126° C. or more, and the boiling points at normal pressure were regarded to be 245° C. or more.

Next, the boiling point of NP-AMA at normal pressure (101.3 kPa) was determined from the following formula.

$$P^{0.105} = 14.1 T^{0.105} + C$$

where
P: vapor pressure (mmHg)
T: temperature (K)
C: physical constant

The constant C was determined to be −25.0277 from the boiling point of 106° C. at 1333 Pa (10 mmHg), and the boiling point at a normal pressure of 101.3 kPa (760 mmHg) was calculated to be 219° C. The normal-pressure boiling points of Me-AMA and tBu-AMA were similarly determined, and the boiling points of MOE-AMA at 1333 Pa and at normal pressure were also determined. Those results are shown in Table 1.

TABLE 1

| Radical | Boiling point [° C.] (Data in parentheses: calcurated value) | | |
|---|---|---|---|
| polymerizable monomer | 533 Pa | 1333 Pa | 101.3 kPa (Normal pressure) |
| M-5 | — | 72 | (176) |
| tBu-AMA | — | 87 | (195) |
| NP-AMA | — | 106 | (219) |
| MOE-AMA | 104 | (120) | (237) |
| Bz-AMA | 110 or more | (126 or more) | (245 or more) |
| CH-AMA | 110 or more | (126 or more) | (245 or more) |
| THF-AMA | 110 or more | (126 or more) | (245 or more) |
| EH-AMA | 110 or more | (126 or more) | (245 or more) |

Various evaluations were carried out on the α-(unsaturated alkoxyalkyl)acrylate compositions obtained in Examples 2, 3, 5, 7, 9, 11, 12 and 14 to 27. When indicating the evaluation results, the names of the α-(unsaturated alkoxyalkyl)acrylates used are mentioned. However, this does not mean that pure forms of the indicated α-(unsaturated alkoxyalkyl)acrylate were used; rather, it means that the compositions obtained in the foregoing experimental examples were used. As noted in the above examples, these compositions include other substances such as antioxidants and impurities.

Evaluation Example 1

A 200 mL separable flask equipped with a stirrer, condenser, thermometer, nitrogen inlet and oil bath was charged with 20 g of the methyl α-(allyloxymethyl)acrylate composition mentioned in Example 2 and 30 g of 2-butanone, following which the temperature was raised to 80° C. in a nitrogen atmosphere. After the temperature of the reaction mixture reached 80° C., 0.010 g of azobisisobutyronitrile was added and polymerization was begun. Two hours after the start of polymerization, 16.7 g of 2-butanone was added, and four hours later polymerization was stopped. Conversion of the methyl α-(allyloxymethyl)acrylate was 83%, and the resulting polymer had a weight-average molecular weight of 31000 and a molecular weight distribution of 2.7. There was no change in hue before and after polymerization. The results are shown in Table 2.

Evaluation Example 2

Aside from using the methyl α-(allyloxymethyl)acrylate composition obtained in Example 3, polymerization was carried out in the same way as in Evaluation Example 1. Conversion of the methyl α-(allyloxymethyl)acrylate was 83%, and the resulting polymer had a weight-average molecular weight of 28500 and a molecular weight distribution of 2.8. There was no change in hue before and after polymerization. The results are shown in Table 2.

Evaluation Example 3

Aside from using the methyl α-(allyloxymethyl)acrylate composition obtained in Example 5, polymerization was carried out in the same way as in Evaluation Example 1. Conversion of the methyl α-(allyloxymethyl)acrylate was 83%, and the resulting polymer had a weight-average molecular weight of 33000 and a molecular weight distribution of 3.3. The polymerization solution had a light yellow color, and the hue was 150. The results are shown in Table 2.

Evaluation Example 4

Aside from using the methyl α-(allyloxymethyl)acrylate composition obtained in Example 7, polymerization was carried out in the same way as in Evaluation Example 1. Conversion of the methyl α-(allyloxymethyl)acrylate was 80%, and the resulting polymer had a weight-average molecular weight of 52000 and a broad molecular weight distribution of 4.8 which tended toward the high-molecular-weight side. Some crosslinked polymer formed. The results are shown in Table 2.

Evaluation Example 5

Aside from using the methyl α-(allyloxymethyl)acrylate composition obtained in Example 9, polymerization was carried out in the same way as in Evaluation Example 1. Conversion of the methyl α-(allyloxymethyl)acrylate was 72%, and the resulting polymer had a weight-average molecular weight of 65000 and a broad molecular weight distribution of 6.1 which tended toward the high-molecular-weight side. Some crosslinked polymer formed. The results are shown in Table 2.

Evaluation Example 6

Aside from using the cyclohexyl α-(allyloxymethyl)acrylate composition obtained in Example 14, polymerization was carried out in the same way as in Evaluation Example 1. Conversion of the cyclohexyl α-(allyloxymethyl)acrylate was 82%, and the resulting polymer had a weight-average molecular weight of 33000 and a molecular weight distribution of 2.6. There was no change in hue before and after polymerization. The results are shown in Table 2.

Evaluation Example 7

Aside from using the neopentyl α-(allyloxymethyl)acrylate composition obtained in Example 23, adding the 2-butanone two hours after the start of polymerization and setting the polymerization time thereafter to 6 hours, polymerization was carried out in the same way as in Evaluation Example 1. Conversion of the neopentyl α-(allyloxymethyl)acrylate was 86%, and the resulting polymer had a weight-average molecular weight of 21000 and a molecular weight distribution of 2.7. There was no change in hue before and after polymerization. The results are shown in Table 2.

Evaluation Example 8

Aside from using the methyl α-(crotyloxymethyl)acrylate composition obtained in Example 15, polymerization was carried out in the same way as in Evaluation Example 1. Conversion of the methyl α-(crotyloxymethyl)acrylate was 80%, and the resulting polymer had a weight-average molecular weight of 6800 and a molecular weight distribution of 2.6. There was no change in hue before and after polymerization. The results are shown in Table 2.

Comparative Example 1

Aside from using the purified methyl α-(allyloxymethyl)acrylate (M-1) obtained in Example 1, polymerization was carried out in the same way as in Evaluation Example 1. Following polymerization, gelation occurred in 2 hours. The polymer was colored from the start of polymerization, but because gelation occurred, the Hazen color could not be measured. The results are shown in Table 2.

TABLE 2

| | Antioxidant | | | | Result of polymerization | | |
| --- | --- | --- | --- | --- | --- | --- | --- |
| | Type | Addition amount (ppm) | Type | Addition amount (ppm) | weight-average molecular weight (Mw) | Polydispersity (Mw/Mn) | Hue (Hazen) |
| Evaluation Example 1 | 2-tert-butylhydroquinone | 500 | — | — | $3.1 \times 10^4$ | 2.7 | Not changed |
| Evaluation Example 2 | p-methoxyphenol | 500 | Triphenyl phosphite | 500 | $2.85 \times 10^4$ | 2.8 | Not changed |

TABLE 2-continued

|  | Antioxidant | | | | Result of polymerization | | |
|---|---|---|---|---|---|---|---|
|  | Type | Addition amount (ppm) | Type | Addition amount (ppm) | weight-average molecular weight (Mw) | Polydispersity (Mw/Mn) | Hue (Hazen) |
| Evaluation Example 3 | 2-tert-butylhydroquinone | 500 | — | — | $3.3 \times 10^4$ | 3.3 | 150 |
| Evaluation Example 4 | 2-tert-butylhydroquinone | 500 | — | — | $5.2 \times 10^4$ | 4.8 | — |
| Evaluation Example 5 | 2-tert-butylhydroquinone | 500 | — | — | $6.5 \times 10^4$ | 6.1 | — |
| Evaluation Example 6 | 2-tert-butylhydroquinone | 500 | — | — | $3.3 \times 10^4$ | 2.6 | Not changed |
| Evaluation Example 7 | p-methoxyphenol | 500 | Triphenyl phosphite | 500 | $2.1 \times 10^4$ | 2.7 | Not changed |
| Evaluation Example 8 | 2-tert-butylhydroquinone | 500 | — | — | 6800 | 2.6 | Not changed |
| Comparative Evaluation Example 1 | — | — | — | — | (Geletion 2 hours after polymerization) | | Colored |

Examples 28 to 38, Comparative Examples 1 and 2

The antioxidants shown in Table 3 were added to the purified methyl α-(allyloxymethyl)acrylate (M-1) obtained in Example 1. The Hazen color numbers of these compositions were all less than 10. In each example, the composition was transferred to a glass bottle and air was bubbled through for 5 minutes, following which a storage stability test at 50° C. was carried out for one week. The compositions in Examples 28 to 38 had Hazen color numbers below 10 one week later as well. The compositions in Comparative Examples 1 and 2 had Hazen color numbers of 20, and some coloration was confirmed. Table 3 shows the results (weight-average molecular weight, molecular weight distribution, hue) obtained by carrying out polymerization in the same way as in Evaluation Example 1 using the compositions following the tests. In Comparative Examples 1 and 2, following polymerization, further coloration had occurred relative to the start of polymerization. However, due to gelation, it was not possible to measure the Hazen color.

In Table 3 below, the trade names mentioned in the Antioxidant Type column respectively signified the following compounds.

ANTAGE DAH (available under this trade name from Kawaguchi Chemical Industry Co., Ltd.); 2,5-di-tert-amylhydroquinone ANTAGE DBH (available under this trade name from Kawaguchi Chemical Industry Co., Ltd.); 2,5-di-tert-butylhydroquinone ANTAGE W-400 (available under this trade name from Kawaguchi Chemical Industry Co., Ltd.); 2,2-methylenebis(4-methyl-6-tert-butylphenol)

ADKSTAB PEP24G (available under this trade name from ADEKA Corporation); di(2,4-di-tert-butylphenyl)pentaerythritol diphosphite IRGANOX 1222 (available under this trade name from Ciba Specialty Chemicals); 3,5-di-tert-butyl-4-hydroxybenzylphosphate diethyl ether

TABLE 3

|  | Antioxidant | | | | Result of polymerization | | |
|---|---|---|---|---|---|---|---|
|  | Type | Addition amount (ppm) | Type | Addition amount (ppm) | Weight-average molecular weight (Mw) | Polydispersity (Mw/Mn) | Hue (Hazen) |
| Example 28 | 2-tert-butylhydroquinone | 1000 | — | — | $3.2 \times 10^4$ | 3.0 | Not changed |
| Example 29 | Hydroquinone | 1000 | — | — | $3.5 \times 10^4$ | 3.1 | Not changed |
| Example 30 | ANTAGE DAH | 1000 | — | — | $3.3 \times 10^4$ | 3.3 | Not changed |
| Example 31 | ANTAGE DBH | 1000 | — | — | $3.3 \times 10^4$ | 3.2 | Not changed |
| Example 32 | ANTAGE W-400 | 1000 | — | — | $3.5 \times 10^4$ | 3.2 | Not changed |
| Example 33 | 2-tert-butylhydroquinone | 500 | — | — | $3.6 \times 10^4$ | 3.4 | Not changed |
| Example 34 | Hydroquinone | 500 | — | — | $3.6 \times 10^4$ | 3.4 | Not changed |
| Example 35 | p-methoxyphenol | 1000 | Triphenyl phosphite | 1000 | $2.9 \times 10^4$ | 2.9 | Not changed |
| Example 36 | p-methoxyphenol | 1000 | ADKSTAB PEP24G | 1000 | $3.0 \times 10^4$ | 2.8 | Not changed |
| Example 37 | p-methoxyphenol | 1000 | IRGANOX 1222 | 1000 | $2.8 \times 10^4$ | 2.8 | Not changed |
| Example 38 | p-methoxyphenol | 1000 | Triphenyl phosphine | 1000 | $3.2 \times 10^4$ | 2.9 | Not changed |
| Comparative Example 1 | 2-tert-butylhydroquinone | 200 | — | — | (Geletion 3 hours after polymerization) | | Colored |
| Comparative Example 2 | Hydroquinone | 200 | — | — | (Geletion 3 hours after polymerization) | | Colored |

Evaluation Examples 9 and 10

The methyl α-(allyloxymethyl)acrylate obtained in Example 11 was transferred to a glass or polyethylene vessel and an oxygen/nitrogen mixed gas (oxygen concentration, 8 vol %) was bubbled through for 5 minutes, following which a storage stability test at 50° C. was carried out for 30 weeks. Polymer was not confirmed by GPC for the compositions in any of the vessels. The amounts of peroxide were respectively 2 ppm and 3 ppm. Those results are shown in Table 4.

Comparative Evaluation Examples 2 and 3

The purified methyl α-(allyloxymethyl)acrylate (M-5) obtained in Example 10 was transferred to a glass or polyethylene vessel without adding antioxidant thereto, and an oxygen/nitrogen mixed gas (oxygen concentration, 8 vol %) was bubbled through for 5 minutes, following which a storage stability test at 50° C. was carried out. Polymer was confirmed in all of the vessels one week later. The results are shown in Table 4.

In Table 4, "PE" stands for polyethylene.

TABLE 4

| | Material of container | Test period | Antioxidant Type | Addition amount (ppm) | Amount of peroxide (ppm) | Polymer (GPC) |
|---|---|---|---|---|---|---|
| Evaluation Example 9 | Glass | 30 weeks | 2-tert-butylhydroquinone | 500 | 2 | Not detected |
| Evaluation Example 10 | PE | 30 weeks | 2-tert-butylhydroquinone | 500 | 3 | Not detected |
| Comparative Evaluation Example 2 | Glass | 1 week | No addition | 0 | — | Present (Mw = 2.5 × 10$^4$) |
| Comparative Evaluation Example 3 | PE | 1 week | No addition | 0 | — | Present (Mw = 3.0 × 10$^4$) |

In each case, the radical curability of the α-(unsaturated alkoxyalkyl)acrylate of the invention was evaluated by UV curing in a thin-film, in which the influence of oxygen curing inhibition is readily observable. The following high-output pulse-type UV irradiation system was used as the UV irradiation device.
Pulsed UV Curing System RC-800 (from Xenon Corporation) Number of shots per second: 15

Evaluation Example 11

An α-(unsaturated alkoxyalkyl)acrylate (2.0 parts of the Bz-AMA obtained in Example 17) and a photoinitiator (0.1 part of 2-hydroxy-2-methyl-1-phenylpropane-1-one, available from Ciba Specialty Chemicals under the product name Darocur 1173) were stirred and mixed together, then coated onto an aluminum plate using a bar coater (No. 20). This was then UV irradiated in 1-second units using the above-mentioned UV irradiation system. Prior to UV irradiation, the mixture was a low-viscosity liquid which was not tacky to the touch. However, as curing proceeded, tack appeared; when completely cured, the surface became tack-free. The UV exposure time (in seconds) when tack first appeared and when the surface became tack-free were used as indicators of the radical curability. The results are shown in Table 5.

Evaluation Examples 12 to 16

Aside from changing the α-(unsaturated alkoxyalkyl)acrylate used as shown in Table 5, the radical curability was evaluated in the same way as in Evaluation Example 11. The results are shown in Table 5.

Evaluation Example 17

Aside from using the α-(unsaturated alkoxyalkyl)acrylate obtained in Example 12, the radical curability was evaluated in the same way as in Evaluation Example 11. In some cases tack appeared in as little as 20 seconds and the surface became tack-free in 25 seconds, and in other cases curing did not occur. Hence, the reproducibility was poor. The results are shown in Table 5.

Evaluation Example 18

Aside from using the tBu-AMA obtained in Example 16, the radical curability was evaluated in the same way as in Evaluation Example 11. In some cases tack appeared in as little as 9 seconds and the surface became tack-free in 11 seconds, and in other cases tack appeared in as much as 15 seconds and the surface became tack-free in 17 seconds. Hence, curing occurred, but the reproducibility was poor. The results are shown in Table 5.

Comparative Evaluation Examples 4 to 9

Aside from changing the evaluation sample to (meth)acrylate as shown in Table 5, radical curing was evaluated in the same way as in Evaluation Example 11. The results are shown in Table 5.

The symbols in Table 5 are explained below.

BzA: Benzyl acrylate
CHA: Cyclohexyl acrylate
THFA: Tetrahydrofurfuryl acrylate
THFM: Tetrahydrofurfuryl methacrylate
MOEA: Methoxyethyl acrylate
EHA: 2-Ethylhexyl acrylate
x: Did not cure even when irradiated for 30 seconds
-: Cured product had a glass transition temperature below room temperature, and thus did not become tack-free.

TABLE 5

| Evaluation sample (Note 1) | | | UV irradiation time [Sec.] (Note 2) | | Remarks |
|---|---|---|---|---|---|
| | | | Tack | Tack-free | |
| Evaluation Example 11 | Bz-AMA | (Example 17) | 3 | 4 | — |
| Evaluation Example 12 | CH-AMA | (Example 18) | 3 | 4 | — |
| Evaluation Example 13 | THF-AMA | (Example 19) | 3 | 5 | — |
| Evaluation Example 14 | MOE-AMA | (Example 20) | 7 | — | — |
| Evaluation Example 15 | EH-AMA | (Example 21) | 5 | — | — |
| Evaluation Example 16 | NP-AMA | (Example 22) | 6 | 9 | — |
| Evaluation Example 17 | Me-AMA | (Example 12) | 20~x | 25~x | Poor reproducibility |
| Evaluation Example 18 | tBu-AMA | (Example 16) | 9~15 | 11~17 | Poor reproducibility |
| Comparative Evaluation Example 4 | BzA | | 10 | — | — |
| Comparative Evaluation Example 5 | CHA | | 8 | (13) | — |
| Comparative Evaluation Example 6 | THFA | | 7 | — | — |
| Comparative Evaluation Example 8 | THFM | | x | x | — |
| Comparative Evaluation Example 8 | MOEA | | 17 | — | — |
| Comparative Evaluation Example 9 | EHA | | x | x | — |

Note 1: The parentheses indicate the example in which the α-(unsaturated alkoxyalkyl)acrylate was obtained.
Note 2: The numbers indicate the UV irradiation time (seconds) required for the tack to appear or for the surface to become tack-free. The numbers in the parentheses indicate the UV irradiation time (seconds) thought to be required for the surface to become tack-free, although judging when the surface became tack-free was difficult because the glass transition temperature of the cured product was close to room temperature.

Superiority to (Meth)acrylate Monomers

By contrasting Evaluation Example 11 with Comparative Evaluation Example 4, Evaluation Example 12 with Comparative Evaluation Example 5, Evaluation Example 13 with Comparative Evaluation Examples 6 and 7, Evaluation Example 14 with Comparative Evaluation Example 8, and Evaluation Example 15 with Comparative Evaluation Example 9, it is apparent that by having the curing group be an AMA structure, radical curability is vastly enhanced compared with a (meth)acrylate monomer.

Effects of Boiling Point on Radical Curability in α-(Unsaturated Alkoxyalkyl) Acrylates By contrasting Evaluation Examples 11 to 16 with Evaluation Examples 17 and 18, it is apparent that raising the boiling point is highly effective for the radical curability, and that it is more preferable to set the boiling point at 1333 Pa to at least 95° C. (setting the boiling point at normal pressure to 205° C.)

Evaluation Example 19

An α-(unsaturated alkoxyalkyl)acrylate (2.5 parts of the TMP-AMA obtained in Example 24) and a photoinitiator (0.1 part of 2-hydroxy-2-methyl-1-phenylpropane-1-one, available from Ciba Specialty Chemicals under the product name Darocur 1173) were stirred and mixed together, then coated onto a glass plate using a bar coater (No. 20). This was then UV irradiated using the following UV irradiation system, and the minimum UV dose (mJ/cm$^2$) required for the surface to become tack-free was determined. The results are shown in Table 6.

UV Irradiation system

The UV irradiation system was composed of a combination of each of the following units (all manufactured by Ushio Inc.). This system had a luminance of 15 mW/cm$^2$.
Lamp housing: MPL-25131
Ultrahigh-pressure mercury vapor lamp: USH-250BY
Lamp power supply: HB-25103BY-C
Irradiation optics: PM25C-100

Comparative Evaluation Examples 10 to 15

Aside from using the (meth)acrylate compounds shown in Table 6 instead of TMP-AMA as the evaluation sample, the UV curability was evaluated in the same way as in Evaluation Example 19. Cases in which the surface was liquid (uncured) when exposed to 3000 mJ/cm$^2$ of irradiation were rated as "NG"; cases in which the surface cured but did not become tack-free were rated as "fair." The results are shown in Table 6.

Evaluation Examples 20 to 22, Comparative Evaluation Examples 16 to 20

Aside from using 2.5 parts of the compounds shown in Table 6 as the evaluation sample and using 0.2 part of Darocur 1173 as the photoinitiator, the UV curability was rated in the same way as in Evaluation Example 19 and Comparative Evaluation Examples 10 to 15. The results are shown in Table 6.

Evaluation Example 23

An α-(unsaturated alkoxyalkyl)acrylate (2.5 parts of the TMP-AMA obtained in Example 24) and a drier (0.13 part of a mineral spirits solution of cobalt octoate (metal content, 8%)) were stirred and mixed together, then coated onto a glass plate using a bar coater (No. 20). This was placed in a vat and covered with aluminum foil to shield out light. The sample was left to stand in this state at room temperature in an air atmosphere, and the number of days until the surface cured was determined. The results are shown in Table 6.

Evaluation Examples 24 to 26, Comparative Evaluation Examples 21 to 31

Aside from using the compounds shown in Table 6 instead of TMP-AMA as the evaluation sample, the oxygen curability was evaluated in the same way as in Evaluation Example 23. Cases in which the surface did not cure when left to stand for 10 days were rated as "NG." The results are shown in Table 6. The number of functional groups shown in Table 6 is the average amount (moles) of curable groups in one mole of the compound. Abbreviations for the evaluation samples in Table 6 are shown in Table 7.

TABLE 6

| Evaluation sample | | UV curability | | Oxygen curability | |
|---|---|---|---|---|---|
| Number of functional group | Abbreviation (see Table 7) | Number | UV irradiation amount [mJ/cm$^2$] | Number | Curing days [Day] |
| 3 | TMP-AMA | Evaluation Example 19 | 1500 | Evaluation Example 23 | 1 |
|   | TMPTA | Comparative Evaluation Example 10 | 2700 | Comparative Evaluation Example 21 | x |
|   | TMP-3EO-A | Comparative Evaluation Example 11 | 1500 | Comparative Evaluation Example 22 | x |
|   | TMP-3PO-A | Comparative Evaluation Example 12 | Δ | Comparative Evaluation Example 23 | x |
|   | TMPTM | Comparative Evaluation Example 13 | x | Comparative Evaluation Example 24 | x |
|   | PETAE | Comparative Evaluation Example 14 | x | Comparative Evaluation Example 25 | 3 |
|   | TMPTA/PETAE = 1/1 | Comparative Evaluation Example 15 | x | Comparative Evaluation Example 26 | 7 |
| 2 | HXD-AMA | Evaluation Example 20 | 500 | Evaluation Example 24 | 6 |
|   | DEG-AMA | Evaluation Example 21 | 300 | Evaluation Example 25 | 7 |
|   | NPG-AMA | Evaluation Example 22 | 300 | Evaluation Example 26 | 8 |
|   | HXDA | Comparative Evaluation Example 16 | x | Comparative Evaluation Example 27 | x |
|   | DEGDA | Comparative Evaluation Example 17 | 300 | Comparative Evaluation Example 28 | x |
|   | NPGDA | Comparative Evaluation Example 18 | x | Comparative Evaluation Example 29 | x |
|   | NPG-2PO-A | Comparative Evaluation Example 19 | Δ | Comparative Evaluation Example 30 | x |
|   | TMPDAE | Comparative Evaluation Example 20 | x | Comparative Evaluation Example 31 | 10 |

TABLE 7

| Abbreviation | Origin | Name of compounds |
|---|---|---|
| TMP-AMA | Example 24 | |
| TMPTA | LIGHT ACRYLATE TMP-A (product of Kyoeisha Chemical Co., Ltd.) | Trimethylopropane triacrylate |
| TMP-3EO-A | SR454NS (product of SARTOMER) | Triacrylate of ethylene oxide adduct (average addition number: 3) trimethylolpropane |
| TMP-3PO-A | SR492NS (product of SARTOMER) | Triacrylate of propylene oxide adduct (average addition number: 3))trimethylolpropane |
| TMPTM | LIGHT ESTER TMP (product of Kyoeisha Chemical Co., Ltd.) | Trimethylolpropane trimethacrylate |
| PETAE | NEOALLYL P-30M (product of Daiso Co., Ltd.) | Pentaerythritol triallyl ether |
| TMPTA/PETAE = 1/1 | | 1/1 (mol ratio) mixture of TMPTA and PETAE |
| HXD-AMA | Example 25 | |
| DEG-AMA | Example 26 | |
| NPG-AMA | Example 27 | |
| HXDA | SR238F (product of SARTOMER) | 1,6-hexxanediol diacrylate |
| DEGDA | SR230 (product of SARTOMER) | diethylene glycol diacrylate |
| NPGDA | SR247 (product of SARTOMER) | neopentyl glycol diacrylate |
| NPG-2PO-A | SR9003 (product of SARTOMER) | Diacrylate of propylene oxide adduct (average addition number: 2) neopentyl glycol |
| TMPDAE | NEOALLYL T-20 (product of Daiso Co., Ltd.) | Trimethylolpropane diallyl ether |

Evaluation Example 27

An α-(unsaturated alkoxyalkyl)acrylate (2.0 parts of the Bz-AMA obtained in Example 17) and a photoinitiator (0.1 part of Darocur 1173) were stirred and mixed together, then coated onto an aluminum plate using a bar coater (No. 20). Using the above-described UV irradiation system, this was UV irradiated in 1-second units until the surface became tack-free. After the surface became tack-free, UV irradiation was continued for another 2 seconds, following which the adhesion was rated on a 6-step scale of 0 to 5 in accordance with JIS K5600-5-6 (Crosscut Method) (1999). The results are shown in Table 8.

Evaluation Examples 28 to 32

Aside from changing the α-(unsaturated alkoxyalkyl)acrylate used to those shown in Table 8, adhesion was evaluated in the same way as in Evaluation Example 27. The results are shown in Table 8.

Comparative Evaluation Examples 32 and 33

Aside from using isobornyl acrylate (IBA) and dicyclopentanyl acrylate (DCPA), which are acrylates the cured products of which have glass transition temperatures higher than room temperature, as the evaluation sample, adhesion was evaluated in the same way as in Evaluation Example 27. The results are shown in Table 8.

Evaluation Example 33

An α-(unsaturated alkoxyalkyl)acrylate (5.0 parts of the TMP-AMA obtained in Example 24) and thermo-radical initiators (0.08 part of t-butylperoxy-2-ethylhexanoate (available from NOF Corporation under the product name Perbutyl O; abbreviated below as "PBO"), and 0.02 part of t-hexylperoxyneodecanoate (available from NOF Corporation under the product name Perhexyl ND; abbreviated below as "PHND") were stirred and mixed together, then coated onto a glass plate to a film thickness of 5 μm using a spin coater. This was placed in a hot-air dryer and heated for one hour each at 50° C., 60° C., 90° C. and 120° C. in this order to effect curing. The adhesion of the cured film was rated on a 6-step scale of 0 to 5 in accordance with JIS K5600-5-6 (Crosscut Method) (1999). The results are shown in Table 8.

Comparative Evaluation Examples 34 and 35

Aside from using the compounds shown in Table 8 instead of TMP-AMA as the evaluation samples, adhesion was evaluated in the same way as in Evaluation Example 33. The results are shown in Table 8.

The α-(unsaturated alkoxyalkyl)acrylates in Table 8 are indicated in the same way as in Table 5. The symbols in Table 8 are explained below.
IBA: Isobornyl acrylate
DCPA: Dicyclopentanyl acrylate
TMPTA: Trimethylopropane triacrylate
TMPTM: Trimethylolpropane trimethacrylate The adhesion classification used in Table 8 is described in Table 9.

TABLE 8

| | Evaluation Sample | | Adhesiveness |
|---|---|---|---|
| Evaluation Example 27 | Bz-AMA | (Example 17) | 0 |
| Evaluation Example 28 | CH-AMA | (Example 18) | 0 |
| Evaluation Example 29 | THF-AMA | (Example 19) | 0 |
| Evaluation Example 30 | NP-AMA | (Example 22) | 0 |
| Evaluation Example 31 | Me-AMA | (Example 12) | 0 |
| Evaluation Example 32 | tBu-AMA | (Example 16) | 0 |
| Comparative Evaluation Example 32 | IBA | | 5 |
| Comparative Evaluation Example 33 | DCPA | | 5 |
| Evaluation Example 33 | TMP-AMA | (Example 24) | 0 |
| Comparative Evaluation Example 34 | TMPTA | | 5 |
| Comparative Evaluation Example 35 | TMPTM | | 5 |

TABLE 9

0  Perfectly smooth cut edge, no peeling observed at every cross portions
1  Little peeling of film at intersections of cut lines
   Less than 5% of cross-cut portions clearly affected
2  Film peeled off along cut edge and/or at intersections
   More than 5% and less than 15% of cross-cut portions clearly affected
3  Film greatly peeled off along cut edge partially or on the whole, and/or peeled at multiple portions of spots partially or on the whole
   More than 15% and less than 35% of cross-cut portions clearly affected
4  Film greatly peeled off along cut edge partially or on the whole, and/or peeled at multiple spots partially or on the whole
   More than 35% and less than 65% of cross-cut portions clearly affected
5  Degree of peeling worse than the classification 4

Effects on Adhesion

It is apparent from comparing Evaluation Examples 27 to 33 with Comparative Evaluation Examples 32 to 35 that the adhesion is dramatically improved by giving the curing group an AMA structure.

Evaluation Example 34

Production of Cured product for Specific Gravity Measurement

A composition prepared by stirring and mixing together 5.0 parts of the Bz-AMA obtained in Example 17 and both 0.08 part of t-butylperoxy-2-ethylhexanoate (Perbutyl O, from NOF Corporation) and 0.02 part of t-hexylperoxyneodenoate (Perhexyl ND, for NOF Corporation) as the thermo-radical initiators was cast into a mold having a width of 1 mm. This was placed in a constant-temperature water bath and heated, first at 50° C. for 1 hour, then at 60° C. for 1 hour, following which it was placed in a hot-air dryer and heated at 70° C. for 2 hours, then at 90° C. for 2 hours to effect curing. After cooling to room temperature, the mold was removed, giving a plate-like cured product having a thickness of 1 mm. The cured product was cut out with a cutter and the sidewalls were abraded with sandpaper to as to fashion the plate into a 25 mm×35 mm rectangle. Holes for wires were then formed in the plate, giving a cured product sample for specific gravity measurement.

Measurement of Cure Shrinkage

Bz-AMA, the Bz-AMA cured product obtained as described above, and pure water were temperature conditioned to 23° C., and the specific gravities were measured. The specific gravity of the monomer was measured in a specific gravity bottle. The specific gravity of the cured product was measured based on the Archimedes principle by attaching wires to the cured product and immersion in water. The specific gravity of the cured product was calculated as follows.

Specific gravity of cured product=$(M_2-M_1)/(M_2-M_3)$×specific gravity of water where $M_1$: weight of wire $M_2$: weight of cured product to which wire has been attached $M_3$: weight of cured product immersed in water Specific gravity of water: 1.00

Calculating the Cure Shrinkage

The cure shrinkage was calculated as follows.

Shrinkage (%)=$(dP-dM)/dP$×100 where dP: Specific gravity of cured product dM: Specific gravity of monomer

The results are shown in Table 10.

Evaluation Examples 35 and 36, Comparative Evaluation Examples 36 to 38

Aside from changing the type of evaluation sample used to those shown in Table 10, the cure shrinkage was measured in the same way as in Evaluation Example 34. The results are shown in Table 10.

The α-(unsaturated alkoxyalkyl)acrylates in Table 10 are indicated in the same way as in Table 5. The symbols in Table 10 are explained below.

BzMA: Benzyl methacrylate
CHMA: Cyclohexyl methacrylate
MMA: Methyl methacrylate

TABLE 10

| | Evaluation Sample | | Cure Shurinkage [%] |
|---|---|---|---|
| Evaluation Example 34 | Bz-AMA | (Example 17) | 11.8 |
| Evaluation Example 35 | CH-AMA | (Example 18) | 11.9 |
| Evaluation Example 36 | Me-AMA | (Example 12) | 17.2 |
| Comparative Evaluation Example 36 | BzMA | | 12.3 |
| Comparative Evaluation Example 37 | CHMA | | 13.2 |
| Comparative Evaluation Example 38 | MMA | | 20.9 |

Effects on Cure Shrinkage

It is apparent from contrasting Evaluation Example 34 with Comparative Evaluation Example 36, Evaluation Example 35 with Comparative Evaluation Example 37, and Evaluation Example 36 with Comparative Evaluation Example 38 that the cure shrinkage can be reduced by giving the curing group an AMA structure.

Evaluation Example 37

Figure 14:
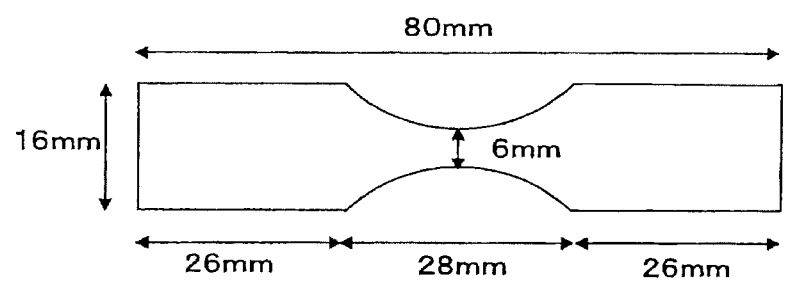
FIG. 14 is a diagram showing the shape of a cured product furnished to a tensile test.

A composition prepared by stirring and mixing together 20.0 parts of the Bz-AMA obtained in Example 17 and both 0.32 part of Perbutyl 0 and 0.08 part of Perhexyl ND as the thermo-radical initiators was cast into a mold having a width of 1 mm. This was placed in a constant-temperature water bath and heated, first at 50° C. for 1 hour, then at 60° C. for 1 hour, following which it was placed in a hot-air dryer and heated at 70° C. for 2 hours, then at 90° C. for 2 hours to effect curing. After cooling to room temperature, the mold was removed, giving a plate-like cured product having a thickness of 1 mm. The cured product was cut out with a cutter and the sidewalls were abraded with sandpaper so as to fashion the plate composition into a shape like that in FIG. 14, thereby giving a total of 7 tensile test samples. These samples were subjected to tensile tests using the tensile testing machine (from Instron Corporation) and test conditions described below. Average values for the 7 samples of each of the following mechanical properties were obtained: breaking energy (also called "breaking toughness," or simply "toughness"; in mJ units), elongation (%), maximum load (N), and modulus of elasticity (GPa). The results are shown in Table 11.

Tensile Testing Machine
Main unit model: 55R1185
Controller model: 5500
Control software: BlueHill2 (Version 2.6.440)
Test Conditions
Chuck interval: 40 mm
Crosshead speed: 5 mm/min Evaluation Example 38, Comparative Evaluation Examples 39 and 40

Aside from changing the types of evaluation samples used to those shown in Table 11, mechanical properties values were measured in the same way as in Evaluation Example 37. The results are shown in Table 11.

Evaluation Example 39

A composition prepared by stirring and mixing together 20.0 parts of the TMP-AMA obtained in Example 24 as the α-(unsaturated alkoxyalkyl)acrylate and both 0.32 part of PBO and 0.08 part of PHND as the thermo-radical initiators was cast into a mold having a width of 1 mm. This was placed in a constant-temperature water bath and heated at 50° C., 60° C. and 70° C. for 1 hour each in this order. The composition was then placed in a hot-air dryer and heated at 90° C. for 1 hour, then at 110° C. for 2 hours to effect curing. After cooling to room temperature, the mold was removed, giving a plate-like cured product having a thickness of 1 mm. The cured product was cut out with a cutter and the side walls were abraded with sandpaper so as to fashion the plate into a shape like that in FIG. 14, thereby giving a total of 7 tensile test samples. These samples were subjected to tensile tests using the tensile testing machine (from Instron Corporation) and test conditions described below. Average values for the 7 samples of each of the following mechanical properties were obtained: modulus of elasticity (GPa), maximum load (N), elongation (%), and breaking energy (also called "breaking toughness," or simply "toughness"; in mJ units). The results are shown in Table 11.

Tensile Testing Machine
Main unit model: 55R1185
Controller model: 5500
Control software: BlueHill2 (Version 2.6.440)
Test Conditions
Chuck interval: 40 mm
Crosshead speed: 5 mm/min Evaluation Example 40, Comparative Evaluation Examples 41 to 44

Aside from using the compounds shown in Table 11 instead of TMP-AMA as the evaluation samples, the mechanical properties were evaluated in the same way as in Evaluation Example 39. The results are shown in Table 11.

The evaluation samples in Table 11 are indicated in the same way as in Table 5. The symbols in Table 11 are the same as those in Table 10.

TABLE 11

|  | Evaluation Sample |  | Mechanical properties ||||
|---|---|---|---|---|---|---|
|  |  |  | Breaking energy [mJ] | Elongation [%] | Maximum load [N] | Modulus of elasticity [GPa] |
| Evaluation Example 37 | Bz-AMA | (Example 17) | 700 | 12.4 | 253 | 2.45 |
| Evaluation Example 38 | CH-AMA | (Example 18) | 256 | 3.98 | 276 | 1.72 |
| Comparative Evaluation Example 39 | BzMA |  | 100 | 1.91 | 263 | 2.97 |
| Comparative Evaluation Example 40 | CHMA |  | 58 | 1.71 | 161 | 2.03 |
| Evaluation Example 39 | TMP-AMA | (Example 24) | 100 | 2.14 | 221 | 2.26 |
| Comparative Evaluation Example 41 | TMPTA |  | 63 | 1.73 | 183 | 2.21 |
| Comparative Evaluation Example 42 | TMPTM |  | 20 | 0.90 | 107 | 2.48 |
| Evaluation Example 40 | NPG-AMA | (Example 27) | 257 | 3.81 | 312 | 2.12 |
| Comparative Evaluation Example 43 | NPGDA |  | 131 | 2.61 | 251 | 2.17 |
| Comparative Evaluation Example 44 | NPG-2PO-A |  | 138 | 4.24 | 125 | 0.89 |

Effects on Mechanical Properties

It is apparent from contrasting Evaluation Example 37 with Comparative Evaluation Example 39, Evaluation Example 38 with Comparative Evaluation Example 40, Evaluation Example 39 with Comparative Evaluation Examples 41 and 42, and Evaluation Example 40 with Comparative Evaluation Example 43 that giving the curing group an AMA structure results in a cured product having hardness (obtaining sufficient values for maximum load and modulus of elasticity) and at the same time having a larger elongation, and thus a larger breaking energy, thus dramatically enhancing the mechanical properties (resulting in both hardness and tenacity).

Example 39

A 100 mL 4-neck flask equipped with a stirrer, condenser, thermometer, gas inlet and oil bath was charged with 34.8 g of methyl α-(hydroxymethyl)acrylate, 3.4 g of 1,4-diazabicyclo[2.2.2]octane, and 0.02 g of 4-hydroxy-2,2,6,6-tetramethyl-1-oxyl as the polymerization inhibitor. Next, the temperature was raised to 95° C. and 26.2 g of allyl alcohol was added dropwise over 8 hours while stirring and blowing air into the reaction mixture, after which the reaction was continued for another 8 hours. Conversion of the methyl α-(hydroxymethyl)acrylate was 86 mol %, and the yields of methyl α(allyloxymethyl)acrylate and allyl ester with respect to the methyl α-(hydroxymethyl)acrylate were respectively 52.2 mol % and 1.0 mol %. The allyl ester content was 2.2 wt % per 100 wt % of methyl α-(allyloxymethyl)acrylate.

Example 40

Aside from charging the allyl alcohol initially rather than adding it dropwise, and carrying out the reaction for 16 hours, the same procedure was followed as in Example 39. Conversion of the methyl α-(hydroxymethyl) acrylate was 86 mol %, and the yields of methyl α-(allyloxymethyl)acrylate and allyl ester with respect to the methyl α-(hydroxymethyl)acrylate were respectively 52.4 mol % and 3.7 mol %. The allyl ester content was 8.2 wt % per 100 wt % of methyl α-(allyloxymethyl)acrylate.

The results for Examples 39 and 40 are shown in Table 12. In Table 12, AMA stands for methyl α-(allyloxymethyl)acrylate.

TABLE 12

|  | Yield (mol %) ||
|---|---|---|
|  | AMA | Allyl ester |
| Addition by dropping (Example 39) | 52.2 | 1.0 |
| Addition at once (Example 40) | 52.4 | 3.7 |

In the following examples, "ratio of methyl α-(hydroxymethyl)acrylate with respect to methyl α-(allyloxymethyl) acrylate" means the ratio (wt %) of methyl α-(hydroxymethyl)acrylate with respect to 100 wt % of the combined amount of methyl α-(hydroxymethyl)acrylate and methyl α-(allyloxymethyl)acrylate.

Also, "percent decrease in methyl α-(hydroxymethyl) acrylate (wt %)" refers to the value calculated with the following formula.

$$\text{Percent decrease(wt \%)} = \left(1 - \frac{\text{Number of moles of } methyl\ \alpha\text{-}(hydroxymethyl)\ acrylate \text{ after treatment}}{\text{Number of moles of } methyl\ \alpha\text{-}(hydroxymethyl)\ acrylate \text{ before treatment}}\right) \times 100$$

Example 41

A 5 L 4-neck flask equipped with a stirrer, condenser, thermometer, gas inlet and pressure reducing device was charged with 2032.1 g of methyl α-(hydroxymethyl)acrylate, 98.9 g of 1,4-diazabicyclo[2.2.2]octane as the catalyst, and 1.02 g of hydroquinone monomethyl ether and 1.02 g of 4-hydroxy-2,2,6,6-tetramethylpiperidin-1-oxyl as the polymerization inhibitors. Next, while blowing in a mixed gas composed of 7 vol % oxygen and 93 vol % nitrogen into the reaction mixture, the pressure was reduced to 10 kPa and the reaction mixture was raised to a temperature of 100° C., then reacted for 2 hours while distilling off water of formation. The pressure was released and a solution of 98.0 g of 1,4-diazabicyclo[2.2.2]octane dissolved in 1523.0 g of allyl alcohol was added dropwise over a period of 2 hours at normal pressure and 100° C., after which the reaction was continued for another 12 hours. Following reaction, measurement was carried out by gas chromatography, whereupon the yield of methyl α-(allyloxymethyl)acrylate was 59 mol % with respect to methyl α-(hydroxymethyl)acrylate, and the conversion of methyl α-(hydroxymethyl)acrylate was 89 mol %. Next, the remaining allyl alcohol was driven off by simple distillation under a reduced pressure (operating pressure, 7 kPa), thereby giving 2778.1 g of the reaction mixture. This reaction mixture contained 56.4 wt % of methyl α-(allyloxymethyl)acrylate and 5.7 wt % of methyl α-(hydroxymethyl)acrylate, and the ratio of methyl α-(hydroxymethyl) acrylate with respect to methyl α-(allyloxymethyl)acrylate was 9.2 wt %.

Example 42

After adding 100 g of a 10 wt % aqueous sodium hydroxide solution to 300 g of the reaction mixture obtained in Example 41 (methyl α-(allyloxymethyl)acrylate, 169.2 g; methyl α-(hydroxymethyl)acrylate, 17.2 g) and stirring at room temperature for 30 minutes, oil-water separation was carried out by leaving the mixture at rest for 30 minutes, thereby giving 223.4 g of the organic phase. The amount of methyl α-(allyloxymethyl)acrylate in the resulting organic phase was 163.5 g, representing 96.6 wt % recovery, and the amount of methyl α-(hydroxymethyl)acrylate was 1.96 g, representing a percent decrease of 88.6 wt %. The ratio of methyl α-(hydroxymethyl)acrylate with respect to methyl α-(allyloxymethyl) acrylate had decreased to 1.1 wt %.

Example 43

Aside from using 15 wt % sodium hydroxide, the procedure was carried out in the same way as in Example 42. Following oil-water separation, the organic phase was obtained in an amount of 205.84 g, and contained 148.8 g of methyl α-(allyloxymethyl)acrylate (recovery: 87.9 wt %) and 0.92 g of methyl α-(hydroxymethyl)acrylate (percent decrease, 94.6 wt %).

The ratio of methyl α-(hydroxymethyl)acrylate with respect to methyl α-(allyloxymethyl)acrylate had decreased to 0.6 wt %.

Example 44

Aside from lowering the amount of the 15 wt % aqueous sodium hydroxide solution from 100 g to 66 g, the procedure was carried out in the same way as Example 43. Following oil-water separation, the organic phase was obtained in an amount of 222.69 g, and contained 160.1 g of methyl α-(allyloxymethyl)acrylate (recovery: 94.6 wt %) and 2.10 g of methyl α-(hydroxymethyl)acrylate (percent decrease: 87.8 wt %).

The ratio of methyl α-(hydroxymethyl)acrylate with respect to methyl α-(allyloxymethyl)acrylate had decreased to 1.3 wt %.

Example 45

Using the same method as in Example 41, 2,776.6 g of a reaction mixture containing 56.1 wt % of methyl α-(allyloxymethyl)acrylate and 7.6 wt % of methyl α-(hydroxymethyl)acrylate was obtained. The ratio of methyl α-(hydroxymethyl)acrylate with respect to methyl α-(allyloxymethyl)acrylate was 11.9 wt %.

Example 46

After adding 100 g of a 12 wt % aqueous sodium hydroxide solution to 300 g of the reaction mixture obtained in Example 45 (methyl α-(allyloxymethyl)acrylate, 168.3 g; methyl α-(hydroxymethyl)acrylate, 22.8 g) and stirring at room temperature for 30 minutes, oil-water separation was carried out by leaving the mixture at rest for 30 minutes, thereby giving 221.8 g of the organic phase. The methyl α-(allyloxymethyl) acrylate in the resulting organic phase was 159.5 g, representing 94.8 wt % recovery, and the methyl α-(hydroxymethyl) acrylate was 2.30 g, representing a percent decrease of 89.9 wt %. The ratio of methyl α-(hydroxymethyl)acrylate with respect to methyl α-(allyloxymethyl)acrylate had decreased to 1.4 wt %.

Example 47

Aside from changing the type and amount of alkali to 193 g of a 10 wt % aqueous sodium carbonate solution, the procedure was carried out in the same way as in Example 46. Following oil-water separation, the organic phase was obtained in an amount of 243.4 g, and contained 168.3 g of methyl α-(allyloxymethyl)acrylate (recovery: 100 wt %) and 10.8 g of methyl α-(hydroxymethyl)acrylate (percent decrease, 52.6 wt %). The ratio of methyl α-(hydroxymethyl) acrylate with respect to methyl α-(allyloxymethyl)acrylate was 6 wt %.

Example 48

Aside from changing the type and amount of alkali to 141 g of a 10 wt % aqueous potassium hydroxide solution, the procedure was carried out in the same way as Example 46. Following oil-water separation, the organic phase was obtained in an amount of 222.8 g, and contained 162.5 g of methyl α-(allyloxymethyl)acrylate (recovery: 96.6 wt %) and 3.95 g of methyl α-(hydroxymethyl)acrylate (percent decrease, 82.7 wt %). The ratio of methyl α-(hydroxymethyl) acrylate with respect to methyl α-(allyloxymethyl) acrylate was 2.4 wt %.

Example 49

Aside from changing the type and amount of alkali to 173 g of a 10 wt % aqueous potassium carbonate solution, the procedure was carried out in the same way as Example 46. Following oil-water separation, the organic phase was obtained in an amount of 236.2 g, and contained 165.4 g of methyl α-(allyloxymethyl)acrylate (recovery: 98.3 wt %) and 13.35 g of methyl α-(hydroxymethyl)acrylate (percent decrease, 41.4 wt %). The ratio of methyl α-(hydroxymethyl) acrylate with respect to methyl α-(allyloxymethyl)acrylate was 7.5 wt %.

The results for Examples 42 to 44 and 46 to 49 are shown in Table 13 below.

TABLE 13

|  |  | Example 42 | Example 43 | Example 44 | Example 46 | Example 47 | Example 48 | Example 49 |
|---|---|---|---|---|---|---|---|---|
| Reaction liquid | Alkali | NaOH | NaOH | NaOH | NaOH | $Na_2CO_3$ | KOH | $K_2CO_3$ |
|  | Amount of reaction liquid (g) | 300 | 300 | 300 | 300 | 300 | 300 | 300 |
|  | Aqueous alkali solution (g) | 100 | 100 | 66 | 100 | 193 | 141 | 173 |
|  | Alkali temperature (wt %) | 10 | 15 | 15 | 12 | 10 | 10 | 10 |
| Before alkali treatment | Alkali (mol) | 0.25 | 0.38 | 0.25 | 0.30 | 0.18 | 0.25 | 0.13 |
|  | Methyl α-(hydroxymethyl) acrylate (mol) | 0.15 | 0.15 | 0.15 | 0.20 | 0.20 | 0.20 | 0.20 |
|  | Methyl α-(allyloxymethyl) acrylate (mol) | 1.08 | 1.08 | 1.08 | 1.08 | 1.08 | 1.08 | 1.08 |
|  | Amount of alkali used (mol; relative to 1 mol of methyl α-(hydroxymethyl) acrylate) | 1.7 | 2.5 | 1.7 | 1.5 | 0.9 | 1.3 | 0.65 |
|  | Methyl α-(hydroxymethyl) acrylate content[X1] (wt %) | 9.2 | 9.2 | 9.2 | 11.9 | 11.9 | 11.9 | 11.9 |
| After alkali treatment | Recovery of methyl α-(allyloxymethyl) acrylate (wt %) | 96.6 | 87.9 | 94.6 | 94.8 | 100 | 96.6 | 98.3 |
|  | Percent decrease of methyl α-(hydroxymethyl) acrylate (wt %) | 88.6 | 94.6 | 87.8 | 89.9 | 52.6 | 82.7 | 41.4 |
|  | Methyl α-(hydroxymethyl) acrylate content[X1] (wt %) | 1.1 | 0.6 | 1.3 | 1.4 | 6 | 2.4 | 7.5 |

In Table 13, "content of methyl α-(hydroxymethyl)acrylate[1]" refers to the ratio of methyl α-(hydroxymethyl)acrylate (wt %) per 100 wt % of methyl α-(hydroxymethyl)acrylate and methyl α-(allyloxymethyl)acrylate combined.

Example 50

Using the same method as in Example 41, 2778.0 g of a reaction mixture containing 55.9 wt % (1552.9 g, 9.94 mol) of methyl α-(allyloxymethyl)acrylate and 7.1 wt % (197.2 g, 1.70 mol) of methyl α-(hydroxymethyl)acrylate was obtained. The ratio of methyl α-(hydroxymethyl)acrylate with respect to methyl α-(allyloxymethyl)acrylate was 11.3 wt %.

After adding 919.5 g of an 8 wt % aqueous sodium hydroxide solution (sodium hydroxide: 73.6 g, 1.84 mol)) to this reaction mixture and stirring at room temperature for 30 minutes, oil-water separation was carried out by leaving the mixture at rest for 30 minutes, thereby giving 2101.3 g of the organic phase. The number of moles of the sodium hydroxide added per mole of the methyl α-(hydroxymethyl)acrylate was 1.08 moles. The amount of methyl α-(allyloxymethyl)acrylate in the resulting organic phase was 1507.9 g (9.65 mol), representing 97.1 wt % recovery, and the amount of methyl α-(hydroxymethyl)acrylate was 38.9 g (0.33 mol), representing a percent decrease of 80.3 wt %. The ratio of methyl α-(hydroxymethyl)acrylate relative to methyl α-(allyloxymethyl)acrylate was 2.5 wt %.

In addition, 231.3 g of an 8 wt % sodium hydroxide solution (sodium hydroxide: 18.5 g, 0.46 mol) was added to this organic phase and stirring was carried out at room temperature for 30 minutes, after which oil-water separation was carried out by leaving the mixture at rest for 30 minutes, thereby giving 2017.7 g of the organic phase. The number of moles of the sodium hydroxide added per mole of the methyl α-(hydroxymethyl)acrylate was 1.39 moles. The amount of methyl α-(allyloxymethyl)acrylate in the resulting organic phase was 1478.5 g (9.47 mol), representing 98.1 wt % recovery, and the amount of methyl α-(hydroxymethyl)acrylate was 13.0 g (0.11 mol), representing a percent decrease of 66.6 wt %. The ratio of methyl α-(hydroxymethyl)acrylate to methyl α-(allyloxymethyl)acrylate was 0.9 wt %.

Next, the resulting organic phase was washed with a 5 wt % aqueous solution of Glauber's salt, and oil-water separation was carried out. This operation was carried out one more time. The organic phase was obtained in an amount of 1900.7 g, and contained 1464.6 g (9.38 mol) of methyl α-(allyloxymethyl)acrylate and 6.3 g (0.05 mol) of methyl α-(hydroxymethyl)acrylate. The ratio of methyl α-(hydroxymethyl)acrylate to methyl α-(allyloxymethyl)acrylate was 0.4 wt %. This organic phase was subjected to distillation using a packed column under a reduced pressure of 2 kPa, thereby giving 1337.3 g of methyl α-(allyloxymethyl)acrylate having a purity of 99.5 wt %.

Example 51

A 1 L four-neck flask equipped with a stirrer, condenser, thermometer and gas inlet was charged with 406.4 g of methyl α-(hydroxymethyl)acrylate, 39.3 g of 1,4-diazabicyclo [2.2.2]octane as the catalyst, and 0.41 g of hydroquinone monomethyl ether, 0.41 g of t-butylhydroquinone and 0.41 g of triphenyl phosphite as the polymerization inhibitors. Next, while blowing a mixed gas composed of 7 vol % oxygen and 93 vol % nitrogen into the reaction mixture, the reaction mixture was raised to a temperature of 100° C. One hour after the reaction mixture reached 100° C., 305.0 g of allyl alcohol was added dropwise over a period of 2 hours, following which reaction was continued for another 13 hours. Following the reaction, measurement was carried out by gas chromatography, whereupon the yield of methyl α-(allyloxymethyl)acrylate was 56 mol % with respect to the methyl α-(hydroxymethyl)acrylate, and the conversion of methyl α-(hydroxymethyl)acrylate was 87 mol %. Next, the remaining allyl alcohol was driven off by simple distillation under a reduced pressure (operating pressure, 7 kPa), thereby giving 556.6 g of the reaction mixture. This reaction mixture contained 52.9 wt % (294.4 g, 1.89 mol) of methyl α-(allyloxymethyl)acrylate and 8.8 wt % (49.0 g, 0.42 mol) of methyl α-(hydroxymethyl)acrylate, and the ratio of methyl α-(hydroxymethyl)acrylate with respect to methyl α-(allyloxymethyl)acrylate was 14.3 wt %.

Comparative Example 3

Distilled water (38 g) was added to 279.0 g of the reaction mixture obtained in Example 51 (methyl α-(allyloxymethyl)

acrylate, 147.5 g; methyl α-(hydroxymethyl)acrylate, 24.6 g), and the system was stirred at room temperature for 30 minutes, then left stand for 30 minutes to effect oil-water separation, giving 232.5 g of an organic phase. The amount of methyl α-(allyloxymethyl)acrylate in the resulting organic phase was 145.7 g (0.93 mol), representing 98.8 wt % recovery, and the amount of methyl α-(hydroxymethyl)acrylate was 18.8 g (0.16 mol), representing a percent decrease of 23.6 wt %. In addition, the ratio of methyl α-(hydroxymethyl)acrylate with respect to methyl α-(allyloxymethyl)acrylate was 11.4 wt % (first rinse).

Next, 38 g of distilled water was added to the resulting organic phase, and the system was stirred at room temperature for 30 minutes, then left to stand for 30 minutes to effect oil-water separation, giving 223.8 g of an organic phase. The amount of methyl α-(allyloxymethyl)acrylate in the resulting organic phase was 142.0 g (0.91 mol), representing 97.5 wt % recovery, and the amount of methyl α-(hydroxymethyl)acrylate was 16.4 g (0.14 mol), representing a percent decrease of 12.8 wt %. In addition, the ratio of methyl α-(hydroxymethyl)acrylate with respect to methyl α-(allyloxymethyl)acrylate was 10.4 wt % (second rinse).

Rinsing with water alone was similarly carried out three times, as a result of which 179.4 g of an organic phase that had been rinsed a total of 5 times was obtained. The amount of methyl α-(allyloxymethyl)acrylate in the resulting organic phase was 122.1 g (0.78 mol), and the amount of methyl α-(hydroxymethyl)acrylate was 9.4 g (0.08 mol). The ratio of methyl α-(hydroxymethyl)acrylate to methyl α-(allyloxymethyl)acrylate was 7.1 wt %.

The results obtained by carrying out five rinses in Comparative Example 3 are shown in Table 14 below.

TABLE 14

| | Before water | Number of times of water washing | | | | |
|---|---|---|---|---|---|---|
| | washing | 1 | 2 | 3 | 4 | 5 |
| Total amount of organic phase | 279.0 | 232.5 | 223.8 | 209.3 | 193.6 | 179.4 |
| Methyl α-(hydroxymethyl) acrylate (g) | 24.6 | 18.8 | 16.4 | 14 | 11.5 | 9.4 |
| Methyl α-(allyloxymethyl) acrylate (g) | 147.5 | 145.7 | 142 | 137.5 | 128.8 | 122.1 |
| Methyl α-(hydroxymethyl) acrylate content[1] (wt %) | 14.5 | 11.4 | 10.4 | 9.2 | 8.2 | 7.1 |
| Recovery (wt %) of methyl α-(allyloxymethyl) acrylate (wt %) | — | 98.8 | 97.5 | 96.8 | 93.7 | 94.8 |
| Percent decrease of methyl α-(hydroxymethyl) acrylate (wt %) | — | 23.6 | 12.8 | 14.6 | 17.9 | 18.3 |

In Table 14, "Content of methyl α-(hydroxymethyl)acrylate[1]" refers to the ratio of methyl α(hydroxymethyl)acrylate per 100 wt % of methyl α-(hydroxymethyl)acrylate and methyl α-(allyloxymethyl)acrylate combined.

Example 52

A 500 mL four-neck flask equipped with a stirrer, condenser, thermometer, gas inlet and pressure reducing device was charged with 232.2 g of methyl α-(hydroxymethyl)acrylate, 11.22 g of 1,4-diazabicyclo[2.2.2]octane as the catalyst, and 0.12 g of hydroquinone monomethyl ether and 0.12 g of 4-hydroxy-2,2,6,6-tetramethylpiperidin-1-oxyl as the polymerization inhibitors. Next, while blowing a mixed gas composed of 7 vol % oxygen and 93 vol % nitrogen into the reaction mixture, the reaction mixture was raised to a temperature of 90° C.; 1.5 hours after reaching 90° C., the reaction mixture was cooled to 76° C. and a solution of 22.4 g of 1,4-diazabicyclo[2.2.2]octane dissolved in 103.6 g of methanol was added dropwise over 2 hours, after which the reaction was continued for another 14 hours at 76° C. Following the reaction, measurement was carried out by gas chromatography, whereupon the yield of methyl α-(methoxymethyl)acrylate was 72 mol % with respect to methyl α-(hydroxymethyl)acrylate, and the conversion of methyl α-(hydroxymethyl)acrylate was 87 mol %. The resulting reaction mixture had a weight of 369.4 g and contained 50.8 wt % (187.6 g, 1.44 mol) of methyl α-(methoxymethyl)acrylate and 8.1 wt % (29.9 g, 0.26 mol) of methyl α-(hydroxymethyl)acrylate. The ratio of methyl α-(hydroxymethyl)acrylate to methyl α-(methoxymethyl)acrylate was 13.7 wt %.

Next, 176 g of a 10 wt % aqueous sodium hydroxide solution (sodium hydroxide: 17.6 g, 0.44 mol) was added to this reaction mixture and stirring was carried out at room temperature for 30 minutes, after which oil-water separation was carried out by leaving the mixture at rest for 30 minutes, thereby giving 253.0 g of the organic phase. The number of moles of the sodium hydroxide added per mole of the methyl α-(hydroxymethyl)acrylate was 1.7 moles. The amount of methyl α-(allyloxymethyl)acrylate in the resulting organic phase was 178.4 g (1.37 mol), representing 95.1 wt % recovery, and the amount of methyl α-(hydroxymethyl)acrylate was 3.3 g (0.03 mol), representing a percent decrease of 89.0 wt %. The ratio of methyl α-(hydroxymethyl)acrylate to methyl α-(methoxymethyl)acrylate was as low as 1.8 wt %.

In above Examples 41 to 52, methyl α-(hydroxymethyl)acrylate was used in the reaction as the acrylate having a hydroxyalkyl group at the α-position, and methyl α-(allyloxymethyl)acrylate, or methyl α-(methoxymethyl)acrylate was prepared as the α-(alkoxyalkyl)acrylate. To the extent that the preparation method of the invention entails preparing an α-(alkoxyalkyl)acrylate by using in the reaction an acrylate having a hydroxyalkyl group at the α-position, one can assume that the advantageous effects of the invention will be similarly achieved so long as the preparation method includes this step. Also, when an acrylate having a hydroxyalkyl group at the α-position is used to prepare an α-(alkoxyalkyl)acrylate, if the acrylate having a hydroxyalkyl group at the α-position and the α-(alkoxyalkyl)acrylate (target product) within the crude composition (reaction mixture, solution following reaction) obtained by the reaction have similar boiling points, the mechanism by which the difficulty of separating these during distillation arises will be the same. Accordingly, based on a consideration of the advantageous effects of this invention which have been corroborated together with the mechanism of action achieved by the constitution of the invention as set forth in the specification, it will be appreciated that the technical significance of this invention has been amply demonstrated.

Comparative Example 4

A crude AMA solution (438.0 g) containing 66.2 wt % (209.5 g, 1.86 mol) of methyl α-(allyloxymethyl)acrylate and 7.7 wt % (33.7 g, 0.29 mol) of methyl α-(hydroxymethyl)acrylate was purified by distillation using a packed column at a reduced pressure of 2 kPa. The ratio of methyl α-(hydroxymethyl)acrylate to methyl α-(allyloxymethyl)acrylate prior to purification was 10.4 wt %. After distillation, 226.4 g of a liquid containing 88.5 wt % (200.3 g, 1.28 mol) of methyl α-(allyloxymethyl)acrylate and 10.1 wt % (22.8 g, 0.20 mol) of methyl α-(hydroxymethyl)acrylate was obtained. The ratio of methyl α-(hydroxymethyl)acrylate to methyl α-(allyloxymethyl)acrylate in the liquid obtained was 10.2 wt %. Hence, the ratio of methyl α-(hydroxymethyl)acrylate to methyl α-(allyloxymethyl)acrylate was substantially unchanged compared with prior to distillation. It was apparent from the results of this Comparative Example 4 that, in purification by distillation, separation of the methyl α-(allyloxymethyl)acrylate and methyl α-(hydroxymethyl)acrylate is difficult.

Example 53

A 2 L four-neck flask equipped with a stirrer, condenser, thermometer, gas inlet and oil bath was charged with 813 g of methyl α-(hydroxymethyl)acrylate, 39 g of 1,4-diazabicyclo[2.2.2]octane as the catalyst, and 0.4 g of hydroquinone monomethyl ether and 0.4 g of 4-hydroxy-2,2,6,6-tetramethylpiperidin-1-oxyl as the polymerization inhibitors. Next, while blowing air into the reaction mixture, the reaction mixture was raised to a temperature of 100° C., the pressure was reduced to 10 kPa, and reaction was carried out for 2 hours while distilling off the water of formation. Next, 610 g of allyl alcohol and 39 g of the catalyst 1,4-diazabicyclo[2.2.2]octane were added dropwise over two hours at normal pressure, and the reaction was carried out for another 12 hours. Following the reaction, measurement was carried out by gas chromatography, whereupon the yield of methyl α-(allyloxymethyl)acrylate was 60 mol % with respect to methyl α-(hydroxymethyl)acrylate, and the conversion of methyl α-(hydroxymethyl)acrylate was 88 mol %. Next, the remaining allyl alcohol was driven off by simple distillation under a reduced pressure (operating pressure, 7 kPa), thereby giving 1139 g of the reaction mixture. This reaction mixture contained 652 g of methyl α-(allyloxymethyl)acrylate, 85 g of methyl α-(hydroxymethyl)acrylate, and 30 g of 1,4-diazabicyclo[2.2.2]octane as the catalyst.

Example 54

Acetic anhydride (87 g) as a derivatizing agent was added dropwise over a period of 1 hour to 371 g of the reaction mixture obtained in Example 53, and the mixture was stirred for 2 hours at 50° C. The amount of methyl α-(hydroxymethyl)acrylate in 458 g of this reaction mixture was 2 g. The reaction mixture was then washed with water to remove the catalyst, following which purification was carried out by distillation using a distillation apparatus (theoretical number of plates, 13) and under reduced pressure (operating pressure, 2 kPa). The amount of reaction mixture prior to distillation was 450 g, and included 256 g of methyl α-(allyloxymethyl)acrylate, 1 g of methyl α-(hydroxymethyl)acrylate and 30 g of methyl α-(acetoxymethyl)acrylate. Following distillation, 192 g of product containing 99.3 wt % of methyl α-(allyloxymethyl)acrylate and 0.2 wt % of methyl α-(hydroxymethyl)acrylate was obtained.

Example 55

As in Example 54, 30 g of phthalic anhydride as the derivatizing agent was added over one hour to 50 g of the reaction mixture obtained in Example 53, and the mixture was stirred for 2 hours at 50° C. The amount of methyl α-(hydroxymethyl)acrylate in the reaction mixture was 0.9 g. The same steps as in Example 54 were subsequently carried out, thereby giving a product containing 98.6 wt % of methyl α-(allyloxymethyl)acrylate and 1.3 wt % of methyl α-(hydroxymethyl)acrylate.

Example 56

As in Example 54, 24 g of phenyl isocyanate as the derivatizing agent was added over one hour to 50 g of the reaction mixture obtained in Example 53, and the mixture was stirred for 2 hours at 50° C. The amount of methyl α-(hydroxymethyl)acrylate in the reaction mixture was 0.1 g. The same steps as in Example 54 were subsequently carried out, thereby giving a product containing 99.5 wt % of methyl α-(allyloxymethyl)acrylate and 0.1 wt % of methyl α-(hydroxymethyl)acrylate.

Example 57

As in Example 54, 12 g of propylene oxide as the derivatizing agent was added over one hour to 50 g of the reaction mixture obtained in Example 53, and the mixture was stirred for 6 hours at 50° C. The amount of methyl α-(hydroxymethyl)acrylate in the reaction mixture was 1.4 g. The same steps as in Example 54 were subsequently carried out, thereby giving a product containing 97.5 wt % of methyl α-(allyloxymethyl)acrylate and 2.4 wt % of methyl α-(hydroxymethyl)acrylate.

Example 58

As in Example 54, 14 g of phosphoric acid anhydride as the derivatizing agent was added over one hour to 50 g of the reaction mixture obtained in Example 53, and the mixture was stirred for 6 hours at 50° C. The amount of methyl α-(hydroxymethyl)acrylate in the reaction mixture was 1.5 g. The same steps as in Example 54 were subsequently carried out, thereby giving a product containing 97.2 wt % of methyl α-(allyloxymethyl)acrylate and 2.7 wt % of methyl α-(hydroxymethyl)acrylate.

The results for Examples 54 to 58 are shown in Table 15. The amounts of addition (equivalents) in Table 15 indicate the equivalents relative to the amount of hydroxyl groups in the reaction mixture.

TABLE 15

|  | Acrylate having a hydroxyalkyl group at the α-position | Alcohol | Derivatizing agent | | Result of distillation | |
|---|---|---|---|---|---|---|
|  |  |  | Type | Addition amount (equivalent) | Methyl α-(allyloxymethyl) acrylate (wt %) | Methyl α-(hydroxymethyl) acrylate (wt %) |
| Example 54 | Methyl α-(hydroxymethyl) acrylate | Allyl alcohol | Acetic anhydride | 1.1 | 99.3 | 0.2 |
| Example 55 |  |  | Phthalic anhydrid | 2 | 98.6 | 1.3 |
| Example 56 |  |  | Phenyl isocyanate | 2 | 99.5 | 0.1 |

TABLE 15-continued

| | | Derivatizing agent | | Result of distillation | |
|---|---|---|---|---|---|
| Acrylate having a hydroxyalkyl group at the α-position | Alcohol | Type | Addition amount (equivalent) | Methyl α-(allyloxymethyl) acrylate (wt %) | Methyl α-(hydroxymethyl) acrylate (wt %) |
| Example 57 | | propylene oxide | 2 | 97.5 | 2.4 |
| Example 58 | | Phosphoric acid anhydride | 2 | 97.2 | 2.7 |

EXPLANATION OF REFERENCE NUMERALS s: Peak splitting pattern is a singlet
d: Peak splitting pattern is a doublet
t: Peak splitting pattern is a triplet
m: Peak splitting pattern is a multiplet

The invention claimed is:

1. An α-(unsaturated alkoxyalkyl)acrylate composition comprising: an α-(unsaturated alkoxyalkyl)acrylate represented by general formula (1) below

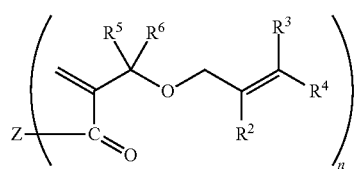

where $R^2$, $R^3$ and $R^4$ are identically or independently a hydrogen atom or a $C_{1-30}$ organic group;
$R^5$ and $R^6$ are identically or independently a hydrogen atom or a $C_{1-18}$ alkyl group which may be substituted; and Z is an n-valent organic group, with n being an integer greater than or equal to 1;
and an antioxidant,
wherein the antioxidant content is from 0.03 to 0.5 wt. % relative to 100 wt. % of the α-(unsaturated alkoxyalkyl)acrylate; and
wherein the composition has a nitrogen content, per 100 wt. % of the α-(unsaturated alkoxyalkyl)acrylate, of 100 ppm or less.

2. The α-(unsaturated alkoxyalkyl)acrylate composition according to claim 1, wherein the composition has a content of unsaturated alkyl ester or of acrylate having a hydroxyalkyl group at the α-position, per 100 wt. % of the α-(unsaturated alkoxyalkyl)acrylate, of 1 wt. % or less.

3. The α-(unsaturated alkoxyalkyl)acrylate composition according to claim 2, wherein the α-(unsaturated alkoxyalkyl)acrylate content is at least 95 wt. % per 100 wt. % of the composition.

4. The α-(unsaturated alkoxyalkyl)acrylate composition according to claim 1, wherein $R^5$ and $R^6$ in the general formula (1) are hydrogen atoms.

5. The α-(unsaturated alkoxyalkyl)acrylate composition according to claim 1, wherein the α-(unsaturated alkoxyalkyl)acrylate comprises an α-(allyloxymethyl)acrylate.

6. The α-(unsaturated alkoxyalkyl)acrylate composition according to claim 1, wherein the antioxidant comprises a phenolic antioxidant and/or a phosphorus-based antioxidant.

7. The α-(unsaturated alkoxyalkyl)acrylate composition according to claim 1, wherein the α-(unsaturated alkoxyalkyl)acrylate has a boiling point at 1333 Pa of at least 95° C.

8. The α-(unsaturated alkoxyalkyl)acrylate composition according to claim 1, wherein n in the general formula (1) is 1.

9. The α-(unsaturated alkoxyalkyl)acrylate composition according to claim 8, wherein Z in the general formula (1) is a group represented by the general formula —$OR^1$, where $R^1$ is a hydrogen atom or a $C_{1-30}$ organic group.

10. The α-(unsaturated alkoxyalkyl)acrylate composition according to claim 1, wherein Z in the general formula (1) is an n-valent linkage, with n being an integer greater than or equal to 2.

11. The α-(unsaturated alkoxyalkyl)acrylate composition of claim 1, wherein the composition has an amount of peroxide per 100 wt. % of the α-(unsaturated alkoxyalkyl)acrylate of 50 ppm or less.

12. A radical curable composition comprising the α-(unsaturated alkoxyalkyl)acrylate composition according to claim 1.

13. The α-(unsaturated alkoxyalkyl)acrylate composition according to claim 1, wherein the nitrogen content is 80 ppm or less, per 100 wt. % of the α-(unsaturated alkoxyalkyl)acrylate.

14. The α-(unsaturated alkoxyalkyl)acrylate composition according to claim 1, wherein the nitrogen content is 50 ppm or less, per 100 wt. % of the α-(unsaturated alkoxyalkyl)acrylate.

15. A method for producing the α-(unsaturated alkoxyalkyl)acrylate composition according to claim 1,
wherein the method comprises reacting an acrylate having a hydroxyalkyl group at the α-position with an unsaturated alcohol represented by general formula (7) below

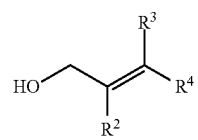

where $R^2$, $R^3$ and $R^4$ are the same as in the general formula (1); and
purifying crude α-(unsaturated alkoxyalkyl)acrylate to obtain purified α-(unsaturated alkoxyalkyl)acrylate, and then adding an antioxidant to the purified α-(unsaturated alkoxyalkyl)acrylate.

16. The method for producing the α-(unsaturated alkoxyalkyl)acrylate composition according to claim 15, wherein the unsaturated alcohol comprises allyl alcohol.

17. The method for producing the α-(unsaturated alkoxyalkyl)acrylate composition according to claim 15, wherein the method comprises carrying out a reaction in the presence of an amine catalyst.

18. A method for producing the α-(unsaturated alkoxyalkyl)acrylate composition according to claim 15, wherein the purifying comprises treating the crude α-(unsaturated alkoxyalkyl)acrylate composition with an inorganic alkali, and wherein the crude α-(unsaturated alkoxyalkyl)acrylate composition contains the acrylate having a hydroxyalkyl group at the α-position.

19. A method for producing the α-(unsaturated alkoxyalkyl)acrylate composition according to claim 15, wherein the method comprises reacting a polyfunctional compound with a monofunctional α-(unsaturated alkoxyalkyl)acrylate.

20. The method for producing the α-(unsaturated alkoxyalkyl)acrylate composition according to claim 15, wherein the reacting comprises transesterification of a polyhydric compound with the monofunctional α-(unsaturated alkoxyalkyl)acrylate.

* * * * *